Figure 1A:
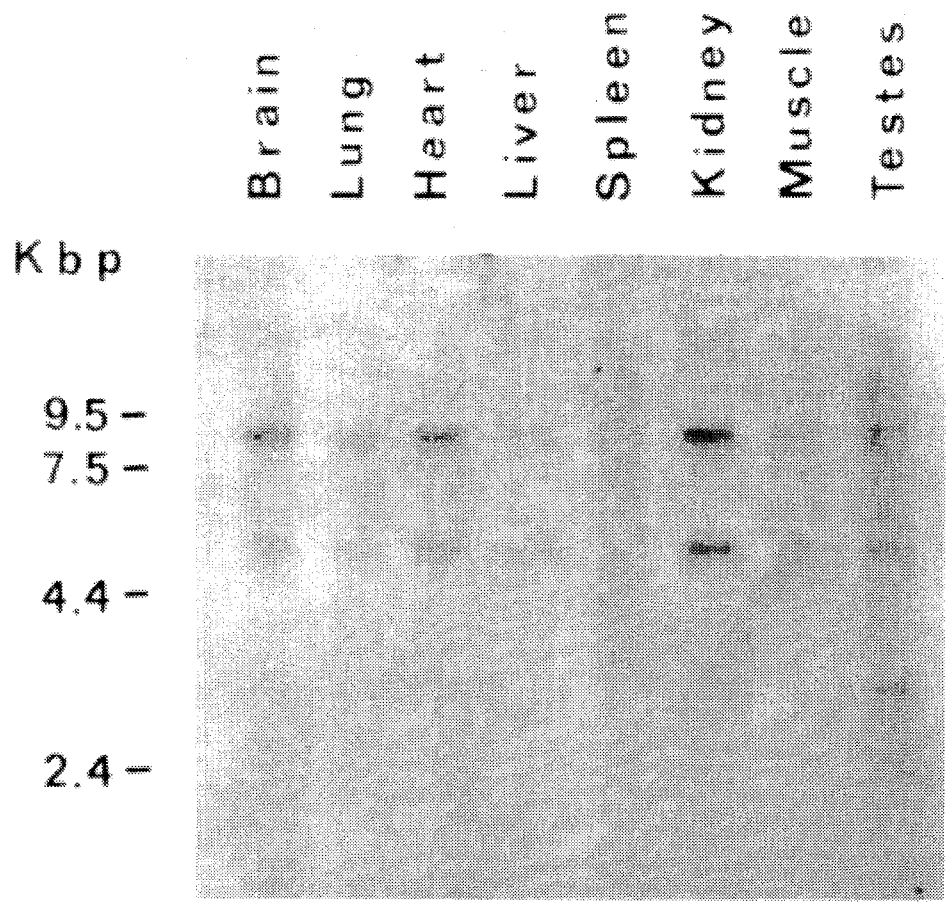

United States Patent [19]
Schlessinger

[11] Patent Number: 5,532,123
[45] Date of Patent: Jul. 2, 1996

[54] RECEPTOR-TYPE PHOSPHOTYROSINE PHOSPHATASE-γ

[75] Inventor: Joseph Schlessinger, New York, N.Y.

[73] Assignee: New York University, New York, N.Y.

[21] Appl. No.: 15,986

[22] Filed: Feb. 10, 1993

Related U.S. Application Data

[63] Continuation-in-part of Ser. No. 654,188, Feb. 26, 1991, abandoned, which is a continuation-in-part of Ser. No. 551,270, Jul. 11, 1990, abandoned.

[51] Int. Cl.$^6$ .......................... C12N 15/55; C12N 9/16; C12N 15/63; C12Q 1/68
[52] U.S. Cl. .................. 435/6; 435/69.1; 435/69.8; 435/70.1; 435/71.2; 435/196; 435/240.2; 435/252.3; 435/172.3; 435/320.1; 435/254.2; 536/23.1; 536/23.2; 935/14; 935/22; 935/56; 935/69; 935/70; 935/72
[58] Field of Search .......................... 435/69.1, 69.8, 435/70.1, 71.2, 196, 240.2, 252.3, 255, 172.3, 6, 320.1; 536/23.1, 23.2; 935/14, 22, 56, 69, 70, 72

[56] References Cited

FOREIGN PATENT DOCUMENTS

WO92/01050  1/1992  WIPO.

OTHER PUBLICATIONS

Kaplan et al., Cloning of three human tyrosine phosphatases reveals a multigene family of receptor–linked protein–tyrosine–phosphatases expressed in brain, Proc. Natl. Acad. Sci. USA 87: 7000–7004 (1990).
Sap et al., Cloning and expression of a widely expressed receptor tyrosine phosphatase, Proc. Natl. Acad. Sci. USA 87: 6112–6116 (1990).
Daum et al., Characterization of a human recombinant receptor–linked protein tyrosine phosphatase, J. Biol. Chem. 266: 12211–12215 (1991).
Gebbink et al., Cloning, expression and chromosomal localization of a new putative receptor–like protein tyrosine phosphatase, FEBS Lett. 290: 123–130 (1991).
Tsai et al., Isolation and characterization of temperature–sensitive and thermostable mutants of the human receptor–like protein tyrosine phosphatase LAR, J. Biol. Chem. 266(16): 10534–10543 (1991).
George and Parker, Preliminary characterization of phosphotyrosine phosphatase activites in human peripheral blood lymphocytes: Identification of CD45 as a phosphotyrosine phosphatase, J. Cell Biochem. 42: 71–81 (1990).
Jirik et al., Cloning of a novel receptor–linked protein tyrosine phosphatase from a human hepatoblastoma cell line, FASEB J. 4A: 2082 (Abstr. 2253) (1990).
Jirik et al., Cloning and chromosomal assignment of a widely expressed human receptor–like protein–tyrosine phosphatase, FEBS Lett. 273: 239–242 (1990).
Krueger et al., Structural diversity and evolution of human receptor–like protein tyrosine phosphatases, EMBO J. 9: 3241–3252 (1990).

Matthews et al., Identification of an additional member of the protein–tyrosine–phosphatase family: Evidence for alternative splicing in the tryosine phosphatase domain, Proc. Natl. Acad. Sci. USA 87: 4444–4448 (1990).
Ohagi et al., Sequence of a cDNA encoding human LRP (leukocyte common antigen–related peptide), Nucl. Acids Res. 18: 7159 (1990).
Streuli et al., Distinct functional roles of the two intracellular phosphatase like domains of the receptor–linked protein tyrosine phosphatases LCA and LAR, EMBO Journal 9: 2399–2407 (1990).
Kiener and Mittler, CD45–protein tyrosine phosphatase cross–linking inhibits T–cell receptor CD3–mediated activation in human T–cells, J. Immunol. 143: 23–28 (1989).
Mustelin et al., Rapid activation of the T–cell tyrosine protein kinase pp56lck by the CD45 phophotyrosine phosphatase, Proc. Natl. Acad. Sci. USA 86: 6302–6306 (1989).
Ostergaard et al., Expression of CD45 alters phosphorylation of the lck–encoded tyrosine protein kinase in murine lymphoma T–cell lines, Proc. Natl. Acad. Sci. USA 86: 8959–8963 (1989).
Hall et al., Complete exon–intron organization of the human leukocyte common antigen (CD45) gene, J. Immunol. 141: 2781–2787 (1988).
Streuli et al., A new member of the immunoglobulin superfamily that has a cytoplasmic region homologous to the leukocyte common antigen, J. Exp. Med. 168: 1523–1530 (1988).
Charbonneau et al., The leukocyte common antigen (CD45): A putative receptor–linked protein tyrosine phosphatase, Proc. Natl. Acad. Sci. USA 85: 7182–7186 (1988).
Ralph et al., Structural variants of human T200 glycoprotein (leukocyte–common antigen), EMBO J. 6: 1251–1257 (1987).
Streuli et al., Differential usage of three exons generates at least five different mRNAs encoding human leukocyte common antigens, J. Exp. Med. 166: 1548–1566 (1987).
Hariharan et al., Cloning and characterization of a receptor–class phosphotyrosine phosphatase gene expressed on central nervous system axons in Drosophila melanogaster, Proc. Natl. Acad. Sci. USA 88: 11266–11270 (1991).
Streuli et al., A family of receptor–linked protein tyrosine phosphatases in humans and Drosophila, Proc. Natl. Acad. Sci. USA 86: 8698–8702 (1989).

(List continued on next page.)

*Primary Examiner*—Robert A. Wax
*Assistant Examiner*—Rebecca Prouty
*Attorney, Agent, or Firm*—Pennie & Edmonds

[57] ABSTRACT

A novel receptor-type protein tyrosine phosphatase-γ (RPTPγ) protein or glycoprotein and the DNA coding therefor is expressed in a wide variety of mammalian tissues. The RPTPγ protein or glycoprotein may be produced by recombinant means. Antibodies to the protein, methods for measuring the quantity of the protein, methods for screening compounds, such as drugs, which can bind to the protein and inhibit or stimulate their enzymatic activity, are provided.

15 Claims, 22 Drawing Sheets

OTHER PUBLICATIONS

Gu et al., Identification, cloning, and expression of a cytosolic megakaryocyte protein–tyrosine–phosphatase with sequence homology to cytoskeletal protein 4.1, Proc. Natl. Acad. Sci. USA 88: 5867–5871 (1991).

Lombroso et al., Molecular characterization of a protein–tyrosine–phosphatase enriched in striatum, Proc. Natl. Acad. Sci. USA 88: 7242–7246 (1991).

Yang and Tonks, Isolation of a cDNA clone encoding a human protein–tyrosine phosphatase with homology to the cytoskeletal–associated proteins band 4.1, ezrin, and talin, Proc. Natl. Acad. Sci. USA 88: 5949–5953 (1991).

Chernoff et al., Cloning of a cDNA for a major human protein–tyrosine–phosphatase, Proc. Natl. Acad. Sci. USA, 87: 2735–2739 (1990).

Cool et al., Overexpression of a T–cell protein tyrosine phosphatase (PTPase) in BHK Cells, FASEB J. 4: A2078 (abstr. 2230) (1990).

Guan et al., Cloning and expression of a protein–tyrosine–phosphatase, Proc. Natl. Acad. Sci. USA 87: 1501–1505 (1990).

Thomas, et al., ABA, A novel member of the tyrosine phosphatase family, FASEB J. 4: A2078 (Abstr. 3140) (1990).

Tonks et al., CD45, an integral membrane protein tyrosine phosphatase, J. Biol. Chem. 265: 10674–10680 (1990).

Charbonneau et al., Human placenta protein–tyrosine–phosphatase: Amino acid sequence and relationship to a family of receptor–like proteins, Proc. Natl. Acad. Sci. USA 86: 5252–5256 (1989).

Cool et al., cDNA isolated from a human T–cell library encodes a member of the protein–tyrosine–phosphatase family, Proc. Natl. Acad. Sci. USA 86: 5257–5261 (1989).

Tonks et al., Purification of the major protein–tyrosine–phosphatases of human placenta, J. Biol. Chem. 263: 6722–6730 (1988).

Tonks et al., Demonstration that the leukocyte common antigen CD45 is a protein tyrosine phosphatase, Biochemistry 27: 8695–8701 (1988).

Matthews et al., Characterization of hematopoietic intracelluar protein tyrosine phosphatases: Description of a phosphatase containing an SH2 Domain and another enriched in proline–, glutamic acid–, serine–, and threonine–rich sequences, Molec. and Cell. Biol. 12: 2396–2405 (1992).

Plutzky et al., Isolation of a src homology 2–containing tyrosine phosphatase, Proc. Natl. Acad, Sci. USA 89: 1123–1127 (1992).

Yi et al., Protein tyrosine phosphatase containing SH2 domains: characterization, preferential expression in hematopoietic cells, and localization to human chromosome 12p12–p13, Mol. and Cell. Biol. 12: 836–846 (1992).

Shen et al., A protein–tyrosine phosphatase with sequence similarity to the SH2 domain of the protein–tyrosine kinases, Nature 352: 736–739 (1991).

Klarlund, Transformation of cells by an inhibitor of phosphatases acting on phosphotyrosine in proteins, Cell 41: 707–717 (1985).

Pallen et al., Purification of a phosphotyrosine phosphatase that dephosphorylates the epidermal growth factor receptor autophosphorylation sites, Ann. N.Y. Acad. Sci. 551: 299–308 (1988).

Butler et al., Characterization of a membrane–associated phosphotyrosyl protein phosphatase from the A431 human epidermoid carcinoma cell line, Eur. J. Biochem. 185: 475–483 (1989).

Cyert and Thorner, Putting it on and taking it off: Phosphoprotein phosphatase involvement in cell cycle regulation, Cell 57: 891–893 (1989).

Jones et al., Phosphotyrosyl–protein phosphatases, J. Biol. Chem. 264: 7747–7753 (1989).

Pingel and Thomas, Evidence that the leukocyte–common antigen is required for antigen–induced T lymphocyte proliferation, Cell 58: 1055–1065 (1989).

Pot and Dixon, A thousand and two protein tyrosine phosphatases, Biochem. Biophys. Acta. 1136: 35–43 (1992).

Fischer et al., Protein tyrosine phosphatases: A diverse family of intracellular and transmembrane enzymes, Science 253: 401–406 (1991).

Hunter, Protein–tyrosine phosphatases: The other side of the coin, Cell 58: 1013–1016 (1989).

Thomas, The leukocyte common antigen family, Ann. Rev. Immunol. 7: 339–369 (1989).

Tonks and Charbonneau, Protein tyrosine dephosphorylation and signal transduction, Trends in Biochem. Sci. 14: 497–500 (11989).

Signal peptide

```
  1 ATGCGGAGGTTACTGGAACCGTGTTGGTGGATTTTGTTCCTGAAAATCACCAGTTCCGTG   60
  1 [M  R  R  L  L  E  P  C  W  W  I  L  F  L  K  I  T  S  S  V]  20
```

CAH-like

```
 61 CTCCATTATGTCGTGTGCTTCCCCGCCGTTGACAGAAGGCTACGTTGGGGCCCTGCACGAG  120
 21  L  H  Y  V  V  C  F  P  P  A  L  T  E  G  Y  V  G  A  L  H  E   40

121 AATAGACACGGCAGCGCAGTGCAGATCCGCAGGCTTCAGGCAAGGCTTCAGGCGACCCGTACTGG  180
 41  N  R  H  G  S  A  V  Q  I  R  R  R  K  A  S [G  D  P  Y  W   60

181 GCCTACTCTGGTGCCTATGGTCCTGAGCACTGGGTCACGTCTAGTGTCAGTGTGTGGAGC  240
 61  A  Y  S  G  A  Y  G  P  E  H  W  V  T  S  S  V  S  C  G  S   80

241 CGTCACCAGTCTCCTATTGACATTTTAGACCAGTATGCGCGTGTGGGAGAAGAATACCAG  300
 81  R  H  Q  S  P  I  D  I  L  D  Q  Y  A  R  V  G  E  E  Y  Q  100

301 GAACTGCAACTCGATGGCTTCGACAATGAGTCTTCTAACAAACCTGGATGAAAAACACA  360
101  E  L  Q  L  D  G  F  D  N  E  S  S  N  K  T  W  M  K  N  T  120

361 GGGAAAacagtcgccatccTTCTGAAAGACGACTATTTTGTCAGTGGAGCTGGTCTACCT  420
121  G  K  T  V  A  I  L  L  K  D  D  Y  F  V  S  G  A  G  L  P  140
```

FIG. 3A

```
421 GGCAGATTCAAAGCTGAGAAGGTGGAATTTCACTGGGGCCACAGCAATGGCTCAGCGGGC 480
141  G  R  F  K  A  E  K  V  E  F  H  W  G  H  S  N  G  S  A  G   160

481 TCTGAACACAGCATCAATGGCAGAGTTTCCTGTGAGATGCAGATTTCTTTTACAAT 540
161  S  E  H  S  I  N  G  R  R  F  P  V  E  M  Q  I  F  F  Y  N   180

541 CCAGATGACTTTGACAGCTTTCAAACCGCAATTTCTGAGAACAGAATAATCGGAGCCATG 600
181  P  D  D  F  D  S  F  Q  T  A  I  S  E  N  R  I  I  G  A  M   200

601 GCCATATTTTTTCAAGTCAGTCCGAGGGACAATTCTCACTGGATCCTATTATCCACGGG 660
201  A  I  F  F  Q  V  S  P  R  D  N  S  A  L  D  P  I  I  H  G   220

661 TTGAAGGGTGTCGTACATCATGAGAAGGAGACCTTTctggatccTttcgtcctccgggac 720
221  L  K  G  V  V  H  H  E  K  E  T  F  L  D  P  F  V  L  R  D   240

721 ctcctgcctgcatccctggcagctattatcggtacacaggttccttgaccaccaccg 780
241  L  L  P  A  S  L  G  S  Y  Y  R  Y  T  G  S  L  T  T  P  P   260

781 tgtagcgaaatAGTGGAGTGGATAGTCTTCCGAGACCCGTCCCCATCTCTTACCATCAG 840
261  C  S  E  I  V  E  W  I  V  F  R  R  P  V  P  I  S  Y  H  Q   280
```

FIG. 3B

```
841  CTTGAGGCTTTTATTCCATCTTCACCACGGAGCAGCAGCAAGACCATGTCAAGTCGGTGGAG   900
281   L  E  A  F  Y  S  I  F  T  T  E  Q  Q  Q  D  H  V  K  S  V  E    300

901  TATCTGAGAAATAACTTTCGACCACAGCAGGTCTGCATGACAGGGTGTGTCCAAGTCC        960
301   Y  L  R  N  N  F  R  P  Q  Q  R  L  H  D  R  V  V  S  K  S       320

961  GCCGTCCGTGACTCCTGAACCACGACATGACAGACTTCTTAGAAAACCCACTGGGACA       1020
321   A  V] R  D  S  W  N  H  D  M  T  D  F  L  E  N  P  L  G  T       340

1021 GAAGCCTCTAAAGTTGCAGCTCTCCACCATCCACATGAAGGTGCAGCCTCTGAACCAG      1080
341   E  A  S  K  V  C  S  S  P  P  I  H  M  K  V  Q  P  L  N  Q       360

1081 ACGGCACTGCAGGTGTCTCCTGGAGCCCGGAGACTATCTACCACCCCATCATGAAC        1140
361   T  A  L  Q  V  S  W  S  Q  P  E  T  I  Y  H  P  P  I  M  N       380

1141 TACATGATCTCCTACAGCTGGACCAAGAATGAGGACGAAGAGAAGGAGAAGACGTTTACAAAG 1200
381   Y  M  I  S  Y  S  W  T  K  N  E  D  E  K  E  K  T  F  T  K       400

1201 GACAGGACAAAGACTTGAAGCCACCATTAGCCATGTCTCACCCGATAGCCTTTACCTG      1260
401   D  S  D  K  D  L  K  A  T  I  S  H  V  S  P  D  S  L  Y  L       420
```

FIG. 3C

```
1261 TTCCGAGTCCAGGCCGTGTGTCGGAACGACATGCGCAGGACTTTAGCCAGACGATGCTG 1320
 421  F  R  V  Q  A  V  C  R  N  D  M  R  S  D  F  S  Q  T  M  L   440

1321 TTTCAAGCTAATACCACTCGAATATTCCAAGGACCAGAATAGTGAAAACAGGAGTGCCC 1380
 441  F  Q  A  N  T  T  R  I  F  Q  G  T  R  I  V  K  T  G  V  P   460

1381 ACAGGGTCTCCTGCCTCTTCAGCCGACATGGCCCCCATCAGCTCGGGTCTTCTACCTGG 1440
 461  T  A  S  P  A  S  S  A  D  M  A  P  I  S  S  G  S  S  T  W   480

1441 ACGTCCTCCTGGCATCCTCCATTTGTTTCCATGGCAACTGGAATGGGCCCCTCCTCC 1500
 481  T  S  S  G  I  P  F  S  F  V  S  M  A  T  G  M  G  P  S  S   500

1501 AGTGGCAGCCAGGCCACAGTGGCCTCGGTCACCAGCACGCTGCTCGCCGGCCTGGGG 1560
 501  S  G  S  Q  A  T  V  A  S  V  V  T  S  T  L  L  A  G  L  G   520

1561 TTCGGCGGTGGTGGCCATCCTCTTCCCCAGCACTGTGTGGCCCACGGCCCTCCCGACG 1620
 521  F  G  G  G  G  I  S  S  F  P  S  T  V  W  P  T  R  L  P  T   540

1621 GCCGCCTCAGCCAAGCAGGCgCTAGCCAGTCCTAGCCACCAGAGGCCTTGGCT 1680
 541  A  A  S  K  Q  A  A  R  P  V  L  A  T  T  E  A  L  A   560

FIG. 3D
```

```
1681 TCTCCAGGGCCCGATGGTGATTCGTCACCAAGGACGGGAGGCACCGAGGAAGGA 1740
 561 S  P  G  P  D  G  D  S  S  P  T  K  D  G  E  G  T  E  E  G      580

1741 GAGAAGGATGAgaaaagcgagagtgaggagtgagggagcggagcacgagaggaggatggagag 1800
 581 E  K  D  E  K  S  E  S  E  D  G  E  R  E  H  E  E  D  G  E      600

1801 aaggactccgaaaagaaggagaagaagagtgggtgacccacgctgccgaggagcggAatcag 1860
 601 K  D  S  E  K  K  E  K  S  G  V  T  H  A  A  E  E  R  N  Q      620

1861 acggagcccagcccccaCaccctcgtctcctaacaggacTGCCGAGGGCATCAgact 1920
 621 T  E  P  S  P  T  P  S  S  P  N  R  T  A  E  G  G  H  Q  T      640

1921 ataccctggccatgagcaggatcacactgccgtcccacagaccagacggtcggaaggagg 1980
 641 I  P  G  H  E  Q  D  H  T  A  V  P  T  D  Q  T  G  G  R  R      660

1981 gatgCcGgccggcccaggcctggacccgacatggtcacctccacccaagtgcccccaccgcc 2040
 661 D  A  G  P  G  L  D  D  P  D  M  V  T  S  T  Q  V  P  P  T  A    680

2041 acagagaggagcagtatgcagggatgatcccaagagcccgaaatgccatctaaaagcct 2100
 681 T  E  E  Q  Y  A  G  S  D  P  K  R  P  E  M  P  S  K  K  P      700
```

FIG. 3E

```
2101 atgtCccgcgcgggaccgattctgaagacagcagattatcactgttaatccagcgGAA 2160
701  M  S  R  G  D  R  F  S  E  D  S  R  F  I  T  V  N  P  A  E    720

2161 AAAAACACCTCTGGAATGATAAGCCGCCCTGCTCCAGGAGGATGGAGTGGATCATCCCT 2220
721  K  N  T  S  G  M  I  S  R  P  A  P  G  R  M  E [W  I  I  P    740
                                                    Trans-
                                                    membrane
2221 CTGATTGTGGTATCAGCCTTGACCTTCGTGTGCCTCATCCTTCTCATTGCTGTCCTCGTT 2280
741  L  I  V  V  S  A  L  T  F  V  C  L  I  L  L  I  A  V  L  V    760

2281 TACTGGAGAGAGGGTGTAACAAAATAAAGTCCAAGGGCTTTCCCAGACGTTCCGTGAAGTg 2340
761  Y  W] R  G  C  N  K  I  K  S  K  G  F  P  R  R  F  R  E  V    780

2341 CCTTCTTCTGGGAGAGAGAGAGGGAGCAGAAAATGTTTCAGACTGCTCATTC 2400
781  P  S  S  G  E  R  G  E  K  G  S  R  K  C  F  Q  T  A  H  F    800

2401 TATGTGGAAGACAGCAGTTCACCTGAGTGCCCTAATGAAAGTATTCCTATTATTCCT 2460
801  Y  V  E  D  S  S  S  P  R  V  V  P  N  E  S  I  P  I  I  P    820

2461 ATTCCGGATGACATGGAAGCCATTCCTGTCAAACAGTTTGTCAAACACATCGGTGAGCTC 2520
821  I  P  D  D  M  E  A  I  P  V  K  Q  F  V  K  H  I  G  E  L    840
```

FIG. 3F

```
2521 TATTCTAATAACCAGCATGGGTTCTCTGAGGATTTTGAGGAAGTCCAGCGCTGTacTgCT 2580
841  Y  S  N  N  Q  H  G  F  S  E  D  F  E  E  V  Q  R  C  T  A   860

2581 GATATGAACATCACTGCAGAGCATTCCAATCATCCAGAAACAAGCACAAAACAGATAC 2640
861  D  M  N  I  T  A  E  H  S  N  H  P  E [N  K  H  K  N  R  Y   880

2641 ATCAACACATTTTAGCATATGATCACAGTAGGGTGAAGTAAGACCTTTACCAGGAAAGAC 2700
881  I  N  I  L  A  Y  D  H  S  R  V  K  L  R  P  L  P  G  K  D   900

2701 TCTAAGCACAGGGACTACATTAATGCAAACTATGTTGATGGTTACAACAAGCAAAAGCC 2760
901  S  K  H  S  D  Y  I  N  A  N  Y  V  D  G  Y  N  K  A  K  A   920

2761 TACATTGCCACCAAGGACCTTTGAAGTCTACATTGAAGATTTCTGGAGGATGATTTGG 2820
921  Y  I  A  T  Q  G  P  L  K  S  T  F  E  D  F  W  R  M  I  W   940

2821 GAACAAAACACTGGAATCATTGTGATGATTACGAACCTTGTGAAAAGGAAGACGAAAA 2880
941  E  Q  N  T  G  I  I  V  M  I  T  N  L  V  E  K  G  R  R  K   960

2881 TGTGATCAGTATTGGCCAACAGAGAACAGTGAGGAATATGGAAACATTATTGTCACGCTG 2940
961  C  D  Q  Y  W  P  T  E  N  S  E  E  Y  G  N  I  I  V  T  L   980
```

PTPase Domain I

FIG. 3G

```
2941 AAGAGCACAAAATACATGCCTGCTACACTGTTCGTTTTCAATCAGAATACAAAA 3000
 981  K  S  T  K  I  H  A  C  Y  T  V  R  R  F  S  I  R  N  T  K  1000

3001 GTGAAAAAGGGTCAGAAGGGAAATCCCAAGGTGTCAGAATGAAAGGTAGTGATCCAG 3060
1001  V  K  K  G  Q  K  G  N  P  K  G  R  Q  N  E  R  V  V  I  Q  1020

3061 TATCACTATACACAGTGCCTGACATGGGAGTTCCCGAGTATGCCCTTCCAGTACTGACT 3120
1021  Y  H  Y  T  Q  W  P  D  M  G  V  P  E  Y  A  L  P  V  L  T  1040

3121 TTCGTGAGGAGATCCTCAGCAGCTCGGATGCCAGAAACGGGCCCTGTGTTGTGCACTGC 3180
1041  F  V  R  R  S  S  A  A  R  M  P  E  T  G  P  V  L  V  H  C  1060

3181 AGTGCTGGTGTGTGGGCAGAACAGGCCACCTATATTGTAATAGACAGCATGCAACAGATA 3240
1061  S  A  G  V  G  R  T  G  T  Y  I  V  I  D  S  M  L  Q  Q  I  1080

3241 AAAGACAAAAGCACAGTTAACGTCCTGGGATTCCTGAAGCATATCAGGACACAGCGTAAC 3300
1081  K  D  K  S  T  V  N  V  L  G  F  L  K  H  I  R  T  Q  R  N  1100

3301 TACCTCGTCCAGACTGAGGAGCAGTACATTTTCATCCATGATGCCTTGTTGGAAGCCATT 3360
1101  Y  L  V  Q  T  E  E  Q  Y  I  F  I  H  D  A  L  L  E] A  I  1120
```

FIG. 3H

```
3361 CTTGGAAAGGAGACTGAAGTATCTTCAAATCAGCTGCACAGCTATGTTAACAGCATCCTT 3420
1121  L  G  K  E  T  E  V  S  S  N  Q  L  H  S  Y  V  N  S  I  L  1140

3421 ATACCAGGAGTAGGAGGAAAGACAACGACTGGAAAGCAATTCAAGCTGGTCACACAGTGT 3480
1141  I  P  G  V  G  G  K  T  R  L  E  K  Q  F  K  L  V  T  Q  C  1160

3481 AATGCAAAATATGTGGAATGTTTCAGTGCTCAGAAAGAGTGTAACAAAGAAAAGAACAGA 3540
1161  N  A  K  Y  V  E  C  F  S  A  Q  K  E  C  [N  K  E  K  N  R  1180
PTPase
Domain II
3541 AACTCTTCAGTTGTGCCATCTGAGCGTGCTCGAGTGGGTCTTGCACCATTGCCTGGAATg 3600
1181  N  S  S  V  V  P  S  E  R  A  R  V  G  L  A  P  L  P  G  M  1200

3601 aaaggaacagattacattaatgctctctattatatcatggctattatagagcaatgaattt 3660
1201  K  G  T  D  Y  I  N  A  S  Y  I  M  G  Y  Y  R  S  N  E  F  1220

3661 attataactcagatcctctgccacatacgaaagatttctggcgaatgattgggat 3720
1221  I  I  T  Q  H  P  L  P  H  T  T  K  D  F  W  R  M  I  W  D  1240

3721 cataacgcacagatcattgtgctgccagacaaccagagcttggcagaagatgagttt 3780
1241  H  N  A  Q  I  I  V  M  L  P  D  N  Q  S  L  A  E  D  E  F  1260
```

FIG. 3I

```
3781 gtgtactGGCCAAGTCGAGAAGAATCCATGAACTGTGAGCCTTtaccgtcaccctatc 3840
1261  V  Y  W  P  S  R  E  E  S  M  N  C  E  A  F  T  V  T  L  I  1280

3841 agcaaagacagactgtgcctctctaatgaagaacaaattatcatccatgacttatcctt 3900
1281  S  K  D  R  L  C  L  S  N  E  E  Q  I  I  H  D  F  I  L  1300

3901 gaagctacacaggatgactatgtcttagaagttcggcacttcagtgtcccaaatggcct 3960
1301  E  A  T  Q  D  D  Y  V  L  E  V  R  H  F  Q  C  P  K  W  P  1320

3961 aacccagatgcccccataagtagtacctttgaacttatcaacgtcatcaaggaagaggcc 4020
1321  N  P  D  A  P  I  S  S  T  F  E  L  I  N  V  I  K  E  E  A  1340

4021 ttaacaagggatggtCCCACCATTGTTCATGATGAGTATGGAGCAGTTTCAGCAGGAATG 4080
1341  L  T  R  D  G  P  T  I  V  H  D  E  Y  G  A  V  S  A  G  M  1360

4081 TTATGTGCCcttaccaccctgtcccagcaactggagaatgaaaatgctgtggatgttttc 4140
1361  L  C  A  L  T  T  L  S  Q  Q  L  E  N  E  N  A  V  D  V  F  1380

4141 caggttgcaaaatgatcaatcttatgaggcctggagtattcacagacattgaacaatac 4200
1381  Q  V  A  K  M  I  N  L  M  R  P  G  V  F  T  D  I  E  Q  Y  1400
```

FIG. 3J 4201 cagttcatctataaagcaaggcttagcTTGGTCAGCACTAAAGAAAATGGAAATGGTCCC 4260
1401  Q  F  I  Y  K  A  R  L  S] L  V  S  T  K  E  N  G  N  G  P  1420

4261 ATGacagtagacAAAAAATGGTGCTGTTCTTATTGCAGATGAATCAGACCCTGCTGAGAGc 4320
1421  M  T  V  D  K  N  G  A  V  L  I  A  D  E  S  D  P  A  E  S  1440

4321 atggagtccctagtgtga 4338
1441  M  E  S  L  V  *  1446

FIG. 3K

FIG.4A

```
        1   MRRLLEPCWWILFLKITSSVLHYVVCFPALTEGYYGALHENRHGSAVQIRRRKASGDPYWAYSGAYGPEHWVTSSVSCGSRHQSPIDILDQYARVGEEYQ
Human       ─────────────────────                                 ▽
Mouse                          TQSQDS                                                         GS    HH    D              CAH 101   ELQLDGFDNESSNKTMMKNTGKTVAILLKDDYFVSGAGLPGRFKAEKVEFHMCHSNGSAGSEHSINCRRFPVEMQIFFYNPDDFSFQTAISENRIIGAM
Human             ▲
Mouse                                              AN                                              V 201   AIFFQVSPRDNSALDPIIHCLKGVVHHEKETFLDPFVLRDLLPASLGSYYRYTGSLTPPCSEIVEWIVFRRPVPISYHQLEAFYSIFTTEQQDHVKSVE
Human
Mouse                                                                        I 301   YLRNNFRPQQRLHDRVVSKSAVRDSWNHDMTDFLENPLGTEASKVCSSPPIHMKVQPLNQTALQVSWSQPETIYHPPIMMYMISYSWTKNEDEKEKTFTK
Human       ──────────────────────────────────────┐                ▲
Mouse                   AN        A    LA    D 401   DSDKDLKATISHVSPDSLYLFRVQAVCRNDMRSDFSQTMLFQANTTRIFQGTRIVKTGVPTASPASSADMAPISSCGSSTWTSSGIPFSFVSMATGMGPSS
Human                                      ▲
Mouse 501   SGSQATVASVVTSTLLAGLGFGGGGISSFPSTVWPTRLPTAASASKQAARPVLATTEALASPCPDCGDSSPTKDGEGTEEGEKDEKSESEDGEREHEEDGE
Human                                                              SA    G T               VHASSS        E       E-

601   KDSEKKEKSGVTHAAEERMQTEPSTPTPSSPNRT-AEGGHQTIPCGHEQDHTAVPTDQTGRRRDAGPGLDPDMVTSTQVPPTATEEQYAGSDPKRPEMPSKK
Human                   ▲
Mouse       EA T ASDR AA   H A        RR   SPA  P--HVA D    LVD A            HS  R 701   PMSRGDRFSEDSRFITVNPAEKNTSGMISRPAPGRMEWIIPLIWVSALTFVCLILLIAVLVYWRGCNKIKSKGFPRRFREVPSSGERGEKGSRKCFQTAH
Human                         ▲                    ─────────────────────────────
Mouse              K                       L  S                          V                      S
```

```
                                                                                                    D I
      FYVEDSSSPRVVPNESIPIIPIPDDMEAIPVKQFVKHIGELYSNNQHGFSEDFEEVQRCTADMNITAEHSNHPENKHKNRYINILAYDHSRVKLRPLPGK
801
Human
Mouse                     V                G            S                              D DSKHSDYINANYVDGYNKAKAYIATQGPLKSTFEDFWRMIWEQNTGIIVMITNLVEKGRRKCDQYMPTENSEEYGNIIVTLKSTKIHACYTVRRFSIRNT
901
Human
Mouse                                                          I              T               V       LV KVKKGQKGNPKGRQNERVVIQYHYTQMPDMGYPEYALPVLTFVRRSSAARMPETGPVLVHCSAGVGRTIGTYIVIDSMLQQIKDKSTVNVLGFLKHIRTQR
1001
Human
Mouse                                                                     DM NYLVQTEEQYIFIHDALLEAILGKETEVSSNQLHSYVNSILIPGVGGKTRLEKQFKLVTQCNAKYVECFSAQKEQNKEKNRNSSVVPSERARVGLAPLPG
1101
Human
Mouse                         A     S                                                                 A D II
      MKGTDYINASYIMGYYRSNEFIITQHPLPHTKDFWRMIWDHNAQIIVMLPDNQSLAEDEFVYMPSREESMNCEAFTVTLISKDRLCLSNEEQIIHDFI
1201
Human
Mouse                                                  I LEATQDDYVLEVRHFQCPKWPNPDAPISSTFELINVIKEEALTRDGPTIVHDEYGAVSAGMLCALTTLSQQLENENAVDVFQVAKMINLMRPGVFTDIEQ
1301
Human
Mouse YQFIYKARLSLVSTKENGNGPMTVDKNGAVLIADESDPAESMESLV*
1401
Human
Mouse   V   M               I                G      T E
```

FIG.4B

```
Fbn III-7   LSPPTNLHLEANPDTGVLTVSWERSIT....PDITGYRITITP......TNGQQGTALEEVVHADQSSCT............FDNLSPGLEYNVSVY..TVKDDKESVPISDTIIP
Contac      PGPPGIRIEEIRDTAV.ALTWSRCTDN..HSPISKYTIQSKTFLSEEWKDAKTEPSDIEGNWESAR............VIDLIPWMEYEFRIIATNTLGTGEPSMPSQRI...
HLAR        SGPPRKVEVEPLNSTAV.HVYWKLPVPSKQHGQIRGYQV...TYVRLENGEPRGLPIIQDVMLAEAQW..RPEESEDYETTISGLTPETTYSVTVAAYTTKGDGARSKPKIVT..
HPTP δ      SGPPRKVEVEAVNSTSV.KVSMRSPVPNKQHGQIRGYQV...HYVRMENGEPKGQPMLKDVMLADAQW..EFDDTTEHDMIISGLQPETSYSLTVIAYTKGDGARSKPKLVS..
HPTP γ      SSPPIHMKVQPLNQTAL.QVSWSQP.ETIYHPPIMNYMI..SYSWTKNEDEKEKTFTKD.............SDKDLKATISHVSPDSLYLFRVQAVCRNDMRSDFSQTMLF..
Consensus   ——PP————E———T—V—V—W—————————H—[—Y———————————————L—P———Y———V—A—————
```

PERCENT IDENTITY:

| | RPTPγ human | RPTPγ mouse | CAH I human | CAH II human | CAH III human | CAH VI sheep | CAH-r.p mouse | CAH-r.p. vacc. virus |
|---|---|---|---|---|---|---|---|---|
| RPTPγ human | 100.0 | 98.1 | 35.6 | 38.9 | 39.8 | 37.0 | 35.3 | 34.5 |
| RPTPγ mouse | | 100.0 | 35.6 | 39.2 | 40.2 | 37.0 | 35.3 | 34.9 |
| CAH I human | | | 100.0 | 64.2 | 63.3 | 39.1 | 47.1 | 40.1 |
| CAH II human | | | | 100.1 | 63.0 | 42.7 | 47.3 | 41.7 |
| CAH III human | | | | | 100.0 | 44.4 | 45.6 | 42.6 |
| CAH VI sheep | | | | | | 100.0 | 40.8 | 36.2 |
| CAH-r.p. mouse | | | | | | | 100.0 | 33.6 |
| CAH-r.p. vacc.v | | | | | | | | 100.0 |

FIG.6C

```
        56
RPTPγ   GDPYWAYSGAYGPEHWVTSSVSCGSRHQSPIDILDQYARVGEEYQELQLD
        34  ||||    |     ||  ||||   |       |         |
RPTPβ       EEIGWSYTGALNQKNWGKKYPTCNSPKQSPINIDEDLTQVNVNLKKLKFQ

106
        GFDNESSNKTWMKNTGKTVAILLKDDYFVSGAGLPGRFKAEKVEFHWGHS
        84  |  |  |    |  ||||||  |   ||  |||     ||| |  ||||
        GWDKTSLENTFIHNTGKTVEINLTNDYRVSGGVSEMVFKASKITFHWGKC

156
        N-GSAGSEHSINGRRFPVEMQIFFYNPDDFDSFQTAISENRIIGAMAIFF
        134 | | ||||| |  || ||||   |  ||| |          | ||      CAH
        NMSSDGSEHSLEGQKFPLEMQIYCFDADRFSSFEEAVKGKGKLRALSILF

205
        QVSPRDNSALDPIIHGLKGVVHHEKETFLDPFVLRDLLPASLGSYYRYTG
        184 ||   |    ||| |   |      |  ||||  |  ||| |   ||   |
        EVGTEENLDFKAIIDGVESVSRFGKQAALDPFILLNLLPNSTDKYYIYNG

255
        SLTTPPCSEIVEWIVFRRPVPISYHQLEAFYSIFTTEQQDHVKSVEYLRN
        234 |||  |||    |  ||||   ||  ||   ||    |      |    |||
        SLTSPPCTDTVDWIVFKDTVSISESQLAVFCEVLTMQQSGYVMLMDYLQN

305
        NFRPQQ-RLHDRVVSKSAV RDSWNHDMTDFLENPLGTEASKVC SSPPI
        284 ||| ||      ||          ||                  ||  |||||
        NFREQQYKFSRQVFSSYTG KEEIHEA——————————VC SSEPE

252
        HMKVQPLNQTALQVSWSQPETIYHPPIMNYMISYSWTKNEDEKEKTFTKD
        317  ||||| |     |   |     |        |        ||      | |
        NVQADPENYTSLLVTWERPRVVYDTMIEKFAVLYQQLDGEDQTKHEFLTD   FN 401                                          441
        SDKDLKATISHVSPDSLYLFRVQAVCRNDMRSDFSQTMLF
        366 ||  |     |    |   |   |||       |        406
        GYQDLGAILNNLLPNMSYVLQIVAICTNGLYGKYSDQLIV
```

FIG.8A

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 4338 base pairs
( B ) TYPE: nucleic acid
( C ) STRANDEDNESS: double
( D ) TOPOLOGY: unknown ( i i ) MOLECULE TYPE: cDNA ( i x ) FEATURE:
( A ) NAME/KEY: CDS
( B ) LOCATION: 1..4335

( x i ) SEQUENCE DESCRIPTION: SEQ ID NO:1:

| ATG | CGG | AGG | TTA | CTG | GAA | CCG | TGT | TGG | TGG | ATT | TTG | TTC | CTG | AAA | ATC | 48 |
| Met | Arg | Arg | Leu | Leu | Glu | Pro | Cys | Trp | Trp | Ile | Leu | Phe | Leu | Lys | Ile | |
| 1 | | | | 5 | | | | | 10 | | | | | 15 | | |

| ACC | AGT | TCC | GTG | CTC | CAT | TAT | GTC | GTG | TGC | TTC | CCC | GCG | TTG | ACA | GAA | 96 |
| Thr | Ser | Ser | Val | Leu | His | Tyr | Val | Val | Cys | Phe | Pro | Ala | Leu | Thr | Glu | |
| | | | 20 | | | | | 25 | | | | | 30 | | | |

| GGC | TAC | GTT | GGG | GCC | CTG | CAC | GAG | AAT | AGA | CAC | GGC | AGC | GCA | GTG | CAG | 144 |
| Gly | Tyr | Val | Gly | Ala | Leu | His | Glu | Asn | Arg | His | Gly | Ser | Ala | Val | Gln | |
| | | 35 | | | | | 40 | | | | | 45 | | | | |

| ATC | CGC | AGG | CGC | AAG | GCT | TCA | GGC | GAC | CCG | TAC | TGG | GCC | TAC | TCT | GGT | 192 |
| Ile | Arg | Arg | Arg | Lys | Ala | Ser | Gly | Asp | Pro | Tyr | Trp | Ala | Tyr | Ser | Gly | |
| | 50 | | | | | 55 | | | | | 60 | | | | | |

| GCC | TAT | GGT | CCT | GAG | CAC | TGG | GTC | ACG | TCT | AGT | GTC | AGC | TGT | GGG | AGC | 240 |
| Ala | Tyr | Gly | Pro | Glu | His | Trp | Val | Thr | Ser | Ser | Val | Ser | Cys | Gly | Ser | |
| 65 | | | | | 70 | | | | | 75 | | | | | 80 | |

| CGT | CAC | CAG | TCT | CCT | ATT | GAC | ATT | TTA | GAC | CAG | TAT | GCG | CGT | GTT | GGG | 288 |
| Arg | His | Gln | Ser | Pro | Ile | Asp | Ile | Leu | Asp | Gln | Tyr | Ala | Arg | Val | Gly | |
| | | | | 85 | | | | | 90 | | | | | 95 | | |

| GAA | GAA | TAC | CAG | GAA | CTG | CAA | CTC | GAT | GGC | TTC | GAC | AAT | GAG | TCT | TCT | 336 |
| Glu | Glu | Tyr | Gln | Glu | Leu | Gln | Leu | Asp | Gly | Phe | Asp | Asn | Glu | Ser | Ser | |
| | | | 100 | | | | | 105 | | | | | 110 | | | |

| AAC | AAA | ACC | TGG | ATG | AAA | AAC | ACA | GGG | AAA | ACA | GTC | GCC | ATC | CTT | CTG | 384 |
| Asn | Lys | Thr | Trp | Met | Lys | Asn | Thr | Gly | Lys | Thr | Val | Ala | Ile | Leu | Leu | |
| | | | 115 | | | | | 120 | | | | | 125 | | | |

| AAA | GAC | GAC | TAT | TTT | GTC | AGT | GGA | GCT | GGT | CTA | CCT | GGC | AGA | TTC | AAA | 432 |
| Lys | Asp | Asp | Tyr | Phe | Val | Ser | Gly | Ala | Gly | Leu | Pro | Gly | Arg | Phe | Lys | |
| | 130 | | | | | 135 | | | | | 140 | | | | | |

| GCT | GAG | AAG | GTG | GAA | TTT | CAC | TGG | GGC | CAC | AGC | AAT | GGC | TCA | GCG | GGC | 480 |

| | | | | | | | | | | | | | | | | |
|---|---|---|---|---|---|---|---|---|---|---|---|---|---|---|---|---|
| Ala | Glu | Lys | Val | Glu | Phe | His | Trp | Gly | His | Ser | Asn | Gly | Ser | Ala | Gly | |
| 145 | | | | 150 | | | | | 155 | | | | | 160 | | |
| TCT | GAA | CAC | AGC | ATC | AAT | GGC | AGG | AGG | TTT | CCT | GTT | GAG | ATG | CAG | ATT | 528 |
| Ser | Glu | His | Ser | Ile | Asn | Gly | Arg | Arg | Phe | Pro | Val | Glu | Met | Gln | Ile | |
| | | | | 165 | | | | | 170 | | | | | 175 | | |
| TTC | TTT | TAC | AAT | CCA | GAT | GAC | TTT | GAC | AGC | TTT | CAA | ACC | GCA | ATT | TCT | 576 |
| Phe | Phe | Tyr | Asn | Pro | Asp | Asp | Phe | Asp | Ser | Phe | Gln | Thr | Ala | Ile | Ser | |
| | | | 180 | | | | | 185 | | | | | 190 | | | |
| GAG | AAC | AGA | ATA | ATC | GGA | GCC | ATG | GCC | ATA | TTT | TTT | CAA | GTC | AGT | CCG | 624 |
| Glu | Asn | Arg | Ile | Ile | Gly | Ala | Met | Ala | Ile | Phe | Phe | Gln | Val | Ser | Pro | |
| | | 195 | | | | | 200 | | | | | 205 | | | | |
| AGG | GAC | AAT | TCT | GCA | CTG | GAT | CCT | ATT | ATC | CAC | GGG | TTG | AAG | GGT | GTC | 672 |
| Arg | Asp | Asn | Ser | Ala | Leu | Asp | Pro | Ile | Ile | His | Gly | Leu | Lys | Gly | Val | |
| | 210 | | | | | 215 | | | | | 220 | | | | | |
| GTA | CAT | CAT | GAG | AAG | GAG | ACC | TTT | CTG | GAT | CCT | TTC | GTC | CTC | CGG | GAC | 720 |
| Val | His | His | Glu | Lys | Glu | Thr | Phe | Leu | Asp | Pro | Phe | Val | Leu | Arg | Asp | |
| 225 | | | | | 230 | | | | | 235 | | | | | 240 | |
| CTC | CTG | CCT | GCA | TCC | CTG | GGC | AGC | TAT | TAT | CGG | TAC | ACA | GGT | TCC | TTG | 768 |
| Leu | Leu | Pro | Ala | Ser | Leu | Gly | Ser | Tyr | Tyr | Arg | Tyr | Thr | Gly | Ser | Leu | |
| | | | | 245 | | | | | 250 | | | | | 255 | | |
| ACC | ACA | CCA | CCG | TGT | AGC | GAA | ATA | GTG | GAG | TGG | ATA | GTC | TTC | CGG | AGA | 816 |
| Thr | Thr | Pro | Pro | Cys | Ser | Glu | Ile | Val | Glu | Trp | Ile | Val | Phe | Arg | Arg | |
| | | | 260 | | | | | 265 | | | | | 270 | | | |
| CCC | GTC | CCC | ATC | TCT | TAC | CAT | CAG | CTT | GAG | GCT | TTT | TAT | TCC | ATC | TTC | 864 |
| Pro | Val | Pro | Ile | Ser | Tyr | His | Gln | Leu | Glu | Ala | Phe | Tyr | Ser | Ile | Phe | |
| | | 275 | | | | | 280 | | | | | 285 | | | | |
| ACC | ACG | GAG | CAG | CAA | GAC | CAT | GTC | AAG | TCG | GTG | GAG | TAT | CTG | AGA | AAT | 912 |
| Thr | Thr | Glu | Gln | Gln | Asp | His | Val | Lys | Ser | Val | Glu | Tyr | Leu | Arg | Asn | |
| | 290 | | | | | 295 | | | | | 300 | | | | | |
| AAC | TTT | CGA | CCA | CAG | CAG | CGT | CTG | CAT | GAC | AGG | GTG | GTG | TCC | AAG | TCC | 960 |
| Asn | Phe | Arg | Pro | Gln | Gln | Arg | Leu | His | Asp | Arg | Val | Val | Ser | Lys | Ser | |
| 305 | | | | | 310 | | | | | 315 | | | | | 320 | |
| GCC | GTC | CGT | GAC | TCC | TGG | AAC | CAC | GAC | ATG | ACA | GAC | TTC | TTA | GAA | AAC | 1008 |
| Ala | Val | Arg | Asp | Ser | Trp | Asn | His | Asp | Met | Thr | Asp | Phe | Leu | Glu | Asn | |
| | | | | 325 | | | | | 330 | | | | | 335 | | |
| CCA | CTG | GGG | ACA | GAA | GCC | TCT | AAA | GTT | TGC | AGC | TCT | CCA | CCC | ATC | CAC | 1056 |
| Pro | Leu | Gly | Thr | Glu | Ala | Ser | Lys | Val | Cys | Ser | Ser | Pro | Pro | Ile | His | |
| | | | 340 | | | | | 345 | | | | | 350 | | | |
| ATG | AAG | GTG | CAG | CCT | CTG | AAC | CAG | ACG | GCA | CTG | CAG | GTG | TCC | TGG | AGC | 1104 |
| Met | Lys | Val | Gln | Pro | Leu | Asn | Gln | Thr | Ala | Leu | Gln | Val | Ser | Trp | Ser | |
| | | 355 | | | | | 360 | | | | | 365 | | | | |
| CAG | CCG | GAG | ACT | ATC | TAC | CAC | CCA | CCC | ATC | ATG | AAC | TAC | ATG | ATC | TCC | 1152 |
| Gln | Pro | Glu | Thr | Ile | Tyr | His | Pro | Pro | Ile | Met | Asn | Tyr | Met | Ile | Ser | |
| | 370 | | | | | 375 | | | | | 380 | | | | | |
| TAC | AGC | TGG | ACC | AAG | AAT | GAG | GAC | GAG | AAG | GAG | AAG | ACG | TTT | ACA | AAG | 1200 |
| Tyr | Ser | Trp | Thr | Lys | Asn | Glu | Asp | Glu | Lys | Glu | Lys | Thr | Phe | Thr | Lys | |
| 385 | | | | | 390 | | | | | 395 | | | | | 400 | |
| GAC | AGC | GAC | AAA | GAC | TTG | AAA | GCC | ACC | ATT | AGC | CAT | GTC | TCA | CCC | GAT | 1248 |
| Asp | Ser | Asp | Lys | Asp | Leu | Lys | Ala | Thr | Ile | Ser | His | Val | Ser | Pro | Asp | |
| | | | 405 | | | | | 410 | | | | | 415 | | | |
| AGC | CTT | TAC | CTG | TTC | CGA | GTC | CAG | GCC | GTG | TGT | CGG | AAC | GAC | ATG | CGC | 1296 |
| Ser | Leu | Tyr | Leu | Phe | Arg | Val | Gln | Ala | Val | Cys | Arg | Asn | Asp | Met | Arg | |
| | | | 420 | | | | | 425 | | | | | 430 | | | |
| AGC | GAC | TTT | AGC | CAG | ACG | ATG | CTG | TTT | CAA | GCT | AAT | ACC | ACT | CGA | ATA | 1344 |
| Ser | Asp | Phe | Ser | Gln | Thr | Met | Leu | Phe | Gln | Ala | Asn | Thr | Thr | Arg | Ile | |
| | | 435 | | | | | 440 | | | | | 445 | | | | |
| TTC | CAA | GGG | ACC | AGA | ATA | GTG | AAA | ACA | GGA | GTG | CCC | ACA | GCG | TCT | CCT | 1392 |
| Phe | Gln | Gly | Thr | Arg | Ile | Val | Lys | Thr | Gly | Val | Pro | Thr | Ala | Ser | Pro | |
| | 450 | | | | | 455 | | | | | 460 | | | | | |
| GCC | TCT | TCA | GCC | GAC | ATG | GCC | CCC | ATC | AGC | TCG | GGG | TCT | TCT | ACC | TGG | 1440 |
| Ala | Ser | Ser | Ala | Asp | Met | Ala | Pro | Ile | Ser | Ser | Gly | Ser | Ser | Thr | Trp | |

-continued

| | | | | | | | | | | | | | | | | |
|---|---|---|---|---|---|---|---|---|---|---|---|---|---|---|---|---|
| Ala | Ser | Ser | Ala | Asp | Met | Ala | Pro | Ile | Ser | Ser | Gly | Ser | Ser | Thr | Trp | |
| 465 | | | | 470 | | | | | 475 | | | | | 480 | | |

| ACG | TCC | TCT | GGC | ATC | CCA | TTC | TCA | TTT | GTT | TCC | ATG | GCA | ACT | GGG | ATG | 1488 |
|---|---|---|---|---|---|---|---|---|---|---|---|---|---|---|---|---|
| Thr | Ser | Ser | Gly | Ile | Pro | Phe | Ser | Phe | Val | Ser | Met | Ala | Thr | Gly | Met | |
| | | | | 485 | | | | | 490 | | | | | 495 | | |

| GGC | CCC | TCC | TCC | AGT | GGC | AGC | CAG | GCC | ACA | GTG | GCC | TCG | GTG | GTC | ACC | 1536 |
|---|---|---|---|---|---|---|---|---|---|---|---|---|---|---|---|---|
| Gly | Pro | Ser | Ser | Ser | Gly | Ser | Gln | Ala | Thr | Val | Ala | Ser | Val | Val | Thr | |
| | | | 500 | | | | | 505 | | | | | 510 | | | |

| AGC | ACG | CTG | CTC | GCC | GGC | CTG | GGG | TTC | GGC | GGT | GGT | GGC | ATC | TCC | TCT | 1584 |
|---|---|---|---|---|---|---|---|---|---|---|---|---|---|---|---|---|
| Ser | Thr | Leu | Leu | Ala | Gly | Leu | Gly | Phe | Gly | Gly | Gly | Gly | Ile | Ser | Ser | |
| | | 515 | | | | | 520 | | | | | 525 | | | | |

| TTC | CCC | AGC | ACT | GTG | TGG | CCC | ACG | CGC | CTC | CCG | ACG | GCC | GCC | TCA | GCC | 1632 |
|---|---|---|---|---|---|---|---|---|---|---|---|---|---|---|---|---|
| Phe | Pro | Ser | Thr | Val | Trp | Pro | Thr | Arg | Leu | Pro | Thr | Ala | Ala | Ser | Ala | |
| 530 | | | | | 535 | | | | | 540 | | | | | | |

| AGC | AAG | CAG | GCG | GCT | AGG | CCA | GTC | CTA | GCC | ACC | ACA | GAG | GCC | TTG | GCT | 1680 |
|---|---|---|---|---|---|---|---|---|---|---|---|---|---|---|---|---|
| Ser | Lys | Gln | Ala | Ala | Arg | Pro | Val | Leu | Ala | Thr | Glu | Ala | Leu | Ala | | |
| 545 | | | | | 550 | | | | | 555 | | | | | 560 | |

| TCT | CCA | GGG | CCC | GAT | GGT | GAT | TCG | TCA | CCA | ACC | AAG | GAC | GGC | GAG | GGC | 1728 |
|---|---|---|---|---|---|---|---|---|---|---|---|---|---|---|---|---|
| Ser | Pro | Gly | Pro | Asp | Gly | Asp | Ser | Ser | Pro | Thr | Lys | Asp | Gly | Glu | Gly | |
| | | | | 565 | | | | | 570 | | | | | 575 | | |

| ACC | GAG | GAA | GGA | GAG | AAG | GAT | GAG | AAA | AGC | GAG | AGT | GAG | GAT | GGG | GAG | 1776 |
|---|---|---|---|---|---|---|---|---|---|---|---|---|---|---|---|---|
| Thr | Glu | Glu | Gly | Glu | Lys | Asp | Glu | Lys | Ser | Glu | Ser | Glu | Asp | Gly | Glu | |
| | | | 580 | | | | | 585 | | | | | 590 | | | |

| CGG | GAG | CAC | GAG | GAG | GAT | GGA | GAG | AAG | GAC | TCC | GAA | AAG | AAG | GAG | AAG | 1824 |
|---|---|---|---|---|---|---|---|---|---|---|---|---|---|---|---|---|
| Arg | Glu | His | Glu | Glu | Asp | Gly | Glu | Lys | Asp | Ser | Glu | Lys | Lys | Glu | Lys | |
| | | 595 | | | | | 600 | | | | | 605 | | | | |

| AGT | GGG | GTG | ACC | CAC | GCT | GCC | GAG | GAG | CGG | AAT | CAG | ACG | GAG | CCC | AGC | 1872 |
|---|---|---|---|---|---|---|---|---|---|---|---|---|---|---|---|---|
| Ser | Gly | Val | Thr | His | Ala | Ala | Glu | Glu | Arg | Asn | Gln | Thr | Glu | Pro | Ser | |
| 610 | | | | | 615 | | | | | 620 | | | | | | |

| CCC | ACA | CCC | TCG | TCT | CCT | AAC | AGG | ACT | GCC | GAG | GGA | GGG | CAT | CAG | ACT | 1920 |
|---|---|---|---|---|---|---|---|---|---|---|---|---|---|---|---|---|
| Pro | Thr | Pro | Ser | Ser | Pro | Asn | Arg | Thr | Ala | Glu | Gly | Gly | His | Gln | Thr | |
| 625 | | | | | 630 | | | | | 635 | | | | | 640 | |

| ATA | CCT | GGG | CAT | GAG | CAG | GAT | CAC | ACT | GCC | GTC | CCC | ACA | GAC | CAG | ACG | 1968 |
|---|---|---|---|---|---|---|---|---|---|---|---|---|---|---|---|---|
| Ile | Pro | Gly | His | Glu | Gln | Asp | His | Thr | Ala | Val | Pro | Thr | Asp | Gln | Thr | |
| | | | | 645 | | | | | 650 | | | | | 655 | | |

| GGC | GGA | AGG | AGG | GAT | GCC | GGC | CCA | GGC | CTG | GAC | CCC | GAC | ATG | GTC | ACC | 2016 |
|---|---|---|---|---|---|---|---|---|---|---|---|---|---|---|---|---|
| Gly | Gly | Arg | Arg | Asp | Ala | Gly | Pro | Gly | Leu | Asp | Pro | Asp | Met | Val | Thr | |
| | | | 660 | | | | | 665 | | | | | 670 | | | |

| TCC | ACC | CAA | GTG | CCC | CCC | ACC | GCC | ACA | GAG | GAG | CAG | TAT | GCA | GGG | AGT | 2064 |
|---|---|---|---|---|---|---|---|---|---|---|---|---|---|---|---|---|
| Ser | Thr | Gln | Val | Pro | Pro | Thr | Ala | Thr | Glu | Glu | Gln | Tyr | Ala | Gly | Ser | |
| | | 675 | | | | | 680 | | | | | 685 | | | | |

| GAT | CCC | AAG | AGG | CCC | GAA | ATG | CCA | TCT | AAA | AAG | CCT | ATG | TCC | CGC | GGG | 2112 |
|---|---|---|---|---|---|---|---|---|---|---|---|---|---|---|---|---|
| Asp | Pro | Lys | Arg | Pro | Glu | Met | Pro | Ser | Lys | Lys | Pro | Met | Ser | Arg | Gly | |
| | | 690 | | | | | 695 | | | | | 700 | | | | |

| GAC | CGA | TTT | TCT | GAA | GAC | AGC | AGA | TTT | ATC | ACT | GTT | AAT | CCA | GCG | GAA | 2160 |
|---|---|---|---|---|---|---|---|---|---|---|---|---|---|---|---|---|
| Asp | Arg | Phe | Ser | Glu | Asp | Ser | Arg | Phe | Ile | Thr | Val | Asn | Pro | Ala | Glu | |
| 705 | | | | | 710 | | | | | 715 | | | | | 720 | |

| AAA | AAC | ACC | TCT | GGA | ATG | ATA | AGC | CGC | CCT | GCT | CCA | GGG | AGG | ATG | GAG | 2208 |
|---|---|---|---|---|---|---|---|---|---|---|---|---|---|---|---|---|
| Lys | Asn | Thr | Ser | Gly | Met | Ile | Ser | Arg | Pro | Ala | Pro | Gly | Arg | Met | Glu | |
| | | | | 725 | | | | | 730 | | | | | 735 | | |

| TGG | ATC | ATC | CCT | CTG | ATT | GTG | GTA | TCA | GCC | TTG | ACC | TTC | GTG | TGC | CTC | 2256 |
|---|---|---|---|---|---|---|---|---|---|---|---|---|---|---|---|---|
| Trp | Ile | Ile | Pro | Leu | Ile | Val | Val | Ser | Ala | Leu | Thr | Phe | Val | Cys | Leu | |
| | | | 740 | | | | | 745 | | | | | 750 | | | |

| ATC | CTT | CTC | ATT | GCT | GTG | CTC | GTT | TAC | TGG | AGA | GGG | TGT | AAC | AAA | ATA | 2304 |
|---|---|---|---|---|---|---|---|---|---|---|---|---|---|---|---|---|
| Ile | Leu | Leu | Ile | Ala | Val | Leu | Val | Tyr | Trp | Arg | Gly | Cys | Asn | Lys | Ile | |
| | | 755 | | | | | 760 | | | | | 765 | | | | |

| AAG | TCC | AAG | GGC | TTT | CCC | AGA | CGT | TTC | CGT | GAA | GTG | CCT | TCT | TCT | GGG | 2352 |
|---|---|---|---|---|---|---|---|---|---|---|---|---|---|---|---|---|
| Lys | Ser | Lys | Gly | Phe | Pro | Arg | Arg | Phe | Arg | Glu | Val | Pro | Ser | Ser | Gly | |
| 770 | | | | | 775 | | | | | 780 | | | | | | |

| GAG | AGA | GGA | GAG | AAG | GGG | AGC | AGA | AAA | TGT | TTT | CAG | ACT | GCT | CAT | TTC | 2400 |

|  |  |  |  |  |  |  |  |  |  |  |  |  |  |  |  |
|---|---|---|---|---|---|---|---|---|---|---|---|---|---|---|---|
| Glu | Arg | Gly | Glu | Lys | Gly | Ser | Arg | Lys | Cys | Phe | Gln | Thr | Ala | His | Phe |
| 785 |  |  |  | 790 |  |  |  | 795 |  |  |  |  |  |  | 800 |

| TAT | GTG | GAA | GAC | AGC | AGT | TCA | CCT | CGA | GTG | GTC | CCT | AAT | GAA | AGT | ATT | 2448 |
|---|---|---|---|---|---|---|---|---|---|---|---|---|---|---|---|---|
| Tyr | Val | Glu | Asp | Ser | Ser | Ser | Pro | Arg | Val | Val | Pro | Asn | Glu | Ser | Ile |  |
|  |  |  |  | 805 |  |  |  |  | 810 |  |  |  |  | 815 |  |  |

| CCT | ATT | ATT | CCT | ATT | CCG | GAT | GAC | ATG | GAA | GCC | ATT | CCT | GTC | AAA | CAG | 2496 |
|---|---|---|---|---|---|---|---|---|---|---|---|---|---|---|---|---|
| Pro | Ile | Ile | Pro | Ile | Pro | Asp | Asp | Met | Glu | Ala | Ile | Pro | Val | Lys | Gln |  |
|  |  |  | 820 |  |  |  |  | 825 |  |  |  |  | 830 |  |  |  |

| TTT | GTC | AAA | CAC | ATC | GGT | GAG | CTC | TAT | TCT | AAT | AAC | CAG | CAT | GGG | TTC | 2544 |
|---|---|---|---|---|---|---|---|---|---|---|---|---|---|---|---|---|
| Phe | Val | Lys | His | Ile | Gly | Glu | Leu | Tyr | Ser | Asn | Asn | Gln | His | Gly | Phe |  |
|  |  | 835 |  |  |  |  | 840 |  |  |  |  | 845 |  |  |  |  |

| TCT | GAG | GAT | TTT | GAG | GAA | GTC | CAG | CGC | TGT | ACT | GCT | GAT | ATG | AAC | ATC | 2592 |
|---|---|---|---|---|---|---|---|---|---|---|---|---|---|---|---|---|
| Ser | Glu | Asp | Phe | Glu | Glu | Val | Gln | Arg | Cys | Thr | Ala | Asp | Met | Asn | Ile |  |
|  | 850 |  |  |  |  | 855 |  |  |  |  | 860 |  |  |  |  |  |

| ACT | GCA | GAG | CAT | TCC | AAT | CAT | CCA | GAA | AAC | AAG | CAC | AAA | AAC | AGA | TAC | 2640 |
|---|---|---|---|---|---|---|---|---|---|---|---|---|---|---|---|---|
| Thr | Ala | Glu | His | Ser | Asn | His | Pro | Glu | Asn | Lys | His | Lys | Asn | Arg | Tyr |  |
| 865 |  |  |  |  | 870 |  |  |  |  | 875 |  |  |  |  | 880 |  |

| ATC | AAC | ATT | TTA | GCA | TAT | GAT | CAC | AGT | AGG | GTG | AAG | TTA | AGA | CCT | TTA | 2688 |
|---|---|---|---|---|---|---|---|---|---|---|---|---|---|---|---|---|
| Ile | Asn | Ile | Leu | Ala | Tyr | Asp | His | Ser | Arg | Val | Lys | Leu | Arg | Pro | Leu |  |
|  |  |  |  | 885 |  |  |  |  | 890 |  |  |  |  | 895 |  |  |

| CCA | GGA | AAA | GAC | TCT | AAG | CAC | AGC | GAC | TAC | ATT | AAT | GCA | AAC | TAT | GTT | 2736 |
|---|---|---|---|---|---|---|---|---|---|---|---|---|---|---|---|---|
| Pro | Gly | Lys | Asp | Ser | Lys | His | Ser | Asp | Tyr | Ile | Asn | Ala | Asn | Tyr | Val |  |
|  |  |  | 900 |  |  |  |  | 905 |  |  |  |  | 910 |  |  |  |

| GAT | GGT | TAC | AAC | AAA | GCA | AAA | GCC | TAC | ATT | GCC | ACC | CAA | GGA | CCT | TTG | 2784 |
|---|---|---|---|---|---|---|---|---|---|---|---|---|---|---|---|---|
| Asp | Gly | Tyr | Asn | Lys | Ala | Lys | Ala | Tyr | Ile | Ala | Thr | Gln | Gly | Pro | Leu |  |
|  |  | 915 |  |  |  |  | 920 |  |  |  |  | 925 |  |  |  |  |

| AAG | TCT | ACA | TTT | GAA | GAT | TTC | TGG | AGG | ATG | ATT | TGG | GAA | CAA | AAC | ACT | 2832 |
|---|---|---|---|---|---|---|---|---|---|---|---|---|---|---|---|---|
| Lys | Ser | Thr | Phe | Glu | Asp | Phe | Trp | Arg | Met | Ile | Trp | Glu | Gln | Asn | Thr |  |
|  | 930 |  |  |  |  | 935 |  |  |  |  | 940 |  |  |  |  |  |

| GGA | ATC | ATT | GTG | ATG | ATT | ACG | AAC | CTT | GTG | GAA | AAA | GGA | AGA | CGA | AAA | 2880 |
|---|---|---|---|---|---|---|---|---|---|---|---|---|---|---|---|---|
| Gly | Ile | Ile | Val | Met | Ile | Thr | Asn | Leu | Val | Glu | Lys | Gly | Arg | Arg | Lys |  |
| 945 |  |  |  |  | 950 |  |  |  |  | 955 |  |  |  |  | 960 |  |

| TGT | GAT | CAG | TAT | TGG | CCA | ACA | GAG | AAC | AGT | GAG | GAA | TAT | GGA | AAC | ATT | 2928 |
|---|---|---|---|---|---|---|---|---|---|---|---|---|---|---|---|---|
| Cys | Asp | Gln | Tyr | Trp | Pro | Thr | Glu | Asn | Ser | Glu | Glu | Tyr | Gly | Asn | Ile |  |
|  |  |  |  | 965 |  |  |  |  | 970 |  |  |  |  | 975 |  |  |

| ATT | GTC | ACG | CTG | AAG | AGC | ACA | AAA | ATA | CAT | GCC | TGC | TAC | ACT | GTT | CGT | 2976 |
|---|---|---|---|---|---|---|---|---|---|---|---|---|---|---|---|---|
| Ile | Val | Thr | Leu | Lys | Ser | Thr | Lys | Ile | His | Ala | Cys | Tyr | Thr | Val | Arg |  |
|  |  |  | 980 |  |  |  |  | 985 |  |  |  |  | 990 |  |  |  |

| CGT | TTT | TCA | ATC | AGA | AAT | ACA | AAA | GTG | AAA | AAG | GGT | CAG | AAG | GGA | AAT | 3024 |
|---|---|---|---|---|---|---|---|---|---|---|---|---|---|---|---|---|
| Arg | Phe | Ser | Ile | Arg | Asn | Thr | Lys | Val | Lys | Lys | Gly | Gln | Lys | Gly | Asn |  |
|  |  | 995 |  |  |  |  | 1000 |  |  |  |  | 1005 |  |  |  |  |

| CCC | AAG | GGT | CGT | CAG | AAT | GAA | AGG | GTA | GTG | ATC | CAG | TAT | CAC | TAT | ACA | 3072 |
|---|---|---|---|---|---|---|---|---|---|---|---|---|---|---|---|---|
| Pro | Lys | Gly | Arg | Gln | Asn | Glu | Arg | Val | Val | Ile | Gln | Tyr | His | Tyr | Thr |  |
|  | 1010 |  |  |  |  | 1015 |  |  |  |  | 1020 |  |  |  |  |  |

| CAG | TGG | CCT | GAC | ATG | GGA | GTT | CCC | GAG | TAT | GCC | CTT | CCA | GTA | CTG | ACT | 3120 |
|---|---|---|---|---|---|---|---|---|---|---|---|---|---|---|---|---|
| Gln | Trp | Pro | Asp | Met | Gly | Val | Pro | Glu | Tyr | Ala | Leu | Pro | Val | Leu | Thr |  |
| 1025 |  |  |  |  | 1030 |  |  |  |  | 1035 |  |  |  |  | 1040 |  |

| TTC | GTG | AGG | AGA | TCC | TCA | GCA | GCT | CGG | ATG | CCA | GAA | ACG | GGC | CCT | GTG | 3168 |
|---|---|---|---|---|---|---|---|---|---|---|---|---|---|---|---|---|
| Phe | Val | Arg | Arg | Ser | Ser | Ala | Ala | Arg | Met | Pro | Glu | Thr | Gly | Pro | Val |  |
|  |  |  |  | 1045 |  |  |  |  | 1050 |  |  |  |  | 1055 |  |  |

| TTG | GTG | CAC | TGC | AGT | GCT | GGT | GTG | GGC | AGA | ACA | GGC | ACC | TAT | ATT | GTA | 3216 |
|---|---|---|---|---|---|---|---|---|---|---|---|---|---|---|---|---|
| Leu | Val | His | Cys | Ser | Ala | Gly | Val | Gly | Arg | Thr | Gly | Thr | Tyr | Ile | Val |  |
|  |  |  | 1060 |  |  |  |  | 1065 |  |  |  |  | 1070 |  |  |  |

| ATA | GAC | AGC | ATG | CTG | CAA | CAG | ATA | AAA | GAC | AAA | AGC | ACA | GTT | AAC | GTC | 3264 |
|---|---|---|---|---|---|---|---|---|---|---|---|---|---|---|---|---|
| Ile | Asp | Ser | Met | Leu | Gln | Gln | Ile | Lys | Asp | Lys | Ser | Thr | Val | Asn | Val |  |
|  |  |  | 1075 |  |  |  |  | 1080 |  |  |  |  | 1085 |  |  |  |

| CTG | GGA | TTC | CTG | AAG | CAT | ATC | AGG | ACA | CAG | CGT | AAC | TAC | CTC | GTC | CAG | 3312 |
|---|---|---|---|---|---|---|---|---|---|---|---|---|---|---|---|---|
| Leu | Gly | Phe | Leu | Lys | His | Ile | Arg | Thr | Gln | Arg | Asn | Tyr | Leu | Val | Gln |  |
|  |  | 1090 |  |  |  |  | 1095 |  |  |  |  | 1100 |  |  |  |  |

| ACT | GAG | GAG | CAG | TAC | ATT | TTC | ATC | CAT | GAT | GCC | TTG | TTG | GAA | GCC | ATT | 3360 |

| | | | | | | | | | | | | | | | | |
|---|---|---|---|---|---|---|---|---|---|---|---|---|---|---|---|---|
| Thr | Glu | Glu | Gln | Tyr | Ile | Phe | Ile | His | Asp | Ala | Leu | Leu | Glu | Ala | Ile | |
| 1105 | | | | 1110 | | | | 1115 | | | | 1120 | | | | |

| | | | | | | | | | | | | | | | | |
|---|---|---|---|---|---|---|---|---|---|---|---|---|---|---|---|---|
| CTT | GGA | AAG | GAG | ACT | GAA | GTA | TCT | TCA | AAT | CAG | CTG | CAC | AGC | TAT | GTT | 3408 |
| Leu | Gly | Lys | Glu | Thr | Glu | Val | Ser | Ser | Asn | Gln | Leu | His | Ser | Tyr | Val | |
| | | | | 1125 | | | | | 1130 | | | | | 1135 | | |
| AAC | AGC | ATC | CTT | ATA | CCA | GGA | GTA | GGA | GGA | AAG | ACA | CGA | CTG | GAA | AAG | 3456 |
| Asn | Ser | Ile | Leu | Ile | Pro | Gly | Val | Gly | Gly | Lys | Thr | Arg | Leu | Glu | Lys | |
| | | | 1140 | | | | | 1145 | | | | | 1150 | | | |
| CAA | TTC | AAG | CTG | GTC | ACA | CAG | TGT | AAT | GCA | AAA | TAT | GTG | GAA | TGT | TTC | 3504 |
| Gln | Phe | Lys | Leu | Val | Thr | Gln | Cys | Asn | Ala | Lys | Tyr | Val | Glu | Cys | Phe | |
| | | 1155 | | | | | 1160 | | | | | 1165 | | | | |
| AGT | GCT | CAG | AAA | GAG | TGT | AAC | AAA | GAA | AAG | AAC | AGA | AAC | TCT | TCA | GTT | 3552 |
| Ser | Ala | Gln | Lys | Glu | Cys | Asn | Lys | Glu | Lys | Asn | Arg | Asn | Ser | Ser | Val | |
| | | 1170 | | | | | 1175 | | | | | 1180 | | | | |
| GTG | CCA | TCT | GAG | CGT | GCT | CGA | GTG | GGT | CTT | GCA | CCA | TTG | CCT | GGA | ATG | 3600 |
| Val | Pro | Ser | Glu | Arg | Ala | Arg | Val | Gly | Leu | Ala | Pro | Leu | Pro | Gly | Met | |
| 1185 | | | | | 1190 | | | | | 1195 | | | | | 1200 | |
| AAA | GGA | ACA | GAT | TAC | ATT | AAT | GCT | TCT | TAT | ATC | ATG | GGC | TAT | TAT | AGG | 3648 |
| Lys | Gly | Thr | Asp | Tyr | Ile | Asn | Ala | Ser | Tyr | Ile | Met | Gly | Tyr | Tyr | Arg | |
| | | | | 1205 | | | | | 1210 | | | | | 1215 | | |
| AGC | AAT | GAA | TTT | ATT | ATA | ACT | CAG | CAT | CCT | CTG | CCA | CAT | ACT | ACG | AAA | 3696 |
| Ser | Asn | Glu | Phe | Ile | Ile | Thr | Gln | His | Pro | Leu | Pro | His | Thr | Thr | Lys | |
| | | | 1220 | | | | | 1225 | | | | | 1230 | | | |
| GAT | TTC | TGG | CGA | ATG | ATT | TGG | GAT | CAT | AAC | GCA | CAG | ATC | ATT | GTC | ATG | 3744 |
| Asp | Phe | Trp | Arg | Met | Ile | Trp | Asp | His | Asn | Ala | Gln | Ile | Ile | Val | Met | |
| | | 1235 | | | | | 1240 | | | | | 1245 | | | | |
| CTG | CCA | GAC | AAC | CAG | AGC | TTG | GCA | GAA | GAT | GAG | TTT | GTG | TAC | TGG | CCA | 3792 |
| Leu | Pro | Asp | Asn | Gln | Ser | Leu | Ala | Glu | Asp | Glu | Phe | Val | Tyr | Trp | Pro | |
| | 1250 | | | | | 1255 | | | | | 1260 | | | | | |
| AGT | CGA | GAA | GAA | TCC | ATG | AAC | TGT | GAG | GCC | TTT | ACC | GTC | ACC | CTT | ATC | 3840 |
| Ser | Arg | Glu | Glu | Ser | Met | Asn | Cys | Glu | Ala | Phe | Thr | Val | Thr | Leu | Ile | |
| 1265 | | | | | 1270 | | | | | 1275 | | | | | 1280 | |
| AGC | AAA | GAC | AGA | CTG | TGC | CTC | TCT | AAT | GAA | GAA | CAA | ATT | ATC | ATC | CAT | 3888 |
| Ser | Lys | Asp | Arg | Leu | Cys | Leu | Ser | Asn | Glu | Glu | Gln | Ile | Ile | Ile | His | |
| | | | | 1285 | | | | | 1290 | | | | | 1295 | | |
| GAC | TTT | ATC | CTT | GAA | GCT | ACA | CAG | GAT | GAC | TAT | GTC | TTA | GAA | GTT | CGG | 3936 |
| Asp | Phe | Ile | Leu | Glu | Ala | Thr | Gln | Asp | Asp | Tyr | Val | Leu | Glu | Val | Arg | |
| | | | 1300 | | | | | 1305 | | | | | 1310 | | | |
| CAC | TTT | CAG | TGT | CCC | AAA | TGG | CCT | AAC | CCA | GAT | GCC | CCC | ATA | AGT | AGT | 3984 |
| His | Phe | Gln | Cys | Pro | Lys | Trp | Pro | Asn | Pro | Asp | Ala | Pro | Ile | Ser | Ser | |
| | | 1315 | | | | | 1320 | | | | | 1325 | | | | |
| ACC | TTT | GAA | CTT | ATC | AAC | GTC | ATC | AAG | GAA | GAG | GCC | TTA | ACA | AGG | GAT | 4032 |
| Thr | Phe | Glu | Leu | Ile | Asn | Val | Ile | Lys | Glu | Glu | Ala | Leu | Thr | Arg | Asp | |
| | 1330 | | | | | 1335 | | | | | 1340 | | | | | |
| GGT | CCC | ACC | ATT | GTT | CAT | GAT | GAG | TAT | GGA | GCA | GTT | TCA | GCA | GGA | ATG | 4080 |
| Gly | Pro | Thr | Ile | Val | His | Asp | Glu | Tyr | Gly | Ala | Val | Ser | Ala | Gly | Met | |
| 1345 | | | | | 1350 | | | | | 1355 | | | | | 1360 | |
| TTA | TGT | GCC | CTT | ACC | ACC | CTG | TCC | CAG | CAA | CTG | GAG | AAT | GAA | AAT | GCT | 4128 |
| Leu | Cys | Ala | Leu | Thr | Thr | Leu | Ser | Gln | Gln | Leu | Glu | Asn | Glu | Asn | Ala | |
| | | | | 1365 | | | | | 1370 | | | | | 1375 | | |
| GTG | GAT | GTT | TTC | CAG | GTT | GCA | AAA | ATG | ATC | AAT | CTT | ATG | AGG | CCT | GGA | 4176 |
| Val | Asp | Val | Phe | Gln | Val | Ala | Lys | Met | Ile | Asn | Leu | Met | Arg | Pro | Gly | |
| | | | 1380 | | | | | 1385 | | | | | 1390 | | | |
| GTA | TTC | ACA | GAC | ATT | GAA | CAA | TAC | CAG | TTC | ATC | TAT | AAA | GCA | AGG | CTT | 4224 |
| Val | Phe | Thr | Asp | Ile | Glu | Gln | Tyr | Gln | Phe | Ile | Tyr | Lys | Ala | Arg | Leu | |
| | | 1395 | | | | | 1400 | | | | | 1405 | | | | |
| AGC | TTG | GTC | AGC | ACT | AAA | GAA | AAT | GGA | AAT | GGT | CCC | ATG | ACA | GTA | GAC | 4272 |
| Ser | Leu | Val | Ser | Thr | Lys | Glu | Asn | Gly | Asn | Gly | Pro | Met | Thr | Val | Asp | |
| | 1410 | | | | | 1415 | | | | | 1420 | | | | | |
| AAA | AAT | GGT | GCT | GTT | CTT | ATT | GCA | GAT | GAA | TCA | GAC | CCT | GCT | GAG | AGC | 4320 |

```
Lys  Asn  Gly  Ala  Val  Leu  Ile  Ala  Asp  Glu  Ser  Asp  Pro  Ala  Glu  Ser
1425                1430                1435                     1440

ATG  GAG  TCC  CTA  GTG  TGA                                                          4338
Met  Glu  Ser  Leu  Val
                    1445
```

( 2 ) INFORMATION FOR SEQ ID NO:2:

( i ) SEQUENCE CHARACTERISTICS:
        ( A ) LENGTH: 1445 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Arg  Leu  Leu  Glu  Pro  Cys  Trp  Trp  Ile  Leu  Phe  Leu  Lys  Ile
 1                   5                   10                           15

Thr  Ser  Ser  Val  Leu  His  Tyr  Val  Val  Cys  Phe  Pro  Ala  Leu  Thr  Glu
               20                   25                        30

Gly  Tyr  Val  Gly  Ala  Leu  His  Glu  Asn  Arg  His  Gly  Ser  Ala  Val  Gln
          35                   40                        45

Ile  Arg  Arg  Arg  Lys  Ala  Ser  Gly  Asp  Pro  Tyr  Trp  Ala  Tyr  Ser  Gly
     50                   55                        60

Ala  Tyr  Gly  Pro  Glu  His  Trp  Val  Thr  Ser  Ser  Val  Ser  Cys  Gly  Ser
65                   70                        75                            80

Arg  His  Gln  Ser  Pro  Ile  Asp  Ile  Leu  Asp  Gln  Tyr  Ala  Arg  Val  Gly
               85                        90                             95

Glu  Glu  Tyr  Gln  Glu  Leu  Gln  Leu  Asp  Gly  Phe  Asp  Asn  Glu  Ser  Ser
               100                      105                      110

Asn  Lys  Thr  Trp  Met  Lys  Asn  Thr  Gly  Lys  Thr  Val  Ala  Ile  Leu  Leu
          115                      120                      125

Lys  Asp  Asp  Tyr  Phe  Val  Ser  Gly  Ala  Gly  Leu  Pro  Gly  Arg  Phe  Lys
     130                      135                      140

Ala  Glu  Lys  Val  Glu  Phe  His  Trp  Gly  His  Ser  Asn  Gly  Ser  Ala  Gly
145                      150                      155                        160

Ser  Glu  His  Ser  Ile  Asn  Gly  Arg  Arg  Phe  Pro  Val  Glu  Met  Gln  Ile
               165                      170                      175

Phe  Phe  Tyr  Asn  Pro  Asp  Asp  Phe  Asp  Ser  Phe  Gln  Thr  Ala  Ile  Ser
               180                      185                      190

Glu  Asn  Arg  Ile  Ile  Gly  Ala  Met  Ala  Ile  Phe  Phe  Gln  Val  Ser  Pro
          195                      200                      205

Arg  Asp  Asn  Ser  Ala  Leu  Asp  Pro  Ile  Ile  His  Gly  Leu  Lys  Gly  Val
     210                      215                      220

Val  His  His  Glu  Lys  Glu  Thr  Phe  Leu  Asp  Pro  Phe  Val  Leu  Arg  Asp
225                      230                      235                        240

Leu  Leu  Pro  Ala  Ser  Leu  Gly  Ser  Tyr  Tyr  Arg  Tyr  Thr  Gly  Ser  Leu
               245                      250                      255

Thr  Thr  Pro  Pro  Cys  Ser  Glu  Ile  Val  Glu  Trp  Ile  Val  Phe  Arg  Arg
               260                      265                      270

Pro  Val  Pro  Ile  Ser  Tyr  His  Gln  Leu  Glu  Ala  Phe  Tyr  Ser  Ile  Phe
          275                      280                      285

Thr  Thr  Glu  Gln  Gln  Asp  His  Val  Lys  Ser  Val  Glu  Tyr  Leu  Arg  Asn
          290                      295                      300

Asn  Phe  Arg  Pro  Gln  Gln  Arg  Leu  His  Asp  Arg  Val  Val  Ser  Lys  Ser
305                      310                      315                        320

Ala  Val  Arg  Asp  Ser  Trp  Asn  His  Asp  Met  Thr  Asp  Phe  Leu  Glu  Asn
```

|     |     |     |     |     | 325 |     |     |     |     | 330 |     |     |     |     | 335 |     |
| --- | --- | --- | --- | --- | --- | --- | --- | --- | --- | --- | --- | --- | --- | --- | --- | --- |
| Pro | Leu | Gly | Thr 340 | Glu | Ala | Ser | Lys | Val 345 | Cys | Ser | Ser | Pro | Pro 350 | Ile | His |
| Met | Lys | Val 355 | Gln | Pro | Leu | Asn | Gln 360 | Thr | Ala | Leu | Gln | Val 365 | Ser | Trp | Ser |
| Gln | Pro | Glu 370 | Thr | Ile | Tyr | His 375 | Pro | Pro | Ile | Met | Asn 380 | Tyr | Met | Ile | Ser |
| Tyr 385 | Ser | Trp | Thr | Lys | Asn 390 | Glu | Asp | Glu | Lys | Glu 395 | Lys | Thr | Phe | Thr | Lys 400 |
| Asp | Ser | Asp | Lys | Asp 405 | Leu | Lys | Ala | Thr | Ile 410 | Ser | His | Val | Ser | Pro 415 | Asp |
| Ser | Leu | Tyr | Leu 420 | Phe | Arg | Val | Gln | Ala 425 | Val | Cys | Arg | Asn | Asp 430 | Met | Arg |
| Ser | Asp | Phe 435 | Ser | Gln | Thr | Met | Leu 440 | Phe | Gln | Ala | Asn | Thr 445 | Thr | Arg | Ile |
| Phe | Gln | Gly 450 | Thr | Arg | Ile | Val | Lys 455 | Thr | Gly | Val | Pro 460 | Thr | Ala | Ser | Pro |
| Ala | Ser 465 | Ser | Ala | Asp | Met 470 | Ala | Pro | Ile | Ser | Ser 475 | Gly | Ser | Ser | Thr | Trp 480 |
| Thr | Ser | Ser | Gly | Ile 485 | Pro | Phe | Ser | Phe | Val 490 | Ser | Met | Ala | Thr | Gly 495 | Met |
| Gly | Pro | Ser | Ser 500 | Ser | Gly | Ser | Gln | Ala 505 | Thr | Val | Ala | Ser | Val 510 | Val | Thr |
| Ser | Thr | Leu | Leu 515 | Ala | Gly | Leu | Gly 520 | Phe | Gly | Gly | Gly | Gly 525 | Ile | Ser | Ser |
| Phe | Pro 530 | Ser | Thr | Val | Trp | Pro 535 | Thr | Arg | Leu | Pro | Thr 540 | Ala | Ala | Ser | Ala |
| Ser 545 | Lys | Gln | Ala | Ala | Arg 550 | Pro | Val | Leu | Ala | Thr 555 | Thr | Glu | Ala | Leu | Ala 560 |
| Ser | Pro | Gly | Pro | Asp 565 | Gly | Asp | Ser | Ser | Pro 570 | Thr | Lys | Asp | Gly | Glu 575 | Gly |
| Thr | Glu | Glu | Gly 580 | Glu | Lys | Asp | Glu | Lys 585 | Ser | Glu | Ser | Glu | Asp 590 | Gly | Glu |
| Arg | Glu | His 595 | Glu | Glu | Asp | Gly | Glu 600 | Lys | Asp | Ser | Glu | Lys 605 | Lys | Glu | Lys |
| Ser | Gly 610 | Val | Thr | His | Ala | Ala 615 | Glu | Glu | Arg | Asn | Gln 620 | Thr | Glu | Pro | Ser |
| Pro 625 | Thr | Pro | Ser | Ser | Pro 630 | Asn | Arg | Thr | Ala | Glu 635 | Gly | Gly | His | Gln | Thr 640 |
| Ile | Pro | Gly | His | Glu 645 | Gln | Asp | His | Thr | Ala 650 | Val | Pro | Thr | Asp | Gln 655 | Thr |
| Gly | Gly | Arg | Arg 660 | Asp | Ala | Gly | Pro | Gly 665 | Leu | Asp | Pro | Asp | Met 670 | Val | Thr |
| Ser | Thr | Gln 675 | Val | Pro | Pro | Thr | Ala 680 | Thr | Glu | Glu | Gln | Tyr 685 | Ala | Gly | Ser |
| Asp | Pro 690 | Lys | Arg | Pro | Glu | Met 695 | Pro | Ser | Lys | Lys | Pro 700 | Met | Ser | Arg | Gly |
| Asp | Arg 705 | Phe | Ser | Glu | Asp | Ser 710 | Arg | Phe | Ile | Thr | Asn 715 | Val | Asn | Pro | Ala | Glu 720 |
| Lys | Asn | Thr | Ser | Gly 725 | Met | Ile | Ser | Arg | Pro 730 | Ala | Pro | Gly | Arg | Met 735 | Glu |
| Trp | Ile | Ile | Pro 740 | Leu | Ile | Val | Val | Ser 745 | Ala | Leu | Thr | Phe | Val 750 | Cys | Leu |

```
Ile Leu Leu Ile Ala Val Leu Val Tyr Trp Arg Gly Cys Asn Lys Ile
        755                 760                 765

Lys Ser Lys Gly Phe Pro Arg Arg Phe Arg Glu Val Pro Ser Ser Gly
        770                 775                 780

Glu Arg Gly Glu Lys Gly Ser Arg Lys Cys Phe Gln Thr Ala His Phe
785                     790                 795                 800

Tyr Val Glu Asp Ser Ser Ser Pro Arg Val Val Pro Asn Glu Ser Ile
                805                 810                 815

Pro Ile Ile Pro Ile Pro Asp Asp Met Glu Ala Ile Pro Val Lys Gln
            820                 825                 830

Phe Val Lys His Ile Gly Glu Leu Tyr Ser Asn Asn Gln His Gly Phe
        835                 840                 845

Ser Glu Asp Phe Glu Glu Val Gln Arg Cys Thr Ala Asp Met Asn Ile
    850                 855                 860

Thr Ala Glu His Ser Asn His Pro Glu Asn Lys His Lys Asn Arg Tyr
865                 870                 875                 880

Ile Asn Ile Leu Ala Tyr Asp His Ser Arg Val Lys Leu Arg Pro Leu
            885                 890                 895

Pro Gly Lys Asp Ser Lys His Ser Asp Tyr Ile Asn Ala Asn Tyr Val
            900                 905                 910

Asp Gly Tyr Asn Lys Ala Lys Ala Tyr Ile Ala Thr Gln Gly Pro Leu
        915                 920                 925

Lys Ser Thr Phe Glu Asp Phe Trp Arg Met Ile Trp Glu Gln Asn Thr
    930                 935                 940

Gly Ile Ile Val Met Ile Thr Asn Leu Val Glu Lys Gly Arg Arg Lys
945                 950                 955                 960

Cys Asp Gln Tyr Trp Pro Thr Glu Asn Ser Glu Glu Tyr Gly Asn Ile
                965                 970                 975

Ile Val Thr Leu Lys Ser Thr Lys Ile His Ala Cys Tyr Thr Val Arg
            980                 985                 990

Arg Phe Ser Ile Arg Asn Thr Lys Val Lys Lys Gly Gln Lys Gly Asn
        995                 1000                1005

Pro Lys Gly Arg Gln Asn Glu Arg Val Val Ile Gln Tyr His Tyr Thr
    1010                1015                1020

Gln Trp Pro Asp Met Gly Val Pro Glu Tyr Ala Leu Pro Val Leu Thr
1025                1030                1035                1040

Phe Val Arg Arg Ser Ser Ala Ala Arg Met Pro Glu Thr Gly Pro Val
            1045                1050                1055

Leu Val His Cys Ser Ala Gly Val Gly Arg Thr Gly Thr Tyr Ile Val
        1060                1065                1070

Ile Asp Ser Met Leu Gln Gln Ile Lys Asp Lys Ser Thr Val Asn Val
    1075                1080                1085

Leu Gly Phe Leu Lys His Ile Arg Thr Gln Arg Asn Tyr Leu Val Gln
    1090                1095                1100

Thr Glu Glu Gln Tyr Ile Phe Ile His Asp Ala Leu Leu Glu Ala Ile
1105                1110                1115                1120

Leu Gly Lys Glu Thr Glu Val Ser Ser Asn Gln Leu His Ser Tyr Val
            1125                1130                1135

Asn Ser Ile Leu Ile Pro Gly Val Gly Gly Lys Thr Arg Leu Glu Lys
            1140                1145                1150

Gln Phe Lys Leu Val Thr Gln Cys Asn Ala Lys Tyr Val Glu Cys Phe
    1155                1160                1165

Ser Ala Gln Lys Glu Cys Asn Lys Glu Lys Asn Arg Asn Ser Ser Val
    1170                1175                1180
```

| | | | | | | | | | | | | | | | |
|---|---|---|---|---|---|---|---|---|---|---|---|---|---|---|---|
| Val | Pro | Ser | Glu | Arg | Ala | Arg | Val | Gly | Leu | Ala | Pro | Leu | Pro | Gly | Met |
| 1185 | | | | 1190 | | | | 1195 | | | | | | 1200 | |
| Lys | Gly | Thr | Asp | Tyr | Ile | Asn | Ala | Ser | Tyr | Ile | Met | Gly | Tyr | Tyr | Arg |
| | | | | 1205 | | | | 1210 | | | | | 1215 | | |
| Ser | Asn | Glu | Phe | Ile | Ile | Thr | Gln | His | Pro | Leu | Pro | His | Thr | Thr | Lys |
| | | | | 1220 | | | | 1225 | | | | | 1230 | | |
| Asp | Phe | Trp | Arg | Met | Ile | Trp | Asp | His | Asn | Ala | Gln | Ile | Ile | Val | Met |
| | | | 1235 | | | | | 1240 | | | | 1245 | | | |
| Leu | Pro | Asp | Asn | Gln | Ser | Leu | Ala | Glu | Asp | Glu | Phe | Val | Tyr | Trp | Pro |
| | | 1250 | | | | 1255 | | | | 1260 | | | | | |
| Ser | Arg | Glu | Glu | Ser | Met | Asn | Cys | Glu | Ala | Phe | Thr | Val | Thr | Leu | Ile |
| 1265 | | | | | 1270 | | | | 1275 | | | | | | 1280 |
| Ser | Lys | Asp | Arg | Leu | Cys | Leu | Ser | Asn | Glu | Glu | Gln | Ile | Ile | Ile | His |
| | | | | 1285 | | | | | 1290 | | | | | 1295 | |
| Asp | Phe | Ile | Leu | Glu | Ala | Thr | Gln | Asp | Asp | Tyr | Val | Leu | Glu | Val | Arg |
| | | | | 1300 | | | | 1305 | | | | | 1310 | | |
| His | Phe | Gln | Cys | Pro | Lys | Trp | Pro | Asn | Pro | Asp | Ala | Pro | Ile | Ser | Ser |
| | | | 1315 | | | | 1320 | | | | | 1325 | | | |
| Thr | Phe | Glu | Leu | Ile | Asn | Val | Ile | Lys | Glu | Glu | Ala | Leu | Thr | Arg | Asp |
| | | | 1330 | | | | 1335 | | | | | 1340 | | | |
| Gly | Pro | Thr | Ile | Val | His | Asp | Glu | Tyr | Gly | Ala | Val | Ser | Ala | Gly | Met |
| 1345 | | | | | 1350 | | | | 1355 | | | | | | 1360 |
| Leu | Cys | Ala | Leu | Thr | Thr | Leu | Ser | Gln | Gln | Leu | Glu | Asn | Glu | Asn | Ala |
| | | | | 1365 | | | | 1370 | | | | | 1375 | | |
| Val | Asp | Val | Phe | Gln | Val | Ala | Lys | Met | Ile | Asn | Leu | Met | Arg | Pro | Gly |
| | | | 1380 | | | | | 1385 | | | | | 1390 | | |
| Val | Phe | Thr | Asp | Ile | Glu | Gln | Tyr | Gln | Phe | Ile | Tyr | Lys | Ala | Arg | Leu |
| | | | 1395 | | | | 1400 | | | | | 1405 | | | |
| Ser | Leu | Val | Ser | Thr | Lys | Glu | Asn | Gly | Asn | Gly | Pro | Met | Thr | Val | Asp |
| | | | 1410 | | | | 1415 | | | | | 1420 | | | |
| Lys | Asn | Gly | Ala | Val | Leu | Ile | Ala | Asp | Glu | Ser | Asp | Pro | Ala | Glu | Ser |
| 1425 | | | | | 1430 | | | | 1435 | | | | | | 1440 |
| Met | Glu | Ser | Leu | Val | | | | | | | | | | | |
| | | | | 1445 | | | | | | | | | | | |

( 2 ) INFORMATION FOR SEQ ID NO:3:

( i ) SEQUENCE CHARACTERISTICS:
        ( A ) LENGTH: 1442 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:3:

| | | | | | | | | | | | | | | | |
|---|---|---|---|---|---|---|---|---|---|---|---|---|---|---|---|
| Met | Arg | Arg | Leu | Leu | Glu | Pro | Cys | Trp | Trp | Ile | Leu | Phe | Leu | Lys | Ile |
| 1 | | | | 5 | | | | 10 | | | | | | 15 | |
| Thr | Ser | Ser | Val | Leu | His | Tyr | Val | Val | Cys | Phe | Pro | Ala | Leu | Thr | Glu |
| | | | 20 | | | | 25 | | | | | 30 | | | |
| Gly | Tyr | Val | Gly | Thr | Leu | Gln | Glu | Ser | Arg | Gln | Asp | Ser | Ser | Val | Gln |
| | | 35 | | | | 40 | | | | | 45 | | | | |
| Ile | Arg | Arg | Arg | Lys | Ala | Ser | Gly | Asp | Pro | Tyr | Trp | Ala | Tyr | Ser | Gly |
| | | 50 | | | | 55 | | | | | 60 | | | | |
| Ala | Tyr | Gly | Pro | Glu | His | Trp | Val | Thr | Ser | Ser | Val | Ser | Cys | Gly | Gly |
| 65 | | | | | 70 | | | | 75 | | | | | | 80 |

```
Ser  His  Gln  Ser  Pro  Ile  Asp  Ile  Leu  Asp  His  His  Ala  Arg  Val  Gly
               85                  90                            95
Asp  Glu  Tyr  Gln  Glu  Leu  Gln  Leu  Asp  Gly  Phe  Asp  Asn  Glu  Ser  Ser
              100                 105                      110
Asn  Lys  Thr  Trp  Met  Lys  Asn  Thr  Gly  Lys  Thr  Val  Ala  Ile  Leu  Leu
              115                 120                      125
Lys  Asp  Asp  Tyr  Phe  Val  Ser  Gly  Ala  Gly  Leu  Pro  Gly  Arg  Phe  Lys
     130                      135                      140
Ala  Glu  Lys  Val  Glu  Phe  His  Trp  Gly  His  Ser  Asn  Gly  Ser  Ala  Gly
145                      150                 155                           160
Ser  Glu  His  Ser  Val  Asn  Gly  Arg  Arg  Phe  Pro  Val  Glu  Met  Gln  Ile
              165                      170                      175
Phe  Phe  Tyr  Asn  Pro  Asp  Asp  Phe  Asp  Ser  Phe  Gln  Thr  Ala  Ile  Ser
              180                 185                           190
Glu  Asn  Arg  Ile  Ile  Gly  Ala  Met  Ala  Ile  Phe  Phe  Gln  Val  Ser  Pro
              195                 200                           205
Arg  Asp  Asn  Ser  Ala  Leu  Asp  Pro  Ile  Ile  His  Gly  Leu  Lys  Gly  Val
     210                      215                 220
Val  His  His  Glu  Lys  Glu  Thr  Phe  Leu  Asp  Pro  Phe  Ile  Leu  Arg  Asp
225                      230                 235                           240
Leu  Leu  Pro  Ala  Ser  Leu  Gly  Ser  Tyr  Tyr  Arg  Tyr  Thr  Gly  Ser  Leu
               245                      250                           255
Thr  Thr  Pro  Pro  Cys  Ser  Glu  Ile  Val  Glu  Trp  Ile  Val  Phe  Arg  Arg
               260                 265                      270
Pro  Val  Pro  Ile  Ser  Tyr  His  Gln  Leu  Glu  Ala  Phe  Tyr  Ser  Ile  Phe
               275                 280                      285
Thr  Thr  Glu  Gln  Gln  Asp  His  Val  Lys  Ser  Val  Glu  Tyr  Leu  Arg  Asn
     290                      295                 300
Asn  Phe  Arg  Pro  Gln  Gln  Ala  Leu  Asn  Asp  Arg  Val  Val  Ser  Lys  Ser
305                           310                 315                      320
Ala  Val  Arg  Asp  Ala  Trp  Asn  His  Asp  Leu  Ala  Asp  Phe  Leu  Asp  Asn
                    325                 330                           335
Pro  Leu  Gly  Thr  Glu  Ala  Ser  Lys  Val  Cys  Ser  Ser  Pro  Pro  Ile  His
               340                 345                      350
Met  Lys  Val  Gln  Pro  Leu  Asn  Gln  Thr  Ala  Leu  Gln  Val  Ser  Trp  Ser
          355                 360                      365
Gln  Pro  Glu  Thr  Ile  Tyr  His  Pro  Pro  Ile  Met  Asn  Tyr  Met  Ile  Ser
     370                      375                 380
Tyr  Ser  Trp  Thr  Lys  Asn  Glu  Asp  Glu  Lys  Glu  Lys  Thr  Phe  Thr  Lys
385                      390                 395                           400
Asp  Ser  Asp  Lys  Asp  Leu  Lys  Ala  Thr  Ile  Ser  His  Val  Ser  Pro  Asp
               405                 410                      415
Ser  Leu  Tyr  Leu  Phe  Arg  Val  Gln  Ala  Val  Cys  Arg  Asn  Asp  Met  Arg
               420                 425                      430
Ser  Asp  Phe  Ser  Gln  Thr  Met  Leu  Phe  Gln  Ala  Asn  Thr  Thr  Arg  Ile
               435                 440                      445
Phe  Gln  Gly  Thr  Arg  Ile  Val  Lys  Thr  Gly  Val  Pro  Thr  Ala  Ser  Pro
     450                      455                 460
Ala  Ser  Ser  Ala  Asp  Met  Ala  Pro  Ile  Ser  Ser  Gly  Ser  Ser  Thr  Trp
465                      470                      475                      480
Thr  Ser  Ser  Gly  Ile  Pro  Phe  Ser  Phe  Val  Ser  Met  Ala  Thr  Gly  Met
               485                      490                      495
Gly  Pro  Ser  Ser  Ser  Gly  Ser  Gln  Ala  Thr  Val  Ala  Ser  Val  Val  Thr
          500                      505                      510
```

```
Ser  Thr  Leu  Leu  Ala  Gly  Leu  Gly  Phe  Gly  Gly  Gly  Ile  Ser  Ser
          515            520                 525

Phe  Pro  Ser  Thr  Val  Trp  Pro  Thr  Arg  Leu  Pro  Thr  Ala  Ser  Ala  Ala
     530                 535                 540

Ser  Lys  Gln  Ala  Gly  Arg  Thr  Val  Leu  Ala  Thr  Thr  Glu  Ala  Leu  Ala
545                      550                 555                           560

Ser  Pro  Gly  Pro  Asp  Val  His  Ser  Ala  Pro  Ser  Lys  Asp  Ser  Glu  Gly
                    565                 570                      575

Thr  Glu  Glu  Gly  Glu  Lys  Glu  Glu  Lys  Ser  Glu  Ser  Glu  Asp  Gly  Glu
               580                 585                           590

Arg  Glu  His  Glu  Glu  Glu  Glu  Lys  Asp  Ser  Glu  Lys  Lys  Glu  Lys  Ser
          595                      600                      605

Glu  Ala  Thr  His  Thr  Ala  Ala  Glu  Ser  Asp  Arg  Thr  Ala  Pro  Ala  Pro
     610                      615                 620

Thr  Pro  Ser  Ser  Pro  His  Arg  Thr  Ala  Ala  Glu  Gly  Gly  His  Gln  Thr
625                      630                 635                           640

Ile  Pro  Gly  Arg  Arg  Gln  Asp  His  Ser  Ala  Pro  Ala  Thr  Asp  Gln  Pro
                    645                 650                      655

Gly  His  Val  Ala  Pro  Asp  Leu  Asp  Pro  Leu  Val  Asp  Thr  Ala  Thr  Gln
                    660                 665                      670

Val  Pro  Pro  Thr  Ala  Thr  Glu  Glu  His  Tyr  Ser  Gly  Ser  Asp  Pro  Arg
          675                      680                      685

Arg  Pro  Glu  Met  Pro  Ser  Lys  Lys  Pro  Met  Ser  Arg  Gly  Asp  Arg  Phe
     690                 695                      700

Ser  Glu  Asp  Ser  Lys  Phe  Ile  Thr  Val  Asn  Pro  Ala  Glu  Lys  Asn  Thr
705                      710                 715                           720

Ser  Gly  Met  Leu  Ser  Arg  Pro  Ser  Pro  Gly  Arg  Met  Glu  Trp  Ile  Ile
                    725                 730                      735

Pro  Leu  Ile  Val  Val  Ser  Ala  Leu  Thr  Phe  Val  Cys  Leu  Val  Leu  Leu
               740                 745                      750

Ile  Ala  Val  Leu  Val  Tyr  Trp  Arg  Gly  Cys  Asn  Lys  Ile  Lys  Ser  Lys
          755                      760                      765

Gly  Phe  Pro  Arg  Arg  Ser  Arg  Glu  Val  Pro  Ser  Ser  Gly  Glu  Arg  Gly
     770                 775                      780

Glu  Lys  Gly  Ser  Arg  Lys  Cys  Phe  Gln  Thr  Ala  His  Phe  Tyr  Val  Glu
785                      790                 795                           800

Asp  Ser  Ser  Ser  Pro  Arg  Val  Val  Pro  Asn  Glu  Ser  Val  Pro  Ile  Ile
                    805                 810                      815

Pro  Ile  Pro  Asp  Asp  Met  Glu  Ala  Ile  Pro  Val  Lys  Gln  Phe  Gly  Lys
                    820                 825                      830

His  Ile  Gly  Glu  Leu  Tyr  Ser  Asn  Ser  Gln  His  Gly  Phe  Ser  Glu  Asp
          835                      840                      845

Phe  Glu  Glu  Val  Gln  Arg  Cys  Thr  Ala  Asp  Met  Asn  Ile  Thr  Ala  Glu
     850                      855                 860

His  Ser  Asn  His  Pro  Asp  Asn  Lys  His  Lys  Asn  Arg  Tyr  Ile  Asn  Ile
865                      870                 875                           880

Leu  Ala  Tyr  Asp  His  Ser  Arg  Val  Lys  Leu  Arg  Pro  Leu  Pro  Gly  Lys
                    885                 890                      895

Asp  Ser  Lys  His  Ser  Asp  Tyr  Ile  Asn  Ala  Asn  Tyr  Val  Asp  Gly  Tyr
               900                 905                      910

Asn  Lys  Ala  Lys  Ala  Tyr  Ile  Ala  Thr  Gln  Gly  Pro  Leu  Lys  Ser  Thr
          915                      920                      925

Phe  Glu  Asp  Phe  Trp  Arg  Met  Ile  Trp  Glu  Gln  Asn  Thr  Gly  Ile  Ile
```

```
                              930                        935                        940
Ile  Met  Ile  Thr  Asn  Leu  Val  Glu  Lys  Gly  Arg  Arg  Lys  Cys  Asp  Gln
945                      950                       955                       960

Tyr  Trp  Pro  Thr  Glu  Asn  Thr  Glu  Glu  Tyr  Gly  Asn  Ile  Ile  Val  Thr
                         965                       970                       975

Leu  Lys  Ser  Thr  Lys  Val  His  Ala  Cys  Tyr  Thr  Val  Arg  Arg  Leu  Ser
                    980                       985                       990

Val  Arg  Asn  Thr  Lys  Val  Lys  Lys  Gly  Gln  Lys  Gly  Asn  Pro  Lys  Gly
               995                      1000                      1005

Arg  Gln  Asn  Glu  Arg  Thr  Val  Ile  Gln  Tyr  His  Tyr  Thr  Gln  Trp  Pro
          1010                     1015                     1020

Asp  Met  Gly  Val  Pro  Glu  Tyr  Ala  Leu  Pro  Val  Leu  Thr  Phe  Val  Arg
1025                     1030                     1035                     1040

Arg  Ser  Ser  Ala  Ala  Arg  Met  Pro  Asp  Met  Gly  Pro  Val  Leu  Val  His
                    1045                     1050                     1055

Cys  Ser  Ala  Gly  Val  Gly  Arg  Thr  Gly  Thr  Tyr  Ile  Val  Ile  Asp  Ser
               1060                     1065                     1070

Met  Leu  Gln  Gln  Ile  Lys  Asp  Lys  Ser  Thr  Val  Asn  Val  Leu  Gly  Phe
          1075                     1080                     1085

Leu  Lys  His  Ile  Arg  Thr  Gln  Arg  Asn  Tyr  Leu  Val  Gln  Thr  Glu  Glu
     1090                     1095                     1100

Gln  Tyr  Ile  Phe  Ile  His  Asp  Ala  Leu  Leu  Glu  Ala  Ile  Leu  Gly  Lys
1105                     1110                     1115                     1120

Glu  Thr  Ala  Val  Ser  Ser  Ser  Gln  Leu  His  Ser  Tyr  Val  Asn  Ser  Ile
                    1125                     1130                     1135

Leu  Ile  Pro  Gly  Val  Gly  Gly  Lys  Thr  Arg  Leu  Glu  Lys  Gln  Phe  Lys
               1140                     1145                     1150

Leu  Ile  Thr  Gln  Cys  Asn  Ala  Lys  Tyr  Val  Glu  Cys  Phe  Ser  Ala  Gln
          1155                     1160                     1165

Lys  Glu  Cys  Asn  Lys  Glu  Lys  Asn  Arg  Asn  Ser  Ser  Val  Val  Pro  Ala
     1170                     1175                     1180

Glu  Arg  Ala  Arg  Val  Gly  Leu  Ala  Pro  Leu  Pro  Gly  Met  Lys  Gly  Thr
1185                     1190                     1195                     1200

Asp  Tyr  Ile  Asn  Ala  Ser  Tyr  Ile  Met  Gly  Tyr  Tyr  Arg  Ser  Asn  Glu
                    1205                     1210                     1215

Phe  Ile  Ile  Thr  Gln  His  Pro  Leu  Pro  His  Thr  Thr  Lys  Asp  Phe  Trp
               1220                     1225                     1230

Arg  Met  Ile  Trp  Asp  His  Asn  Ala  Gln  Ile  Ile  Val  Met  Leu  Pro  Asp
          1235                     1240                     1245

Asn  Gln  Ser  Leu  Ala  Glu  Asp  Glu  Phe  Val  Tyr  Trp  Pro  Ser  Arg  Glu
     1250                     1255                     1260

Glu  Ser  Met  Asn  Cys  Glu  Ala  Phe  Thr  Val  Thr  Leu  Ile  Ser  Lys  Asp
1265                     1270                     1275                     1280

Arg  Leu  Cys  Leu  Ser  Asn  Glu  Glu  Gln  Ile  Ile  Ile  His  Asp  Phe  Ile
                    1285                     1290                     1295

Leu  Glu  Ala  Thr  Gln  Asp  Asp  Tyr  Val  Leu  Glu  Val  Arg  His  Phe  Gln
               1300                     1305                     1310

Cys  Pro  Lys  Trp  Pro  Asn  Pro  Asp  Ala  Pro  Ile  Ser  Ser  Thr  Phe  Glu
          1315                     1320                     1325

Leu  Ile  Asn  Val  Ile  Lys  Glu  Glu  Ala  Leu  Thr  Arg  Asp  Gly  Pro  Thr
     1330                     1335                     1340

Ile  Val  His  Asp  Glu  Tyr  Gly  Ala  Val  Ser  Ala  Gly  Met  Leu  Cys  Ala
1345                     1350                     1355                     1360
```

|  |  |  |  |  |  |  |  |  |  |  |  |  |  |  |
|---|---|---|---|---|---|---|---|---|---|---|---|---|---|---|
| Leu | Thr | Thr | Leu | Ser | Gln | Gln | Leu | Glu | Asn | Glu | Asn | Ala | Val | Asp | Val |
|  |  |  |  | 1365 |  |  |  | 1370 |  |  |  | 1375 |
| Phe | Gln | Val | Ala | Lys | Met | Ile | Asn | Leu | Met | Arg | Pro | Gly | Val | Phe | Thr |
|  |  |  |  | 1380 |  |  |  | 1385 |  |  |  | 1390 |
| Asp | Ile | Glu | Gln | Tyr | Gln | Phe | Val | Tyr | Lys | Ala | Met | Leu | Ser | Leu | Ile |
|  |  | 1395 |  |  |  | 1400 |  |  |  | 1405 |
| Ser | Thr | Lys | Glu | Asn | Gly | Asn | Gly | Pro | Met | Thr | Gly | Asp | Lys | Asn | Gly |
|  | 1410 |  |  |  | 1415 |  |  |  | 1420 |
| Ala | Val | Leu | Thr | Ala | Glu | Glu | Ser | Asp | Pro | Ala | Glu | Ser | Met | Glu | Ser |
| 1425 |  |  |  | 1430 |  |  |  | 1435 |  |  |  | 1440 |
| Leu | Val |

(2) INFORMATION FOR SEQ ID NO:4:

(i) SEQUENCE CHARACTERISTICS:
    (A) LENGTH: 107 amino acids
    (B) TYPE: amino acid
    (C) STRANDEDNESS: single
    (D) TOPOLOGY: unknown (ii) MOLECULE TYPE: protein (xi) SEQUENCE DESCRIPTION: SEQ ID NO:4:

| Ser | Gly | Pro | Pro | Arg | Lys | Val | Glu | Val | Glu | Pro | Leu | Asn | Ser | Thr | Ala |
|---|---|---|---|---|---|---|---|---|---|---|---|---|---|---|---|
| 1 |  |  |  | 5 |  |  |  | 10 |  |  |  | 15 |
| Val | His | Val | Tyr | Trp | Lys | Leu | Pro | Val | Pro | Ser | Lys | Gln | His | Gly | Gln |
|  |  |  | 20 |  |  |  | 25 |  |  |  | 30 |
| Ile | Arg | Gly | Tyr | Gln | Val | Thr | Tyr | Val | Arg | Leu | Glu | Asn | Gly | Glu | Pro |
|  |  | 35 |  |  |  | 40 |  |  |  | 45 |
| Arg | Gly | Leu | Pro | Ile | Ile | Gln | Asp | Val | Met | Leu | Ala | Glu | Ala | Gln | Trp |
| 50 |  |  |  | 55 |  |  |  | 60 |
| Arg | Pro | Glu | Glu | Ser | Glu | Asp | Tyr | Glu | Thr | Thr | Ile | Ser | Gly | Leu | Thr |
| 65 |  |  |  | 70 |  |  |  | 75 |  |  |  | 80 |
| Pro | Glu | Thr | Thr | Tyr | Ser | Val | Thr | Val | Ala | Ala | Tyr | Thr | Thr | Lys | Gly |
|  |  |  | 85 |  |  |  | 90 |  |  |  | 95 |
| Asp | Gly | Ala | Arg | Ser | Lys | Pro | Lys | Ile | Val | Thr |
|  |  |  | 100 |  |  |  | 105 |

(2) INFORMATION FOR SEQ ID NO:5:

(i) SEQUENCE CHARACTERISTICS:
    (A) LENGTH: 107 amino acids
    (B) TYPE: amino acid
    (C) STRANDEDNESS: single
    (D) TOPOLOGY: unknown (ii) MOLECULE TYPE: protein (xi) SEQUENCE DESCRIPTION: SEQ ID NO:5:

| Ser | Gly | Pro | Pro | Arg | Lys | Val | Glu | Val | Glu | Ala | Val | Asn | Ser | Thr | Ser |
|---|---|---|---|---|---|---|---|---|---|---|---|---|---|---|---|
| 1 |  |  |  | 5 |  |  |  | 10 |  |  |  | 15 |
| Val | Lys | Val | Ser | Trp | Arg | Ser | Pro | Val | Pro | Asn | Lys | Gln | His | Gly | Gln |
|  |  |  | 20 |  |  |  | 25 |  |  |  | 30 |
| Ile | Arg | Gly | Tyr | Gln | Val | His | Tyr | Val | Arg | Met | Glu | Asn | Gly | Glu | Pro |
|  |  | 35 |  |  |  | 40 |  |  |  | 45 |
| Lys | Gly | Gln | Pro | Met | Leu | Lys | Asp | Val | Met | Leu | Ala | Asp | Ala | Gln | Trp |
| 50 |  |  |  | 55 |  |  |  | 60 |
| Glu | Phe | Asp | Asp | Thr | Thr | Glu | His | Asp | Met | Ile | Ile | Ser | Gly | Leu | Gln |
| 65 |  |  |  | 70 |  |  |  | 75 |  |  |  | 80 |
| Pro | Glu | Thr | Ser | Tyr | Ser | Leu | Thr | Val | Thr | Ala | Tyr | Thr | Thr | Lys | Gly |

8 5                                    9 0                                     9 5

Asp    Gly    Ala    Arg    Ser    Lys    Pro    Lys    Leu    Val    Ser
    1                                  100                            105

( 2 ) INFORMATION FOR SEQ ID NO:6:

( i ) SEQUENCE CHARACTERISTICS:
            ( A ) LENGTH: 92 amino acids
            ( B ) TYPE: amino acid
            ( C ) STRANDEDNESS: single
            ( D ) TOPOLOGY: unknown ( i i ) MOLECULE TYPE: protein ( x i ) SEQUENCE DESCRIPTION: SEQ ID NO:6:

Leu    Ser    Pro    Pro    Thr    Asn    Leu    His    Leu    Glu    Ala    Asn    Pro    Asp    Thr    Gly
    1                             5                             10                            15

Val    Leu    Thr    Val    Ser    Trp    Glu    Arg    Ser    Thr    Thr    Pro    Asp    Ile    Thr    Gly
                    20                            25                            30

Tyr    Arg    Ile    Thr    Thr    Thr    Pro    Thr    Asn    Gly    Gln    Gln    Gly    Thr    Ala    Leu
                    35                            40                            45

Glu    Glu    Val    Val    His    Ala    Asp    Gln    Ser    Ser    Cys    Thr    Phe    Asp    Asn    Leu
            50                            55                            60

Ser    Pro    Gly    Leu    Glu    Tyr    Asn    Val    Ser    Val    Tyr    Thr    Val    Lys    Asp    Asp
    65                            70                            75                                    80

Lys    Glu    Ser    Val    Pro    Ile    Ser    Asp    Thr    Ile    Ile    Pro
                                    85                            90

( 2 ) INFORMATION FOR SEQ ID NO:7:

( i ) SEQUENCE CHARACTERISTICS:
            ( A ) LENGTH: 96 amino acids
            ( B ) TYPE: amino acid
            ( C ) STRANDEDNESS: single
            ( D ) TOPOLOGY: unknown ( i i ) MOLECULE TYPE: protein ( x i ) SEQUENCE DESCRIPTION: SEQ ID NO:7:

Pro    Gly    Pro    Pro    Gly    Gly    Ile    Arg    Ile    Glu    Glu    Ile    Arg    Asp    Thr    Ala
    1                             5                             10                            15

Val    Ala    Leu    Thr    Trp    Ser    Arg    Gly    Thr    Asp    Asn    His    Ser    Pro    Ile    Ser
                    20                            25                            30

Lys    Tyr    Thr    Ile    Gln    Ser    Lys    Thr    Phe    Leu    Ser    Glu    Glu    Trp    Lys    Asp
                    35                            40                            45

Ala    Lys    Thr    Glu    Pro    Ser    Asp    Ile    Glu    Gly    Asn    Met    Glu    Ser    Ala    Arg
            50                            55                            60

Val    Ile    Asp    Leu    Ile    Pro    Trp    Met    Glu    Tyr    Glu    Phe    Arg    Ile    Ile    Ala
    65                            70                            75                                    80

Thr    Asn    Thr    Leu    Gly    Thr    Gly    Glu    Pro    Ser    Met    Pro    Ser    Gln    Arg    Ile
                            85                            90                            95

( 2 ) INFORMATION FOR SEQ ID NO:8:

( i ) SEQUENCE CHARACTERISTICS:
            ( A ) LENGTH: 261 amino acids
            ( B ) TYPE: amino acid
            ( C ) STRANDEDNESS: single
            ( D ) TOPOLOGY: unknown ( i i ) MOLECULE TYPE: protein ( x i ) SEQUENCE DESCRIPTION: SEQ ID NO:8:

```
Met  Ala  Ser  Pro  Asp  Trp  Gly  Tyr  Asp  Asp  Lys  Asn  Gly  Pro  Glu  Gln
1                   5                        10                      15

Trp  Ser  Lys  Leu  Tyr  Pro  Ile  Ala  Asn  Gly  Asn  Asn  Gln  Ser  Pro  Val
               20                       25                      30

Asp  Ile  Lys  Thr  Ser  Glu  Thr  Lys  His  Asp  Thr  Ser  Leu  Lys  Pro  Ile
               35                       40                      45

Ser  Val  Ser  Tyr  Asn  Pro  Ala  Thr  Ala  Lys  Glu  Ile  Ile  Asn  Val  Gly
     50                       55                      60

His  Ser  Phe  His  Val  Asn  Phe  Glu  Asp  Asn  Asp  Asn  Arg  Ser  Val  Leu
65                       70                      75                           80

Lys  Gly  Gly  Pro  Phe  Ser  Asp  Ser  Tyr  Arg  Leu  Phe  Gln  Phe  His  Phe
                    85                       90                      95

His  Trp  Gly  Ser  Thr  Asn  Glu  His  Gly  Ser  Glu  His  Thr  Val  Asp  Gly
               100                      105                     110

Val  Lys  Tyr  Ser  Ala  Glu  Leu  His  Val  Ala  His  Trp  Asn  Ser  Ala  Lys
          115                      120                     125

Tyr  Ser  Ser  Leu  Ala  Glu  Ala  Ala  Ser  Lys  Ala  Asp  Gly  Leu  Ala  Val
     130                      135                     140

Ile  Gly  Val  Leu  Met  Lys  Val  Gly  Glu  Ala  Asn  Pro  Lys  Leu  Gln  Lys
145                      150                      155                          160

Val  Leu  Asp  Ala  Leu  Gln  Ala  Ile  Lys  Thr  Lys  Gly  Lys  Arg  Ala  Pro
               165                      170                     175

Phe  Thr  Asn  Phe  Asp  Pro  Ser  Thr  Leu  Leu  Pro  Ser  Ser  Leu  Asp  Phe
               180                      185                     190

Trp  Thr  Tyr  Pro  Gly  Ser  Leu  Thr  His  Pro  Pro  Leu  Tyr  Glu  Ser  Val
          195                      200                     205

Thr  Trp  Ile  Ile  Cys  Lys  Glu  Ser  Ile  Ser  Val  Ser  Ser  Glu  Gln  Leu
210                      215                      220

Ala  Gln  Phe  Arg  Ser  Leu  Leu  Ser  Asn  Val  Glu  Gly  Asp  Asn  Ala  Val
225                      230                      235                          240

Pro  Met  Gln  His  Asn  Asn  Arg  Pro  Thr  Gln  Pro  Leu  Lys  Gly  Arg  Thr
                    245                      250                     255

Val  Arg  Ala  Ser  Phe
               260
```

( 2 ) INFORMATION FOR SEQ ID NO:9:

( i ) SEQUENCE CHARACTERISTICS:
        ( A ) LENGTH: 260 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:9:

```
Met  Ser  His  His  Trp  Gly  Tyr  Gly  Lys  His  Asn  Gly  Pro  Glu  His  Trp
1                   5                        10                      15

His  Lys  Asp  Phe  Pro  Ile  Ala  Lys  Gly  Glu  Arg  Gln  Ser  Pro  Val  Asp
               20                       25                      30

Ile  Asp  Thr  His  Thr  Ala  Lys  Tyr  Asp  Pro  Ser  Leu  Lys  Pro  Leu  Ser
               35                       40                      45

Val  Ser  Tyr  Asp  Gln  Ala  Thr  Ser  Leu  Arg  Ile  Leu  Asn  Asn  Gly  His
     50                       55                      60

Ala  Phe  Asn  Val  Glu  Phe  Asp  Asp  Ser  Gln  Asp  Lys  Ala  Val  Leu  Lys
65                       70                      75                           80

Gly  Gly  Pro  Leu  Asp  Gly  Thr  Tyr  Arg  Leu  Ile  Gln  Phe  His  Phe  His
```

|   |   |   |   |   | 85 |   |   |   |   | 90 |   |   |   |   | 95 |
|---|---|---|---|---|---|---|---|---|---|---|---|---|---|---|---|

Trp Gly Ser Leu Asp Gly Gln Gly Ser Glu His Thr Val Asp Lys Lys
            100             105                 110

Lys Tyr Ala Ala Glu Leu His Leu Val His Trp Asn Thr Lys Tyr Gly
        115             120             125

Asp Phe Gly Lys Ala Val Gln Gln Pro Asp Gly Leu Ala Val Leu Gly
    130             135             140

Ile Phe Leu Lys Val Gly Ser Ala Lys Pro Gly Leu Gln Lys Val Val
145             150             155             160

Asp Val Leu Asp Ser Ile Lys Thr Lys Gly Lys Ser Ala Asp Phe Thr
            165             170             175

Asn Phe Asp Pro Arg Gly Leu Leu Pro Glu Ser Leu Asp Tyr Trp Thr
        180             185             190

Tyr Pro Gly Ser Leu Thr Thr Pro Pro Leu Leu Glu Cys Val Thr Trp
    195             200             205

Ile Val Leu Lys Glu Pro Ile Ser Val Ser Ser Glu Gln Val Leu Lys
    210             215             220

Phe Arg Lys Leu Asn Phe Asn Gly Glu Gly Glu Pro Glu Glu Leu Met
225             230             235             240

Val Asp Asn Trp Arg Pro Ala Gln Pro Leu Lys Asn Arg Gln Ile Lys
            245             250             255

Ala Ser Phe Lys
            260

(2) INFORMATION FOR SEQ ID NO:10:

(i) SEQUENCE CHARACTERISTICS:
        (A) LENGTH: 259 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:10:

Ala Lys Glu Trp Gly Tyr Ala Ser His Asn Gly Pro Asp His Trp His
1               5               10              15

Glu Leu Phe Pro Asn Ala Lys Gly Glu Asn Gln Ser Pro Ile Glu Leu
            20              25              30

His Thr Lys Asp Ile Arg His Asp Pro Ser Leu Gln Pro Trp Ser Val
        35              40              45

Ser Tyr Asp Gly Gly Ser Ala Lys Thr Ile Leu Asn Asn Gly Lys Thr
    50              55              60

Cys Arg Val Val Phe Asp Asp Thr Tyr Asp Arg Ser Met Leu Arg Gly
65              70              75              80

Gly Pro Leu Pro Gly Pro Tyr Arg Leu Arg Gln Phe His Leu His Trp
            85              90              95

Gly Ser Ser Asp Asp His Gly Ser Glu His Thr Val Asp Gly Val Lys
            100             105             110

Tyr Ala Ala Glu Leu His Leu Val His Trp Asn Pro Lys Tyr Asn Thr
        115             120             125

Phe Lys Glu Ala Leu Lys Gln Arg Asp Gly Ile Ala Val Ile Gly Ile
    130             135             140

Phe Leu Lys Ile Gly His Glu Asn Gly Glu Phe Gln Ile Phe Leu Asp
145             150             155             160

Ala Leu Asp Lys Ile Lys Thr Lys Gly Lys Glu Ala Pro Phe Thr Lys
            165             170             175

|     |     |     |     |     |     |     |     |     |     |     |     |     |     |     |
|-----|-----|-----|-----|-----|-----|-----|-----|-----|-----|-----|-----|-----|-----|-----|
| Phe | Asp | Pro | Ser<br>180 | Cys | Leu | Phe | Pro | Ala<br>185 | Cys | Arg | Asp | Tyr | Trp<br>190 | Thr | Tyr |
| Gln | Gly | Ser | Phe<br>195 | Thr | Thr | Pro | Pro<br>200 | Cys | Glu | Glu | Cys<br>205 | Ile | Val | Trp | Leu |
| Leu | Leu | Lys<br>210 | Glu | Pro | Met | Thr<br>215 | Val | Ser | Ser | Asp | Gln<br>220 | Met | Ala | Lys | Leu |
| Arg<br>225 | Ser | Leu | Leu | Ser | Ser<br>230 | Ala | Glu | Asn | Glu | Pro<br>235 | Pro | Val | Pro | Leu | Val<br>240 |
| Ser | Asn | Trp | Arg | Pro<br>245 | Pro | Gln | Pro | Ile | Asn<br>250 | Asn | Arg | Val | Val | Arg<br>255 | Ala |
| Ser | Phe | Lys |     |     |     |     |     |     |     |     |     |     |     |     |     |

( 2 ) INFORMATION FOR SEQ ID NO:11:

( i ) SEQUENCE CHARACTERISTICS:
        ( A ) LENGTH: 262 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:11:

|     |     |     |     |     |     |     |     |     |     |     |     |     |     |     |     |
|-----|-----|-----|-----|-----|-----|-----|-----|-----|-----|-----|-----|-----|-----|-----|-----|
| Gly<br>1 | His | Gly | Val | Glu<br>5 | Trp | Thr | Tyr | Ser | Glu<br>10 | Gly | Met | Leu | Asp | Glu<br>15 | Ala |
| His | Trp | Pro | Leu<br>20 | Glu | Tyr | Pro | Lys<br>25 | Cys | Gly | Gly | Arg | Arg<br>30 | Gln | Ser | Pro |
| Ile | Asp | Leu<br>35 | Gln | Met | Lys | Lys | Val<br>40 | Gln | Tyr | Asn | Pro | Ser<br>45 | Leu | Arg | Ala |
| Leu | Asn<br>50 | Leu | Thr | Gly | Tyr | Gly<br>55 | Leu | Trp | His | Gly | Glu<br>60 | Phe | Pro | Val | Thr |
| Asn<br>65 | Asn | Gly | His | Thr | Val<br>70 | Gln | Ile | Ser | Leu | Pro<br>75 | Ser | Thr | Met | Ser | Met<br>80 |
| Thr | Thr | Ser | Asp | Gly<br>85 | Thr | Gln | Tyr | Leu | Ala<br>90 | Lys | Gln | Met | His | Phe<br>95 | His |
| Trp | Gly | Gly | Ala<br>100 | Ser | Ser | Glu | Ile<br>105 | Ser | Gly | Ser | Glu | His<br>110 | Thr | Val | Asp |
| Gly | Met | Arg<br>115 | Tyr | Val | Ile | Glu | Ile<br>120 | His | Val | Val | His | Tyr<br>125 | Asn | Ser | Lys |
| Tyr | Asn<br>130 | Ser | Tyr | Glu | Glu | Ala<br>135 | Gln | Lys | Glu | Pro | Asp<br>140 | Gly | Leu | Ala | Val |
| Leu<br>145 | Ala | Ala | Leu | Val | Glu<br>150 | Val | Lys | Asp | Tyr | Thr<br>155 | Glu | Asn | Ala | Tyr | Tyr<br>160 |
| Ser | Lys | Phe | Ile | Ser<br>165 | Asn | Leu | Glu | Asp | Ile<br>170 | Arg | Tyr | Ala | Gly | Gln<br>175 | Ser |
| Thr | Val | Leu | Arg<br>180 | Gly | Leu | Asp | Ile | Glu<br>185 | Asp | Met | Leu | Pro | Gly<br>190 | Asp | Leu |
| Arg | Tyr | Tyr<br>195 | Tyr | Ser | Tyr | Leu | Gly<br>200 | Ser | Leu | Thr | Thr | Pro<br>205 | Pro | Cys | Thr |
| Glu | Asn<br>210 | Val | His | Trp | Phe | Val<br>215 | Val | Ala | Asp | Thr | Val<br>220 | Lys | Leu | Ser | Lys |
| Thr<br>225 | Gln | Val | Glu | Lys | Leu<br>230 | Glu | Asn | Ser | Leu | Leu<br>235 | Asn | His | Gln | Asn | Lys<br>240 |
| Thr | Ile | Gln | Asn | Asp<br>245 | Tyr | Arg | Arg | Thr | Gln<br>250 | Pro | Leu | Asn | His | Arg<br>255 | Val |
| Val | Glu | Ala | Asn | Phe<br>260 | Met |     |     |     |     |     |     |     |     |     |     |

(2) INFORMATION FOR SEQ ID NO:12:

(i) SEQUENCE CHARACTERISTICS:
        (A) LENGTH: 266 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:12:

```
Glu Gly Val Glu Trp Gly Tyr Glu Glu Val Glu Trp Gly Leu Val
 1               5                  10                  15

Phe Pro Asp Ala Asn Gly Glu Tyr Gln Ser Pro Ile Asn Leu Asn Ser
             20                  25                  30

Arg Glu Ala Arg Tyr Asp Pro Ser Leu Leu Asp Val Arg Leu Ser Pro
             35                  40                  45

Asn Tyr Val Val Cys Arg Asp Cys Glu Val Thr Asn Asp Gly His Thr
     50                  55                  60

Ile Gln Val Ile Leu Lys Ser Lys Ser Val Leu Ser Gly Gly Pro Leu
65                  70                  75                  80

Pro Gln Gly Gln Glu Phe Glu Leu Tyr Glu Val Arg Phe His Trp Gly
                 85                  90                  95

Arg Glu Asn Gln Arg Gly Ser Glu His Thr Val Asn Phe Lys Ala Phe
                100                 105                 110

Pro Met Glu Leu His Leu Ile His Trp Asn Ser Thr Leu Phe Gly Ser
            115                 120                 125

Ile Asp Glu Ala Val Gly Lys Pro His Gly Ile Ala Ile Ile Ala Leu
    130                 135                 140

Phe Val Gln Ile Gly Lys Glu His Val Gly Leu Lys Ala Val Thr Glu
145                 150                 155                 160

Ile Leu Gln Asp Ile Gln Tyr Lys Gly Lys Ser Lys Thr Ile Pro Cys
                165                 170                 175

Phe Asn Pro Asn Thr Leu Leu Pro Asp Phe Leu Leu Arg Asp Tyr Trp
            180                 185                 190

Val Tyr Glu Gly Ser Leu Thr Ile Pro Pro Cys Ser Glu Gly Val Thr
        195                 200                 205

Trp Ile Leu Phe Arg Tyr Pro Leu Thr Ile Ser Gln Met Gln Ile Glu
    210                 215                 220

Glu Phe Arg Arg Leu Arg Thr His Val Lys Gly Val Glu Leu Val Glu
225                 230                 235                 240

Gly Cys Asp Gly Ile Leu Gly Asp Asn Phe Arg Pro Thr Gln Pro Leu
                245                 250                 255

Ser Asp Arg Val Ile Arg Ala Ala Phe Ser
            260                 265
```

(2) INFORMATION FOR SEQ ID NO:13:

(i) SEQUENCE CHARACTERISTICS:
        (A) LENGTH: 235 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:13:

```
Met Pro Gln Gln Leu Ser Pro Ile Asn Ile Glu Thr Lys Lys Ala Ile
```

|  |  |  |  |  |  |  |  |  |  |  |  |  |  |  |
|---|---|---|---|---|---|---|---|---|---|---|---|---|---|---|
| 1 |  |  |  | 5 |  |  |  |  | 10 |  |  |  |  | 15 |
| Ser | Asn | Ala | Arg<br>20 | Leu | Lys | Pro | Leu | Asp<br>25 | Ile | His | Tyr | Asn<br>30 | Glu | Ser | Lys |
| Pro | Thr | Thr<br>35 | Ile | Gln | Asn | Thr | Gly<br>40 | Lys | Leu | Val | Arg | Ile<br>45 | Asn | Phe | Lys |
| Gly | Gly<br>50 | Tyr | Ile | Ser | Gly | Gly<br>55 | Phe | Ile | Pro | Asn | Glu<br>60 | Tyr | Val | Leu | Ser |
| Ser<br>65 | Leu | His | Ile | Tyr | Trp<br>70 | Gly | Lys | Glu | Asp | Asp<br>75 | Tyr | Gly | Ser | Asn | His<br>80 |
| Leu | Ile | Asp | Val | Tyr<br>85 | Lys | Tyr | Ser | Gly | Glu<br>90 | Ile | Asn | Leu | Val | His<br>95 | Trp |
| Asn | Lys | Lys | Lys<br>100 | Tyr | Ser | Ser | Tyr | Glu<br>105 | Glu | Ala | Lys | Lys | His<br>110 | Asp | Asp |
| Gly | Leu | Ile<br>115 | Ile | Ile | Ser | Ile | Phe<br>120 | Leu | Gln | Val | Ser | Asp<br>125 | His | Lys | Asn |
| Val | Tyr<br>130 | Phe | Gln | Lys | Ile | Val<br>135 | Asn | Gln | Leu | Asp | Ser<br>140 | Ile | Arg | Ser | Ala |
| Asn<br>145 | Thr | Ser | Ala | Pro | Phe<br>150 | Asp | Ser | Val | Phe | Tyr<br>155 | Leu | Asp | Asn | Leu | Leu<br>160 |
| Pro | Ser | Thr | Leu | Asp<br>165 | Tyr | Phe | Thr | Tyr | Leu<br>170 | Gly | Thr | Thr | Ile | Lys<br>175 | His |
| Ser | Ala | Asp | Ala<br>180 | Val | Trp | Ile | Ile | Phe<br>185 | Pro | Thr | Pro | Ile | Asn<br>190 | Ile | Asn |
| Ser | Asp | Gln<br>195 | Leu | Ser | Lys | Phe | Arg<br>200 | Thr | Leu | Leu | Ser | Ser<br>205 | Ser | Asn | His |
| Asp | Gly<br>210 | Lys | Pro | Tyr | Tyr | Ile<br>215 | Thr | Glu | Asn | Tyr | Arg<br>220 | Asn | Pro | Tyr | Lys |
| Leu<br>225 | Asn | Asp | Asp | Thr | Gln<br>230 | Val | Tyr | Tyr | Ser | Gly<br>235 |  |  |  |  |  |

( 2 ) INFORMATION FOR SEQ ID NO:14:

( i ) SEQUENCE CHARACTERISTICS:
        ( A ) LENGTH: 373 amino acids
        ( B ) TYPE: amino acid
        ( C ) STRANDEDNESS: double
        ( D ) TOPOLOGY: unknown ( i i ) MOLECULE TYPE: protein ( x i ) SEQUENCE DESCRIPTION: SEQ ID NO:14:

|  |  |  |  |  |  |  |  |  |  |  |  |  |  |  |
|---|---|---|---|---|---|---|---|---|---|---|---|---|---|---|
| Glu<br>1 | Glu | Ile | Gly | Trp<br>5 | Ser | Tyr | Thr | Gly | Ala<br>10 | Leu | Asn | Gln | Lys | Asn<br>15 | Trp |
| Gly | Lys | Lys | Tyr<br>20 | Pro | Thr | Cys | Asn | Ser<br>25 | Pro | Lys | Gln | Ser | Pro<br>30 | Ile | Asn |
| Ile | Asp | Glu<br>35 | Asp | Leu | Thr | Gln | Val<br>40 | Asn | Val | Asn | Leu | Lys<br>45 | Lys | Leu | Lys |
| Phe | Gln<br>50 | Gly | Trp | Asp | Lys | Thr<br>55 | Ser | Leu | Glu | Asn | Thr<br>60 | Phe | Ile | His | Asn |
| Thr<br>65 | Gly | Lys | Thr | Val | Glu<br>70 | Ile | Asn | Leu | Thr | Asn<br>75 | Asp | Tyr | Arg | Val | Ser<br>80 |
| Gly | Gly | Val | Ser | Glu<br>85 | Met | Val | Phe | Lys | Ala<br>90 | Ser | Lys | Ile | Thr | Phe<br>95 | His |
| Trp | Gly | Lys | Cys<br>100 | Asn | Met | Ser | Ser | Asp<br>105 | Gly | Ser | Glu | His | Ser<br>110 | Leu | Glu |
| Gly | Gln | Lys<br>115 | Phe | Pro | Leu | Glu | Met<br>120 | Gln | Ile | Tyr | Cys | Phe<br>125 | Asp | Ala | Asp |

| | | | | | | | | | | | | | | |
|---|---|---|---|---|---|---|---|---|---|---|---|---|---|---|
| Arg | Phe 130 | Ser | Ser | Phe | Glu | Glu 135 | Ala | Val | Lys | Gly | Lys 140 | Gly | Lys | Leu | Arg |
| Ala 145 | Leu | Ser | Ile | Leu | Phe 150 | Glu | Val | Gly | Thr | Glu 155 | Glu | Asn | Leu | Asp | Phe 160 |
| Lys | Ala | Ile | Ile | Asp 165 | Gly | Val | Glu | Ser | Val 170 | Ser | Arg | Phe | Gly | Lys 175 | Gln |
| Ala | Ala | Leu | Asp 180 | Pro | Phe | Ile | Leu | Leu 185 | Asn | Leu | Leu | Pro | Asn 190 | Ser | Thr |
| Asp | Lys | Tyr 195 | Tyr | Ile | Tyr | Asn | Gly 200 | Ser | Leu | Thr | Ser | Pro 205 | Pro | Cys | Thr |
| Asp | Thr 210 | Val | Asp | Trp | Ile | Val 215 | Phe | Lys | Asp | Thr | Val 220 | Ser | Ile | Ser | Glu |
| Ser 225 | Gln | Leu | Ala | Val | Phe 230 | Cys | Glu | Val | Leu | Thr 235 | Met | Gln | Gln | Ser | Gly 240 |
| Tyr | Val | Met | Leu | Met 245 | Asp | Tyr | Leu | Gln | Asn 250 | Asn | Phe | Arg | Glu | Gln 255 | Gln |
| Tyr | Lys | Phe | Ser 260 | Arg | Gln | Val | Phe | Ser 265 | Ser | Tyr | Thr | Gly | Lys 270 | Glu | Glu |
| Ile | His | Glu 275 | Ala | Val | Cys | Ser | Ser 280 | Glu | Pro | Glu | Asn | Val 285 | Gln | Ala | Asp |
| Pro | Glu 290 | Asn | Tyr | Thr | Ser | Leu 295 | Leu | Val | Thr | Trp | Glu 300 | Arg | Pro | Arg | Val |
| Val 305 | Tyr | Asp | Thr | Met | Ile 310 | Glu | Lys | Phe | Ala | Val 315 | Leu | Tyr | Gln | Gln | Leu 320 |
| Asp | Gly | Glu | Asp | Gln 325 | Thr | Lys | His | Glu | Phe 330 | Leu | Thr | Asp | Gly | Tyr 335 | Gln |
| Asp | Leu | Gly | Ala 340 | Ile | Leu | Asn | Asn | Leu 345 | Leu | Pro | Asn | Met | Ser 350 | Tyr | Val |
| Leu | Gln | Ile 355 | Val | Ala | Ile | Cys | Thr 360 | Asn | Gly | Leu | Tyr | Gly 365 | Lys | Tyr | Ser |
| Asp | Gln 370 | Leu | Ile | Val | | | | | | | | | | | |

RECEPTOR-TYPE PHOSPHOTYROSINE PHOSPHATASE-γ

The present application is a continuation-in-part of U.S application Ser. No. 07/654,188, filed Feb. 26, 1991, now abandoned, which was a continuation-in-part of U.S. application Ser. No. 07/551,270, filed Jul. 11, 1990, now abandoned. The entire contents of both of the above applications are hereby incorporated by reference.

1. INTRODUCTION

The invention in the field of biochemistry and cell and molecular biology relates to novel receptor-type protein tyrosine phosphatase protein or glycoprotein, termed RPTPγ (also known as RPTPase-γ), DNA coding therefor, methods for production and identification of the protein, and methods for screening compounds capable of binding to and inhibiting or stimulating PTPase enzymatic activity.

2. BACKGROUND OF THE INVENTION

The identification of several growth factor receptors and retroviral oncogenes as tyrosine-specific protein kinases indicated that protein phosphorylation on tyrosine residues plays a key role in cellular growth control. This notion has recently received support by the observation that the level of tyrosine phosphorylation of enzymes thought to play an important role in signal transduction (such as phospholipase C) correlates with their increased activity upon growth factor stimulation, thus establishing a functional role for tyrosine phosphorylation (Ullrich, A., et al., *Cell* 61:203–212 (1990)).

The degree and pattern of phosphorylation of tyrosine residues on cellular proteins are regulated by the opposing activities of protein-tyrosine kinases (PTKases; ATP:protein-tyrosine O-phosphotransferase, EC 2.7.1.112) and protein-tyrosine-phosphatases (PTPases; protein-tyrosine-phosphate phosphohydrolase, EC 3.1.3.48). The structural characteristics and evolution of PTKases as well as their role in the regulation of cell growth have been reviewed (Hunter, T., et al., *Annu. Rev. Biochem.* 54:897–930 (1985); Ullrich, A., et al., supra).

2.1. PTKases

Tyrosine kinases comprise a discrete family of enzymes having common ancestry with, but major differences from, serine/threonine-specific protein kinases (Hanks, S. K. et al., (1988) *Science* 241, 42–52). The mechanisms leading to changes in activity of tyrosine kinases are best understood for receptor-type tyrosine kinases which have a transmembrane topology (Ullrich, A. et al., supra). With such kinases, the binding of specific ligands to the extracellular domain of these enzymes is thought to induce their oligomerization leading to an increase in tyrosine kinase activity and activation of the signal transduction pathways (Ullrich, A. et al., supra). The importance of this activity is supported by the knowledge that dysregulation of kinase activity through mutation or over-expression is a mechanism for oncogenic transformation (Hunter, T. et al., supra; Ullrich, A. et al., 1990, supra).

2.2. PTPases

The protein phosphatases are composed of at least two separate and distinct families (Hunter, T. *Cell,* 58:1013–1016 (1989)), the protein serine/threonine phosphatases and the protein tyrosine phosphatases. This is in contrast to protein kinases, which show clear sequence similarity between serine/threonine-specific and tyrosine-specific enzymes.

There appear to be two varieties of PTPase molecules. The first group is comprised of small, soluble enzymes that contain a single conserved phosphatase catalytic domain, and include (1) placental PTPase 1B (Charbonneau, H. et al., *Proc. Natl. Acad. Sci.* 86:5252–5256 (1989); Chernoff, J. et al., *Proc. Natl. Acad. Sci. USA* 87:2735–2789 (1990)), (2) T-cell PTPase (Cool, D. E. et al., *Proc. Natl. Acad. Sci. USA* 86:5257–5261 (1989)), and (3) rat brain PTPase (Guan, K., et al., *Proc. Natl. Acad. Sci. USA,* 87:1501–1505 (1990)).

The second group is made up of the more complex, receptor-linked PTPases, termed R-PTPases or RPTPs, which are of high molecular weight and contain two tandemly repeated conserved domains separated by 56–57 amino acids. One example of RPTPs are the leukocyte common antigens (LCA) (Ralph, S. J., *EMBO J.,* 6:1251–1257 (1987); Charbonneau, H., et al., *Proc. Natl. Acad. Sci. USA,* 85:7182–7186 (1988)). LCA, also known as CD45, T200 and Ly-5 (reviewed in Thomas, M. L., *Ann. Rev. Immunol.* 7:339–369 (1989)) comprises a group of membrane glycoproteins expressed exclusively in hemopoietic (except late erythroid) cells, derived from a common gene by alternative splicing events involving the amino terminus of the proteins. Whereas the precise function of CD45 is unknown, many studies have implicated these antigens in a number of processes, including the activity of cytotoxic T lymphocytes and natural killer cells, IL-2 receptor expression, B-cell differentiation, and T lymphocyte proliferation (Pingel, J. T. et al., *Cell* 58:1055–1065 (1989)).

Other examples of RPTPs are the LCA-related protein, LAR (Streuli, M. et al., *J. Exp. Med.,* 168:1523–1530 (1988)), and the LAR-related Drosophila proteins DLAR and DPTP (Streuli, M., et al., *Proc. Natl. Acad. Sci. USA,* 86:8698–8702 (1989)). Jirik et al. screened a cDNA library derived from the human hepatoblastoma cell line, HepG2, with a probe encoding the two PTPase domains of LCA (*FASEB J.* 4:A2082 (1990), abstr. 2253) and discovered a cDNA clone encoding a new RPTP, named He-PTP. The HePTP gene appeared to be expressed in a variety of human and murine cell lines and tissues.

While we are beginning to understand more about the structure and diversity of the PTPases, much remains to be learned about their cellular functions. It has been suggested (Tonks, N. K., et al., *Biochemistry,* 27:8695–8701 (1988)) that the small, soluble PTPase enzymes may have a "housekeeping" function. On the other hand, the RPTPs would be expected to be more restricted in their activities because of their location in the cell membrane and their potential regulation by extracellular ligands. Regarding the role of LCA (CD45) in T cells, it was found that T cell clones deficient in the expression of LCA failed to proliferate when stimulated by a specific antigen or by cross-linking of CD3 (Pingel, J. T., et al., supra). PTPase cross-linking inhibits T cell receptor CD3-mediated activation in human T cells (Kiener, P. A. et al., *J. Immunol.* 143:23–28 (1989)). The PTPase activity of LCA plays a role in the activation of pp56$^{1ck}$, a lymphocyte-specific PTKase (Mustelin, T., et al., *Proc. Natl. Acad. Sci. USA,* 86:6302–6306 (1989); Ostergaard, H. L., et al., *Proc. Natl. Acad. Sci. USA,* 86:8959–8963 (1989)). These authors hypothesized that the phosphatase activity of LCA activates pp56$^{1ck}$ by dephosphorylation of a C-terminal tyrosine residue, which may, in turn, be related to T-cell activation.

Using site-directed mutagenesis to determine which of four conserved cysteines in LCA (two per phosphatase domain) was required for enzyme activity toward artificial substrates, Streuli et al. (1989, supra) found that only one cysteine residue (residue 177 of LCA phosphatase domain-1) of LCA was essential for activity, indicating that, most likely, only the first phosphatase domain has enzymatic activity. However, the possibility that the second domain can dephosphorylate a different substrate was not excluded. More recently, Streuli et. al. (*EMBO J.*, 9:2399–2407 (1990)) determined that the second conserved domain of LCA (and of LAR) lacked detectable phosphatase activity but sequences within the domain could influence substrate specificity.

Thus, a better understanding of, and an ability to control, phosphotyrosine metabolism, requires knowledge not only the role of PTKase activity, but the action of PTPase enzymes as well. Elevation of cellular phosphotyrosine may occur through mechanisms other than the activation of a tyrosine kinase itself. For instance, expression of the v-crk oncogene, though not a tyrosine kinase, induces the phosphorylation of tyrosine residues through a poorly understood mechanism (Mayer, B. J. et al. (1988) *Nature* 332, 272–275). Potentially, such an outcome could result from either mutation of the substrate or through a general decrease in cellular phosphatase activity, especially in view of the normally high turnover rate of cellular tyrosine-phosphate (Sefton, B. M. et al. (1980) *Cell* 20, 807–816). The latter possibility is suggested by the demonstration that tyrosine phosphatase inhibitors can "reversibly transform" cells (Klarlund, J. K. *Cell* 41: 707–717 (1985)). PTPases could therefor act as recessive oncogenes.

It is becoming clear that dephosphorylation of tyrosine can by itself function as an important regulatory mechanism. Dephosphorylation of a C-terminal tyrosine residue stimulates tyrosine kinase activity in the src-family of tyrosine kinases (Hunter, T. (1987) *Cell* 49, 1–4). Tyrosine dephosphorylation has been suggested to be an obligatory step in the mitotic activation of the MPF (maturation promoting factor) kinase (Morla, A. O. et al. (1989) *Cell* 58, 193–203). Lastly, genetic analysis of primitive eukaryotes has established crucial roles for serine phosphatase in cellular physiology (Cyert, M. S. et al. (1989) *Cell* 57, 891–893). These observations point out the need in the art for increasing our understanding of the mechanisms that regulate PTPase activity.

It is clear in the art that further delineation of structure-function relationships among these PTPases and RPTP membrane receptors are needed to gain important understanding of the mechanisms of cell growth, differentiation, and oncogenesis.

3. SUMMARY OF THE INVENTION

The present inventors have conceived of a role for RPTPs in cellular control mechanisms, both as potential anti-oncogenes, and as effectors in a newly discovered mechanism of transmembrane signalling. They therefore undertook a search for individual RPTP genes and proteins potentially involved in such processes, and describe herein the identification of a novel, widely expressed member of the RPTP family, RPTPγ, which has a transmembrane topology. The extracellular domains of members of this RPTP family is related to RPTPβ but is unrelated to any other RPTP previously described. The novel RPTPγ, in a manner analogous to receptor tyrosine kinases, is subject to direct regulation by extracellular ligands which bind to the extracellular portion.

The present invention thus provides a human receptor-type protein tyrosine phosphatase-γ (RPTPγ) protein or glycoprotein molecule, a functional derivative of the human RPTPγ, or a homolog of the human RPTPγ in another mammalian species. When the RPTPγ molecule is of natural origin, it is substantially free of other proteins or glycoproteins with which it is natively associated. RPTPγ is naturally expressed in mammalian brain and is developmentally and anatomically regulated. It is also expressed in lung, kidney, heart, skeletal muscle, liver, spleen, and testes. The RPTPγ molecule of the present invention may not be of natural origin and, for example, may be prepared by chemical or recombinant means. Thus, the substantially pure RPTPγ protein or glycoprotein of the present invention may be produced by biochemical purification of the protein or glycoprotein of natural origin or by production using chemical synthesis or by recombinant expression in prokaryotic or eukaryotic hosts.

In particular, the invention is directed to an RPTPγ protein or glycoprotein having the amino acid sequence of human RPTPγ shown in FIG. 4 [SEQ ID NO:2]. In another embodiment is provided a functional derivative thereof.

The invention is further directed to a nucleic acid molecule, preferably DNA, consisting essentially of a nucleotide sequence encoding RPTPγ. Preferably, the nucleic acid molecule encodes human RPTPγ or encodes a functional derivative thereof. The DNA molecule preferably comprises the sequence SEQ ID NO:1. The DNA molecule is preferably cDNA or genomic DNA. The invention is further directed to the DNA molecule in the form of an expression vehicle, as well as prokaryotic and eukaryotic hosts transformed or transfected with the DNA molecule.

Also included in the present invention is a process for preparing an RPTPγ protein or glycoprotein, or a functional derivative thereof, comprising:
(a) culturing a host capable of expressing the protein, glycoprotein or functional derivative under culturing conditions,
(b) expressing the protein, glycoprotein or functional derivative; and
(c) recovering the protein, glycoprotein or functional derivative from the culture.

This invention is also directed to an antibody, either polyclonal, monoclonal, or chimeric, which is specific for the RPTPγ protein or glycoprotein.

This invention is also directed to a method for detecting the presence of nucleic acid encoding a normal or mutant RPTPγ in a cell or in a subject, comprising:
(a) contacting a cell or an extract thereof from the subject with an oligonucleotide probe encoding at least a portion of a normal or mutant RPTPγ under hybridizing conditions; and
(b) measuring the hybridization of the probe to the nucleic acid of the cell, thereby detecting the presence of the nucleic acid, preferably DNA.

The DNA can be selectively amplified, using the polymerase chain reaction, prior to assay.

The invention is further directed to a method for detecting the presence, or measuring the quantity of RPTPγ in a cell or cells, comprising:
(a) contacting said cell or an extract thereof with an antibody specific for an epitope of RPTPγ; and
(b) detecting the binding of the antibody to the cell or extract thereof, or measuring the quantity of antibody bound, thereby detecting the presence or measuring the quantity of the RPTPγ.

The present invention is also directed to methods for identifying and isolating a compound capable of binding to RPTPγ from a chemical or biological preparation comprising:
(a) attaching RPTPγ, or the ligand-binding portion thereof, to a solid phase matrix;
(b) contacting the chemical or biological preparation with the solid phase matrix allowing the compound to bind, and washing away any unbound material;
(c) detecting the presence of the compound bound to the solid phase matrix; and, for purposes of isolation,
(d) eluting the bound compound, thereby isolating the compound.

Finally, the invention includes a method for identifying an agent capable of stimulating or inhibiting the phosphatase enzymatic activity of RPTPγ, comprising:
(a) contacting the agent with the RPTPγ in pure form, in a membrane preparation, or in a whole live or fixed cell;
(b) incubating the mixture in step (a) for a sufficient interval;
(c) measuring the enzymatic activity of the RPTPγ;
(d) comparing the enzymatic activity to that of the RPTPγ incubated without the agent,
thereby determining whether the agent stimulates or inhibits the enzymatic activity.

4. DESCRIPTION OF THE FIGURES

Figure 1B:
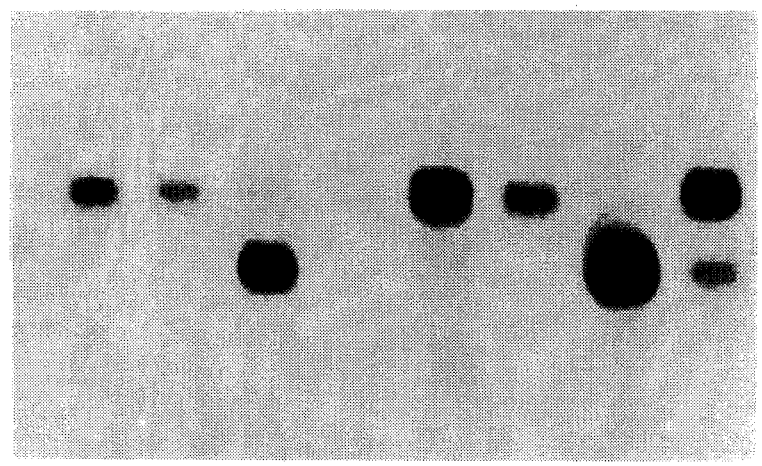

FIG. 1 shows the expression of RPTPγ in different murine tissues using Northern blot analysis of poly A$^+$ RNA. PANEL A: the blot was probed with an RPTPγ probe encompassing the first catalytic domain, the juxtamembrane domain, the transmembrane domain and the beginning of the extracellular domain. PANEL B: shows the same blot probed with a β-actin probe.

FIG. 2 shows results of in situ hybridization analysis of RPTPγ in the newborn and adult rat brain. Panel A shows a horizontal section through a newborn rat brain indicating the highest level of expression in the hippocampal formation (H), the cortex (C), the septal nuclei (S), and the midline thalamic nuclei (T). Panel B shows a sagittal section through an adult rat brain indicating the highest level of expression in the hippocampal formation (H).

FIG. 3 shows the nucleotide sequence of human RPTPγ (SEQ ID NO:1) as well as the deduced amino acid sequence (SEQ ID NO:2).

FIG. 4 shows the amino acid sequences of human RPTPγ and murine RPTPγ (SEQ ID NO:3). Amino acids that are different in the murine sequence are indicated. Dashes indicate amino acids that are not found in one of the sequences. The N-terminal hydrophobic signal peptide (von Heijne, G. *Nuc. Acids Res.* 14:4683–4690 (1986)) and the transmembrane domain are underlined. The potential N-glycosylation sites are indicated by arrowheads. The putative proteolytic cleavage site is indicated by an open triangle. The CAH-like domain and the phosphatase domains DI and DII are boxed.

FIG. 5 shows a fibronectin (FN) type III repeat in RPTPγ. The sequences of the FN type III repeat of human RPTPγ is aligned to typical fibronectin type III repeats of the human tyrosine phosphatases LAR (SEQ ID NO:4) (HLAR; Streuli et al., *J. Exp. Med.* 168:1523–1530 (1988)) and HPTPδ (SEQ ID NO:5) (Kreuger et al., *EMBO J.* 9:3241–3252 (1990)), to domain III-7 of human FN (SEQ ID NO:6) (Fbn II-7; Kornblihtt et al., *EMBO J.* 4:1755–1759 (1985)) and to a FN domain of chicken contactin (SEQ ID NO:7) ("contac": Ranscht et al., *J. Cell Biol.* 107:1561–1573 (1988)). Amino acid residues that are shared by four repeats or more are printed in bold font and indicated in the bottom row as a consensus sequence.

FIG. 6 presents an alignment of the CAH-like domain in RPTPγ with different forms of CAH. Panel A shows the sequence of the CAH-like domains of human and murine RPTPγ aligned with representative sequences of the CAH family: human CAH 1,2,3 (SEQ ID NOS:8, 9, 10, respectively) (sequences can be found in Swissprot accession numbers P00915, P00918, and P07451, respectively), sheep CAH-6 (SEQ ID NO:11) and vaccina virus (SEQ ID NO:12). CAH-like protein (Swissprot accession numbers P0860 and P04195, respectively) and mouse CAH related protein (SEQ ID NO:13) (Genebank accession number X6197). Residues conserved in at least five of the eight sequences are boxed. The position numbers in human RPTPγ of the first and last amino acid in each line are indicated. The three His residues involved in Zn binding in CAH are indicated with arrowheads. Panel B is a matrix showing the percent identity between the CAH-like domains in human and murine RPTPγ and the six CAH sequences, derived from the alignments shown in panel A.

FIG. 7 shows a comparison between the zinc binding site of CAH and the putative metal binding site in the RPTPγ model. Top: Stereo view of the zinc binding site in human carbonic anhydrase II, viewed roughly from the direction of the water molecule which is the fourth zinc ligand in this enzyme (OHH263; See: Ericksson, A. E. et al., *Proteins* 4:274–282 (1988)). Note the tetrahedral coordination of the zinc. Bonds from the zinc to ligand atoms are shown as thin lines. Bottom: Stereo view of the putative metal binding site in the RPTPγ domain (same view as top drawing), after applying the substitutions His 94 to Glu and His 119 to Gln and energy minimization ( ). Glu 106, which is part of the active site in human carbonic anhydrase II has been rotated to become one of the potential ligands. Note the planar constellation of atoms around the putative metal. Bidentate coordination is shown for Glu 94 and Glu 106. All the numbers of residues are according to carbonic anhydrase II.

FIG. 8 shows that RPTPγ and RPTPβ (SEQ ID NO:14) define a new subfamily of receptor tyrosine phosphatases. Panel A shows alignment of the carbonic anhydrase-like domains and the FN type III repeats of RPTPγ and RPTPβ. The aligned CAH domains and FN type III repeats are boxed. Identical amino acids are indicated by a connecting line. Panel B is a schematic diagram summarizing the conserved features that define the subfamily of RPTPγ and RPTPβ. The extracellular regions of RPTPγ and the two forms of RPTPβ (RPTPβ and dvRPTPβ) contain CAH-like domains (labeled CAH), FN type III repeats (labeled FN) and spacers of variable length characterized by a very low content of cysteine (indicated by thick lines). The conserved cysteine residues that flank the FN type III repeat are marked. The cytoplasmic regions of RPTPγ and RPTPβ contain two typical phosphatase domains (labeled D1 and D2). A conserved Cys residue in the first phosphatase domain and an Asp residue that replaces the Cys residue in the second phosphatase domain are indicated. The potential cleavage site in RPTPγ and the 86 amino acid insert in RPTPβ (which is not present in the deletion variant, dvRPTPβ) are denoted.

5. DETAILED DESCRIPTION OF THE INVENTION

Through the use of recombinant DNA methods, the present inventors have identified novel mammalian receptor-type (transmembrane) protein tyrosine phosphatases (PTPase; EC 3.1.3.48). Human RPTPγ has 1445 amino acids. In view of its receptor-like structure, and the likelihood that it is part of a family, the inventors have termed this protein, RPTPγ (receptor protein tyrosine phosphatase-γ). The family is designated herein as the "RPTPs."

RPTPγ is composed of a putative extracellular domain, a single transmembrane domain and a cytoplasmic portion with two tandem catalytic tyrosine phosphatase domains. The extracellular domain contains a stretch of 266 amino acids with striking homology to the zinc-containing enzyme carbonic anhydrase (CAH) indicating that RPTP-γ together with RPTP-β (HPTPζ) represent a subfamily of RPTPs. The present inventors have further constructed a model for the CAH-like domain of RPTPγ based upon the crystal structure of CAH. Eleven of the 19 residues that form the active site of CAH appear conserved in RPTPγ. Yet, only one out of the three His residues that ligate the zinc atom and are required for catalytic activity is conserved. Thus, the CAH-like domain of RPTPγ may have functions other than catalysis of hydration of metabolic $CO_2$.

The gene encoding RPTPγ is was mapped to human chromosome $3_p14.2-_p21$, in a region found to be deleted in certain types of renal and lung carcinomas. This led the present inventors to conclude that RPTPγ may function as a tumor suppressor gene in such cancers (See, also, LaForgia et al., *Proc. Natl. Acad. Sci* 88:5036–5040 (1991)).

The cDNA cloning of human RPTPγ and the complete DNA and amino acid sequences of human RPTPγ and its murine homologue are described herein. Northern analysis has been used to identify the natural expression of the protein in various cells and tissues. A partial cDNA clone of the catalytic domain of RPTPγ/HPTPγ has been previously described (commonly assigned U.S. patent application Ser. No. 07/654,188, from which the present application claims priority) Kaplan et al., *Proc. Natl. Acad. Sci.* 87:7000–7004 (1990), Krueger et al., *EMBO J.* 9:3241–3252 (1990)).

RPTPγ was shown to be expressed in anatomically distinct regions of rat brain and its expression was found to be developmentally regulated.

Remarkably, in addition to being composed of intracellular domains having enzymatic activity, the receptor family to which RPTPs belong includes transmembrane proteins having and N-terminal extracellular domains, analogous to the tyrosine kinase enzyme family (Tonks, N. K. et al. (1988) *Biochemistry* 27:8695–8701; Charbonneau, H. et al. (1988) *Proc. Natl. Acad. Sci. USA* 85:7182–7186; Streuli, M. et al. (1988) *J. Exp. Med.* 168:1523–2530; Streuli, M. et al. (1989) *Proc. Natl. Acad. Sci. USA* 86:8698–8702). The present inventors have therefore concluded that ligands in the extracellular environment can control the activity of this membrane-associated subclass of PTPases.

RPTPγ is useful in methods for screening drugs and other agents which are capable of activating or inhibiting the PTPase enzymatic activity, and thereby affecting major pathways of cellular metabolism. By attaching an intact RPTPγ, or the ligand-binding portion thereof, to a solid phase matrix, an affinity probe is created which can be used to screen biological products or chemical agents for their capacity to interact with the receptor on the basis of their binding activity. Bound material can then be eluted from the affinity probe in purified form.

Methods for coupling proteins and peptides to a solid phase matrix or carrier, the solid phase matrix materials useful in these methods, and means for elution, are well known to those of skill in the art.

The RPTPγ protein, or derivatives thereof having enzymatic activity, can be used for testing agents or compounds capable of enhancing or inhibiting the phosphatase activity.

The ability of a compound under test to modify phosphatase activity can be tested in an in vitro system wherein the test compound is added to purified RPTPγ protein, or an enzymatically active derivative thereof, and the effects on enzyme activity measured using standard enzymological procedures well known to those of skill in the art.

Alternatively, the action of a compound on RPTPγ enzymatic activity can be measured in a whole cell preparation using live or fixed cells, or a membrane fraction derived from live or fixed cells. This method is useful for screening compounds acting via the extracellular receptor portion of the protein, as well as compounds acting directly on the enzymatic portion of the protein. A test compound is incubated with cells, or with a membrane preparation derived therefrom, which express high amounts of RPTPγ, such as transfected COS or NIH-3T3 cells. The amount of cellular phosphotyrosine is then measured, using methods well-known in the art (Honegger, A. M. et al., *Cell* 51:199–209 (1987); Margolis, B. et al., *Cell* 57:1101–1107 (1989)). The results are compared to results obtained in the absence of the test compound, or in the absence or presence of a known activator of RPTPγ enzymatic activity. In such studies, the action of the test compound in the presence of an activator of tyrosine kinase can also be measured. A compound which stimulates RPTPγ enzymatic activity will result in a net decrease in the amount of phosphotyrosine, whereas a compound which inhibits RPTPγ enzymatic activity will result in a net increase in the amount of phosphotyrosine.

In the case of growth factor receptors which are tyrosine kinases, such as the receptors for epidermal growth factor (EGF) and for platelet-derived growth factor (PDGF), tyrosine phosphorylation is linked to cell growth and to oncogenic transformation. Activation of a PTPase, leading to dephosphorylation, would serve as a counterregulatory mechanism to prevent or inhibit growth, and might serve as an endogenous regulatory mechanism against cancer. Thus, mutation or dysregulation of this receptor/enzyme system may promote susceptibility to cancer The insulin receptor is also a tyrosine kinase, and phosphorylation of tyrosine in cells bearing insulin receptors would be associated with normal physiological function. In contrast to the case of cell growth and cancer, activation of an RPTP would counteract insulin effects. Subnormal RPTP levels or enzymatic activity would act to remove a normal counterregulatory mechanisms. Perhaps more important, though, over-activity, or inappropriate activation, of an RPTP, such as RPTPγ, would be expected to partially or totally inhibit the action of insulin on cells, leading to diabetes (of an insulin-resistant variety). Thus, susceptibility to diabetes may be associated with RPTPγ dysregulation.

Therefore, the methods of the present invention for identifying normal or mutant genes encoding RPTPγ, or for measuring the amount or activity of RPTPγ associated with a cell or tissue, can serve as methods for identifying susceptibility to cancer, diabetes, or other diseases associated with alterations in cellular phosphotyrosine metabolism.

The present invention provides methods for evaluating the presence of, and the level of, normal or mutant RPTPγ in a cell or in a subject. Absence, or more typically, low expression of the RPTPγ, or presence of a mutant RPTPγ, in an individual may serve as an important predictor of susceptibility to oncogenic transformation and the development of cancer. Alternatively, over-expression of RPTPγ, possibly due to a mutant receptor/enzyme system insensitive to negative regulation, or due to overabundance of a stimulatory ligand in the body, may serve as an important predictor of susceptibility to diabetes.

An oligonucleotide probe corresponding to a DNA sequences encoding a part of RPTPγ (see below) is used to test cells from a subject for the presence of DNA or RNA sequences encoding the RPTPγ A preferred probe would be one directed to the nucleic acid sequence encoding at least 4 amino acid residues, and preferably at least 5 amino acid residues, of the RPTPγ. Qualitative or quantitative assays can be performed using such probes. For example, Northern analysis (see Section 7, below) is used to measure expression of an RPTPγ mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al., *MOLECULAR CLONING: A LABORATORY MANUAL*, Second Edition, Cold Spring Harbor Press, Cold Spring Harbor, N.Y. (1989), which references are herein incorporated by reference).

An in vitro enzymatic method which is capable of increasing the concentration of such desired nucleic acid molecules is called the "polymerase chain reaction or "PCR" (Mullis, K. et al., *Cold Spring Harbor Symp. Quant. Biol.* 51:263–273 (1986); Erlich, H. et al., EP 50424, EP 84796, EP 258017, EP 237362; Mullis, K., EP 201184; Mullis, K. et al., U.S. Pat. No. 4,683,202; Erlich, H., U.S. Pat. No. 4,582,788; and Saiki, R. et al., U.S. Pat. No. 4,683,194).

The PCR provides a method for selectively increasing the concentration of a particular nucleic acid sequence even when that sequence has not been previously purified and is present only in a single copy in a particular sample. The method can be used to amplify either single- or double-stranded DNA. The method uses two oligonucleotide probes to serve as primers for the template-dependent, polymerase mediated replication of a desired nucleic acid molecule.

The precise nature of the two oligonucleotide probes of the PCR method is critical to the success of the method. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes are selected such that they contain sequences identical to, or complementary to, sequences which flank the particular nucleic acid sequence whose amplification is desired. More specifically, the oligonucleotide sequence of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

PCR reaction conditions are cycled between (a) those conducive to hybridization and nucleic acid polymerization, and (b) those which result in the denaturation of duplex molecules. In the first step of the reaction, the nucleic acids of the sample are transiently heated, and then cooled, in order to denature any double-stranded molecules. The "first" and "second" probes are then added to the sample at a concentration which greatly exceeds that of the desired nucleic acid molecule. Upon incubation under conditions conducive to hybridization and polymerization, the "first" probe will hybridize to the sample nucleic acid molecule at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. For reviews of the PCR, see: Mullis, K. B., *Cold Spring Harbor Symp. Quant. Biol.* 51:263–273 (1986); Saiki, R. K. et al. *BioTechnology* 3:1008–1012 (1985); Mullis, K. B. et al. *Meth. Enzymol.* 155:335–350 (1987).

In one embodiment, the present invention is directed to a naturally occurring mammalian RPTPγ. In another embodiment, the present invention is directed to a recombinant mammalian RPTPγ. The preferred mammalian RPTPγ of the present invention is of human origin. The invention provides the naturally occurring molecule substantially free of other proteins with which it is natively associated. "Substantially free of other proteins or glycoproteins" indicates that the protein has been purified away from at least 90 per cent (on a weight basis), and from even at least 99 per cent if desired, of other proteins and glycoproteins with which it is natively associated, and is therefore substantially free of them. That can be achieved by subjecting the cells, tissue or fluid containing the RPTPγ to standard protein purification techniques such as an immunoabsorbent column bearing an antibody specific for the protein. Other forms of affinity purification utilize solid-phase substrates which bind the RPTP's enzymatic domain, or a ligand that will bind to the receptor domain. Alternatively, the purification can be achieved by a combination of standard methods, such as ammonium sulfate precipitation, molecular sieve chromatography, and ion exchange chromatography.

It will be understood that the RPTPγ of the present invention can be biochemically purified from a variety of cell or tissue sources. For preparation of naturally occurring RPTPγ, tissues such as mammalian brain, especially of human origin, are preferred.

Alternatively, because the gene for the RPTPγ can be isolated or synthesized, the polypeptide can be synthesized substantially free of other mammalian proteins or glycoproteins in a prokaryotic organism or in a non-mammalian eukaryotic organism, if desired. As intended by the present invention, a recombinant RPTPγ molecule produced in mammalian cells, such as transfected COS, NIH-3T3, or CHO cells, for example, is a protein with the naturally occurring amino acid sequence or is a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support.

The present invention provides any of a number of "functional derivatives" of the RPTPγ. By "functional derivative" is meant a "fragment," "variant," "analog," or "chemical derivative" of the RPTPγ, which terms are defined below. A functional derivative retains at least a portion of the function of the RPTPγ, such as (a) binding to a specific antibody, (b) phosphatase enzymatic activity, or (c) binding of the extracellular "receptor" domain to a ligand, which permits its utility in accordance with the present invention.

A "fragment" of the RPTPγ refers to any subset of the molecule, that is, a shorter peptide.

A "variant" of the RPTPγ refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication EP 75444).

At the genetic level, these variants ordinarily are prepared by site-directed mutagenesis (as exemplified by Adelman et al., *DNA* 2:183 (1983)) of nucleotides in the DNA encoding the protein or peptide molecule, thereby producing DNA encoding the variant, and thereafter expressing the DNA in recombinant cell culture. The variants typically exhibit the same qualitative biological activity as the nonvariant protein or peptide.

An "analog" of the RPTPγ refers to a non-natural molecule substantially similar to either the entire molecule or a fragment thereof.

A "chemical derivative" of the RPTPγ contains additional chemical moieties not normally a part of the peptide. Covalent modifications of the RPTPγ protein or of a peptide derived therefrom, are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri- 4-nitrophenol, or chloro-7-nitrobenzo-2-oxa-1,3-diazole.

Histidyl residues are derivatized by reaction with diethylprocarbonate, pH 5.5–7.0, because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3- butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues may be deamidated to the corresponding glutamyl and aspartyl residues, under mildly acidic conditions. Either form of these residues falls within the scope of this invention.

Derivatization with bifunctional agents is useful for cross-linking the protein or peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido- 1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the X-amino groups of lysine, arginine, and histidine side chains (T. E. Creighton, *Proteins: Structure and Molecule Properties,* W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences,* 16th ed., Mack Publishing Co., Easton, Pa. (1980)

This invention is also directed to an antibody specific for an epitope of RPTPγ, preferably, of human RPTPγ, and the use of such an antibody to detect the presence of, or measure the quantity or concentration of, the RPTPγ in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen, preferably the RPTPγ protein or glycoprotein, a peptide derived therefrom or an epitope thereof.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are known in the art (Cabilly et al, *Proc. Natl. Acad. Sci. USA* 81:3273–3277 (1984); Morrison et al., *Proc. Natl. Acad. Sci. USA.* 81:6851–6855 (1984); Boulianne et al., *Nature* 312:643–646 (1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066–1074 (1986); Robinson et al., International Patent Publication #PCT/US86/02269 (published 7 May 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988)). These references are hereby incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other hybrid clones expressing antibodies of identical specificity.

Accordingly, mAbs generated against RPTPγ may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an RPTPγ epitope.

The anti-Id mAbs thus have their own idiotypic epitopes, or "idiotopes" structurally similar to the epitope being evaluated, such as an epitope of RPTPγ.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of RPTPγ according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics. An "antigen" is a molecule or a portion of a molecule capable of being bound by an antibody which is additionally capable of inducing an animal to produce antibody capable of binding to an epitope of that antigen. An antigen may have one, or more than one epitope.

An antibody is said to be specific for an antigen because it reacts in a highly selective manner, with that antigen and not with the multitude of other antigens which are structurally distinct.

The antibodies or antibody fragments of the present invention may be used to quantitatively or qualitatively detect the presence of cells which express the RPTPγ protein. This can be accomplished by immunofluorescence techniques employing a fluorescently labeled antibody (see below) coupled with light microscopic, flow cytometric, or fluorimetric detection. For such methods, the antibody is preferably specific for an extracellular epitope of RPTPγ.

The antibodies (or fragments thereof) useful in the present invention may be employed histologically, as in immunofluorescence or immunoelectron microscopy, for in situ detection of RPTPγ. In situ detection may be accomplished by removing a histological specimen from a subject, and providing a labeled antibody or antibody fragment of the present invention to such a specimen, preferably by applying or overlaying the antibody over the specimen. Through the use of such a procedure, it is possible to determine not only the presence of RPTPγ but also its distribution in the examined tissue. Using the present invention, those of ordinary skill will readily perceive that any of a wide variety of histological methods (such as staining procedures) can be modified in order to achieve such in situ detection. Such assays for RPTPγ typically comprise incubating a biological sample, such as a biological fluid, a tissue extract, freshly harvested cells, or cells which have been incubated in tissue culture, in the presence of a detectably labeled antibody specific for RPTPγ, and detecting the antibody by any of a number of techniques well-known in the art.

The biological sample may be incubated with a solid phase support or carrier such as nitrocellulose, or other solid support which is capable of immobilizing cells, cell particles or soluble proteins. The support may then be washed with suitable buffers followed by treatment with the detectably labeled RPTPγ-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports or carriers include glass, polystyrene, polypropylene, polyethylene, dextran, nylon, amylases, natural and modified celluloses, polyacrylamides, and magnetite. The preferred carrier is totally insoluble in the solution in which the assay of the present invention takes place; partially soluble carriers well-known in the art may also be used. The support material may have virtually any possible structural configuration so long as the support-coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-RPTPγ antibody may be determined according to well-known methods. Those skilled in the art will be able to determine operative and optimal assay conditions for each determination by employing routine experimentation.

One of the ways in which the RPTPγ-specific antibody can be detectably labeled is by linking the antibody, or a second antibody which binds to the anti-RPTPγ antibody, to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect RPTPγ through the use of a radioimmunoassay (RIA) (see, for example, Work, T. S. et al., *Laboratory Techniques and Biochemistry in Molecular Biology*, North Holland Publishing Company, New York, 1978, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing a labeled second antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to a fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The presence of normally functioning RPTPγ in a subject can also be tested using direct enzymatic assays, for the tyrosine phosphatase activity. Such biochemical measurements can be performed in vitro, using purified enzymes, allowing precise measurements of enzyme activity, or with membrane preparations, or whole cells, where the net phosphotyrosine level is determined.

In additional embodiments of the present invention, a nucleic acid molecule, prefereably DNA, comprising a sequence encoding an RPTPγ protein and methods for expressing the DNA molecule are provided. One of ordinary skill in the art will know how to identify and clone additional RPTP molecules, of human or other mammalian species, which have sequence homology to the RPTPγ molecules described herein, using the genetic sequences and oligonucleotides of the present invention without undue experimentation. Furthermore, manipulation of the genetic constructs of the present invention allow the grafting of a particular ligand-binding receptor domain onto the transmembrane and catalytic portions of the RPTPγ resulting in chimeric molecules. Non-limiting examples of such chimeric molecules include RPTPγ wherein the receptor portion is an epidermal growth factor receptor, a fibroblast growth factor receptor, and the like. Genetically engineered chimeric receptors are known in the art (see, for example, Riedel, H. et al., *Nature* 324:628–670 (1986)).

Genetic constructs encoding RPTPγ, functional derivative thereof, and chimeric molecules such as those described above, can be used in gene therapy. An abnormal or dysfunctional RPTPγ, which results in disease, may be replaced by infusion or implantation of cells of the desired lineage (such as hemopoietic cells, neurons, etc.) transfected with DNA encoding normal RPTPγ. Alternatively, or additionally, cells carrying a chimeric RPTPγ having a receptor portion which binds a ligand of choice (e.g., EGF) can be used for such gene therapy.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101–141 (1978)), and procedures for constructing recombinant molecules can be found in Sambrook et al. (supra).

Oligonucleotides representing a portion of an RPTPγ are useful for screening for the presence of genes encoding such proteins and for the cloning of an RPTPγ gene. Techniques for synthesizing such oligonucleotides are disclosed by, for example, Wu, R., et al., supra.

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *Molecular Biology of the Gene,* 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using such "codon usage rules", a single oligonucleotide, or a set of oligonucleotides, that contains a theoretical "most probable" nucleotide sequence capable of encoding RPTPγ is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes RPTPγ.

The oligonucleotide, or set of oligonucleotides, containing the theoretical "most probable" sequence capable of encoding the RPTPγ fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the RPTPγ gene (Sambrook et al., supra).

A suitable oligonucleotide, or set of oligonucleotides, capable of encoding a fragment of the RPTPγ gene (or complementary to such an oligonucleotide) is identified as above and synthesized, using procedures well known in the art (Belagaje, R., et al., *J. Biol. Chem.* 254:5765–5780 (1979); Maniatis, T., et al., In: *Molecular Mechanisms in the Control of Gene Expression,* Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). DNA synthesis may be achieved using an automated synthesizers. The oligonucleotide probe or set is hybridized by means well known in the art, against a DNA or, more preferably, a cDNA preparation derived from cells which are capable of expressing the RPTPγ gene. Techniques of nucleic acid hybridization are disclosed by Sambrook et al. (supra), and by Hames, B. D., et al. (In: *Nucleic Acid Hybridization, A Practical Approach,* IRL Press, Washington, D.C. (1985)), which references are herein incorporated by reference. Techniques such as, or similar to, those described above have successfully enabled the cloning of genes for human aldehyde dehydrogenases (Hsu, L. C. et al., *Proc. Natl. Acad. Sci. USA* 82:3771–3775 (1985)), fibronectin (Suzuki, S., et al., *EMBO J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:(715–8719 (1985)).

In a alternative way of cloning the RPTPγ gene, a library of expression vectors is prepared by cloning DNA or, more preferably, cDNA (from a cell capable of expressing RPTPγ) into an expression vector. The library is then screened for members capable of expressing a protein which binds to an anti-RPTPγ antibody, and which has a nucleotide sequence that is capable of encoding a polypeptide that has the same amino acid sequence as all or part of RPTPγ. In this embodiment, DNA, or more preferably cDNA, is extracted and purified from a cell which is capable of expressing RPTPγ protein. The purified cDNA is fragmented (by shearing, endonuclease digestion, etc.) to produce a pool of DNA or cDNA fragments. DNA or cDNA fragments from this pool are then cloned into an expression vector in order to produce a genomic or cDNA library of expression vectors whose members each contain a unique cloned DNA or cDNA fragment.

An "expression vector" is a vector which (due to the presence of appropriate transcriptional and/or translational control sequences) is capable of expressing a DNA molecule which has been cloned into the vector and of thereby producing a peptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. If a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing RPTPγ in order to produce a prokaryotic genomic expression vector library. Procedures for preparing cDNA and for producing a genomic library are disclosed by Sambrook et al. (supra).

A DNA sequence encoding RPTPγ of the present invention, or encoding functional derivatives thereof, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is "capable of expressing" a polypeptide if it contains nucleotide sequences which contain transcriptional and translational regulatory information and such sequences are "operably linked" to a polypeptide coding sequence. An operable linkage is a linkage in which the regulatory DNA sequences and the coding sequence are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the coding sequence may be obtained by the above-described methods. This region may be retained for its transcriptional termination regulatory sequences, such as termination and polyadenylation. Thus, by retaining the 3'-region naturally contiguous to the DNA coding sequence, the transcriptional termination signals may be provided. Where the transcriptional termination signals are not satisfactorily functional in the host cell used to express the protein, then a 3' region functional in that host cell may be substituted.

Two DNA sequences (such as a promoter region sequence and a RPTPγ coding sequence) are said to be operably linked if the nature of the linkage between the two DNA sequences does not (1) result in the introduction of a frame-shift mutation, (2) interfere with the ability of the promoter to regulate the transcription of the RPTPγ coding sequence. A promoter region is operably linked to a DNA coding sequence if the promoter is capable of effecting transcription of the coding sequence. Thus, to express the protein, transcriptional and translational signals recognized by an appropriate host are necessary. In order to be "operably linked" it is not necessary that two sequences be immediately adjacent to one another.

A promoter is a double-stranded DNA (or RNA) molecule which is capable of binding to RNA polymerase and promoting the transcription of an "operably linked" nucleic acid coding sequence. As used herein, a "promoter sequence" is the sequence of the promoter which is found on that strand of the DNA (or RNA) which is transcribed by the RNA polymerase. A "promoter sequence complement" has a sequence which is the complement of the "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to transcribe from only one strand of a duplex DNA template. Strand selection is determined by the orientation of the promoter sequence, and determines the direction of transcription since RNA is only polymerized enzymatically by the addition of a nucleotide 5' phosphate to a 3' hydroxyl terminus.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984)) polymerases; the $P_R$ and $P_L$ promoters of bacteriophage λ (*The Bacteriophage Lambda,* Hershey, A. D., Ed., Cold Spring Harbor Press, Cold Spring Harbor, N.Y. (1973); *Lambda II,* Hendrix, R. W., Ed., Cold Spring Harbor Press, Cold Spring Harbor, N.Y. (1980)); the trp, recA, heat shock, and lacZ promoters of *E. coli;* the α-amylase (Ulmanen, I., et al., *J. Bacteriol.* 162:176–182 (1985)) and the σ- 28-specific promoters of *B. subtilis* (Gilman, M. Z., et al., *Gene* 32:11–20 (1984)); the promoters of the bacteriophages of Bacillus (Gryczan, T. J., In: *The Molecular Biology of the Bacilli,* Academic Press, Inc., NY (1982)); Streptomyces promoters (Ward, J. M., et al., *Mol. Gen. Genet.* 203:468–478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R. (*J. Ind. Microbiol.* 1:277–282 (1987)); Cenatiempo, Y. (*Biochimie* 68:505–516 (1986)); Watson, J. D. et al. (In: *Molecular Biology of the Gene,* Fourth Edition, Benjamin Cummins, Menlo Park, Calif. (1987)); and Gottesman, S. (*Ann. Rev. Genet.* 18:415–442 (1984)).

Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., Nature (London) 290:304–310 (1981)); and the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)). All of the above listed references are incorporated by reference herein.

Strong promoters are preferred. Examples of such preferred promoters are those which recognize the T3, SP6 and T7 polymerases, the $P_L$ promoter of bacteriophage λ, the recA promoter and the promoter of the mouse metallothionein I gene. A most preferred promoter for eukaryotic expression of RPTPγ is an SV40 promoter such as that driving transcription in the pLSV vector (Livneh, E., et al., (1986) *J. Biol. Chem.* 261, 12490–12497). The sequences of such polymerase recognition sites are disclosed by Watson, J. D. et al. (In: *Molecular Biology of the Gene,* Fourth Edition, Benjamin/Cummings Publishing Co., Inc., Menlo Park, Calif., (1987)).

Having now generally described the invention, the same will be more readily understood through reference to the following example which is provided by way of illustration, and is not intended to be limiting of the present invention, unless specified.

6. EXAMPLE: ISOLATION AND ANALYSIS OF RPTPγ cDNA CLONES

Resolving the issue as to whether or not RPTPγ may function as a tumor suppressor gene requires a detailed screening of tumors for genomic rearrangements and point mutations and reintroduction of wild type RPTPγ into tumor cells. Since, so far, the genomic analysis of RPTPγ was performed only with a partial sequence (Kaplan et al., *Proc. Natl. Acad. Sci.* 87:7000–7004 (1990)), the present inventors cloned and sequenced the full length human RPTPγ cDNA. In addition, the present inventors cloned the murine homologue of RPTPγ to facilitate an analysis of its tissue expression, as well as its normal in vivo function.

6.1. Library Screening

Human RPTPγ:

The initial clone was isolated from a λgt11 cDNA library of 1 day old human brainstem (obtained from the American Type Culture Collection-No. 37432), by screening approximately 300,000 plaques with a nick translated LCA probe, that spanned both conserved phosphatase domains, under relaxed hybridization conditions.

The rest of the cDNA clones were isolated by screening the human brainstem library with randomly primed probes from the previously isolated clones of RPTPγ under high stringency hybridization conditions.

Mouse RPTPγ:

The initial clone was isolated from a λgt11 mouse brain cDNA library (purchased from Clontech, Palo Alto, Calif.), by screening approximately one million plaques with a randomly primed probe from human RPTPγ that spanned all of the first catalytic domain, under high stringency hybridization conditions. The rest of the cDNA clones were isolated by screening the mouse brain library with probes from the previously isolated clones of mouse RPTPγ under high stringency hybridization conditions.

6.2. Nucleotide Sequence Determination

DNA preparations of λgt11 RPTPγ clones were digested with EcoRI and subcloned into BlueScript SK-plasmid (purchased from Stratagene La Jolla, Calif.). Nucleotide sequences were determined by the dideoxynucleotide chain termination method (Sequenase, United States Biochemical, Cleveland, Ohio) with specific synthetic oligonucleotides as primers. All the clones were sequenced on both strands.

6.3. Sequence Alignments

All DNA and protein data base searches were done with the Genetic Computer Group sequence analysis software package (Devereux et al., *Nucleic Acid Res.* 12:387–396 (1989)). The SwissProt and Gene Bank/European Molecular Biology Laboratory data bases were searched with FASTA and TFASTA, respectively (Pearson and Lipman, *Proc. Natl. Acad. Sci.* 85:2444–2448 (1988)). Proteins were aligned with the Genetics Computer Group programs, LINEUP, PILEUP, PRETTY and BESTFIT.

6.4. Results and Discussion

The nucleotide sequence of human RPTPγ (SEQ ID NO:1) is shown in FIG. 3. The complete amino acid sequences of human RPTPγ (SEQ ID NO:2) is shown in FIGS. 3 and 4. The amino acid sequence of murine RPTPγ (SEQ ID NO:3) is presented in FIG. 4. Translation of the cDNA sequences reveals the existence of an open reading frame of 1445 amino acids for human RPTPγ and 1442 amino acids for the murine homologue. The initiation Met in both human RPTPγ and the murine homologue are preceded by in frame stop codons. Both proteins contain a signal sequence (underlined in FIG. 4) and a putative extracellular domain of 736 amino acids for human RPTPγ and 733 amino acids for the murine gene. The extracellular domain of human RPTPγ contains eight putative N-linked glycosylation sites, six of which are conserved in the murine homologue (marked with arrowheads in FIG. 4).

The amino-terminal region of the extracellular domain of RPTPγ (residues 56–322) has a striking sequence similarity to the enzyme carbonic anhydrase (CAH). This CAH-like domain is preceded by four basic amino acids (Arg Arg Arg Lys) that resemble the cleavage site in the extracellular domain of the insulin receptor separating the α and β subunits (Ullrich et al., Nature. 313:756–761 (1985)). This sequence motif may function as a cleavage site for proteolytic enzymes (Barr, P. J., Cell. 66:1–3 (1991)); a similar cleavage site has been identified in the extracellular domain of another RPTP, LAR (Streuli et al., EMBO J. 11:897–907 (1992); Yu et al., Oncogene. 7:1051–1057 (1992)).

The CAH-like domain is followed by one fibronectin (FN) type III repeat, a motif found in many cell surface proteins. Alignment of the FN type III sequence of RPTPγ with typical FN type III repeats of other proteins is presented in FIG. 5. The remaining 293 amino acids of the extracellular domain are devoid of any Cys residues and can be subdivided into three regions:
(1) a Ser/Thr rich region in which 32% of the amino acids are Ser and Thr (residues 442 to 560), followed by
(2) a region composed of 90% charged and polar amino acids (residues 561–662), and
(3) a region with no similarity to any known sequence motif. Hence, the region downstream from the FN repeat may function as a spacer separating the CAH-like domain and the FN type III repeat from the transmembrane region.

The extracellular domain of RPTPγ is followed by a typical transmembrane domain of 23 amino acid residues. Like in most known RPTPs, the intracellular domain of RPTPγ contains two tandem phosphatase domains (Fischer et al., Science. 253:401–406 (1991)). It is noteworthy that the second phosphatase domain of RPTPγ has an Asp residue at position 1351 instead of a conserved Cys residue though to be essential for catalytic activity (Guan et al., J. Biol. Chem. 266:17026–17030 (1991); Pot et al., J. Biol. Chem. 267:140–143 (1992)). Interestingly, an Asp residue is also found in a similar position in RPTPβ (Kaplan et al., Proc. Natl. Acad. Sci. 87:7000–7004 (1990)) and in the Drosophila phosphatase 99A (Yang et al., Cell. 67:661–673 (1991); Tian et al., Cell. 67:675–685 (1991); Hariharan et al., Proc. Natl. Acad. Sci. 88:11266–11270 (1991)). Moreover, the second catalytic domain of RPTPγ contains an insert of 15 amino acids (residues 1299 to 1313) identical to the insert found in corresponding position in RPTPβ (Kaplan et al., Proc. Natl. Acad. Sci. 87:7000–7004 (1990)) and so far appears to be unique to these two phosphatases. This insert contains a Tyr residue in position 1308 which is preceded by two Asp residues and followed by a Val residue, suggesting that it may function as a phosphorylation site for tyrosine kinases.

Human RPTPγ and its murine homologue are 90% identical at the nucleotide level and 95% identical in the amino acid level and most of the differences are conservative substitutions (FIG. 4). The strikingly high conservation is found in both the cytoplasmic and extracellular domains. This degree of conservation between human and mouse RPTPγ is higher than in some of the other phosphatases such as the extracellular portion of RPTPα (Sapp et al., Proc. Natl. Acad. Sci. 87:6112–6116 (1990); Kaplan et al., Proc. Natl. Acad. Sci. 87:7000–7004 (1990), Krueger et al., EMBO J. 9:3241–3252 (1990); Matthews et al., Proc. Natl. Acad. Sci. 87:4444–4448 (1990)). The most conserved parts are the FN repeat (100% identity), the CAH-like domain (97% identity) and the Ser/Thr rich domain (97% identity). The rest of the extracellular domain is the least conserved (70% identity). It is noteworthy that the cluster of charged and polar amino acids that follows the Ser/Thr rich domain is found in both human and murine RPTPγ in spite of the lower degree of sequence conservation. The high degree of identity between the human and murine sequences in the CAH-like domain, the FN type III repeat and the Ser/Thr rich domain suggests that these regions are required for a conserved biological functions.

7. EXAMPLE: EXPRESSION OF MURINE RPTPγ

7.1. Tissue Expression and Northern Analysis

Poly A+ RNA was prepared from adult mouse tissues by oligo dT selection as described (Vennstrom et al., Cell. 28:135–143 (1982)), fractionated (5 µg per lane) on a formaldehyde-containing gel, transferred to nytran (Schleicher and Schuell) using standard procedures, and probed with mouse clones MB-8 and MB-122 that encompass all of the first phosphatase domain, the juxtamembrane domain, the transmembrane domain and the beginning of the extracellular portion of murine RPTPγ.

7.2. In Situ Hybridization

Fresh frozen rat tissue was cut on a cryostat into 20 µm thick sections and thaw-mounted onto gelatin-coated slides. The sections were fixed in 4% paraformaldehyde in 0.1M sodium phosphate (pH 7.4) for 30 min, rinsed 3 times for 5 minutes in 0.1M sodium phosphate (pH 7.4) for 30 min, rinsed 3 times for 5 minutes in 0.1M sodium phosphate and twice for 10 minutes in 2×SSC. Two different oligonucleotide probes were used in the hybridization analysis:
(1) a 51 base oligonucleotide complementary to a portion of the cytoplasmic domain; and
(2) a 52 base oligonucleotide complementary to a portion of the extracellular domain.

The oligonucleotides were labelled with [$^{35}$S]-dATP (NEN DuPont) using terminal deoxynucleotidyltransferase (Boeringer Mannheim) and purified using Sephadex G25® quick spin columns (Boeringer Mannheim). The specific activity of the labeled probes was between 5×10$^8$ to 1×10$^9$ cpm/µg. Prehybridization and hybridization were carried out in a buffer containing 50% deionized formamid, 4×SSC, 1×Denhardtxs solution, 500 µg/ml denatured salmon sperm DNA, 250 µg/ml yeast tRNA and 10% dextran sulfate. The tissue was incubated for 12 hours at 45° C. in hybridization solution containing the labelled probe (1×10$^6$ cpm/section) and 10 mM dithiothreitol (DTT). Controls for specificity were performed on adjacent sections by adding 30-fold concentration of the unlabeled oligonucleotide or by hybridization with the sense probe. After hybridization the sections were washed in two changes of 2×SSC at room temperature for 1 h, 1×SSC at 55° C. for 30 min, 0.5×SSC at 55° C. for 30 min and 0.5×SSC at room temperature for 15 min and dehydrated in 60%, 80% and 100% ethanol. After air drying, the sections were exposed to x-ray film for 5–10 days.

7.3. Results and Discussion

Northern blot analysis showed that RPTPγ is widely expressed in different murine tissues (FIG. 1). Two major RPTPγ transcripts of 5.5 and 8.5 kb were detected in brain, lung, kidney, heart, skeletal muscle, liver, spleen and testes.

An additional shorter transcript of approximately 3.0 kb was detected in testes.

Two RPTPs which are structurally related to RPTPγ are RPTPβ/HPTPζ (Krueger et al., *Proc. Natl. Acad. Sci.* 89:7417–7421 (1992) and a drosophila phosphatase DPTP99A (Tian et al., *Cell.* 67:675–685 (1991); Yang et al., *Cell.* 67:661–673 (1991), Hariharan et al., *Proc. Natl. Acad. Sci.* 88:11266–11270 (1991)). Since these phosphatases are specifically expressed in the central nervous system, the expression pattern of RPTPγ in the brain of newborn and adult rats as analyzed by in situ hybridization.

Figure 2A:
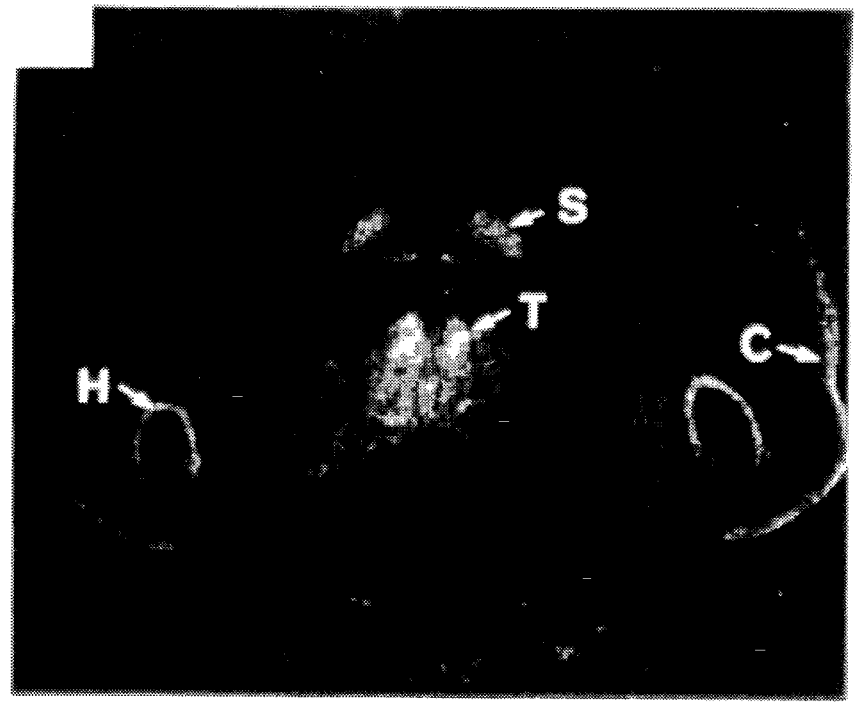
Figure 2B:
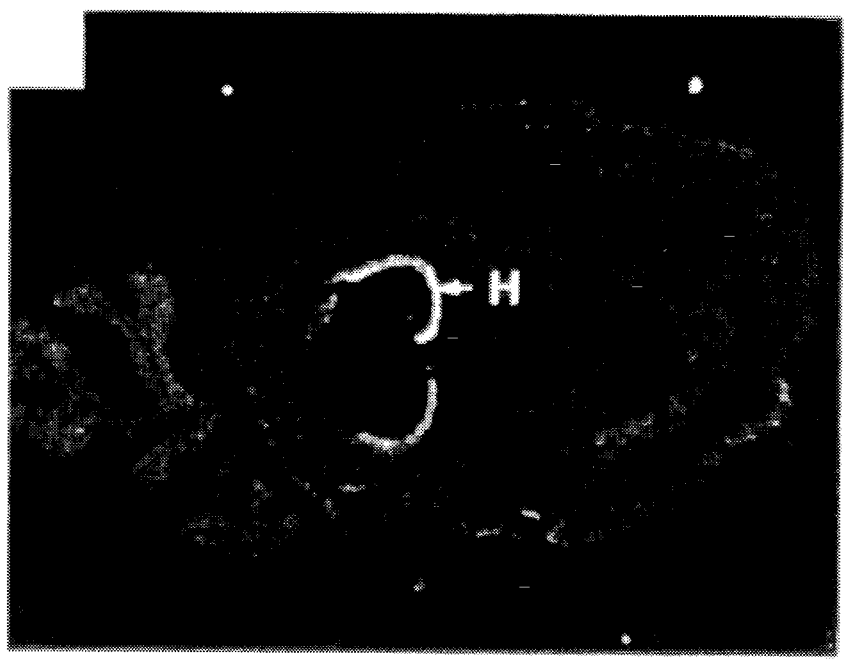
Figure 7A:
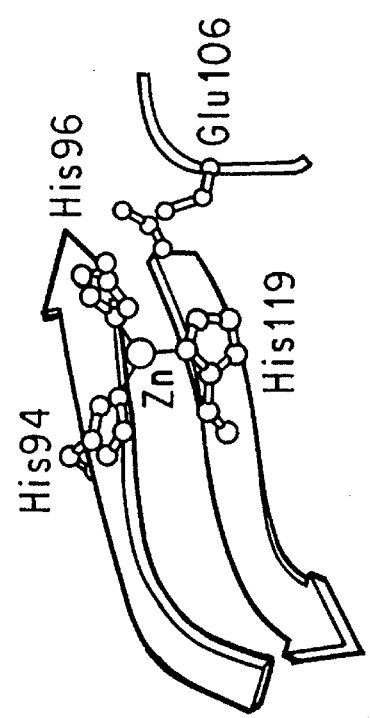
Figure 7B:
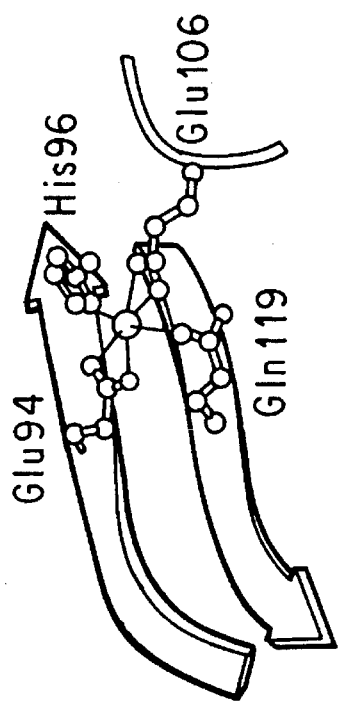
Figure 7C:
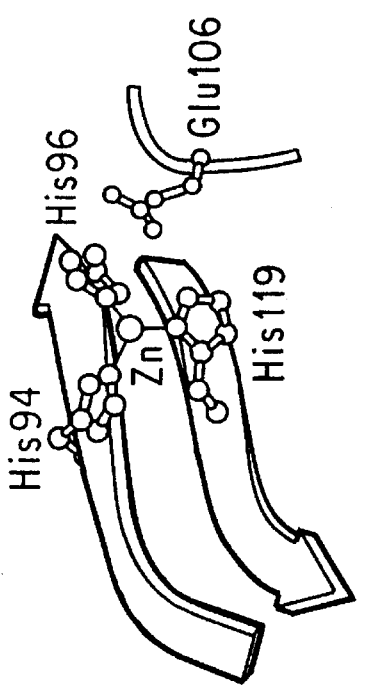
Figure 7D:
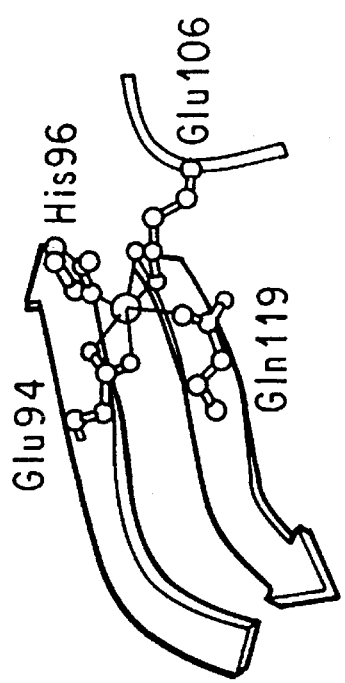

In newborn rat, the highest level of expression was detected in the hippocampal formation, in the septal and midline thalamic nuclei and in the cortex (FIG. 2A). However, in the adult rat brain, RPTPγ was highly expressed in the hippocampal formation (FIG. 2B), but not in the septal and midline thalamic nuclei and in the cortex. Hybridization with probes derived from either the cytoplasmic or the extracellular domain gave similar results. The addition of a 30-fold concentration of unlabeled oligonucleotides completely blocked the labeling in all areas. Furthermore, no signal was observed in adjacent sections hybridized with the sense probe. These results demonstrate that the two probes hybridize to mRNA in a sequence-specific manner.

The transient expression in the septal and midline thalamic nuclei and in the cortex of the newborn rat brain indicated that the expression of RPTPγ is developmentally regulated and may play a role in the development of these regions.

It is noteworthy that the patterns of expression of RPTPγ and the closely related RPTPβ are totally different. In the embryo, RPTPβ is expressed in the ventricular and subventricular zones of the brain and spinal cord. In the adult brain, RPTPβ is expressed in the Purkinje cell layer of the cerebellum, the dentate gyrus and the subependymal layer of the anterior horn of the lateral ventricle.

8. EXAMPLE: CHROMOSOMAL LOCALIZATION OF THE MURINE RPTPγ GENE

To define the genetic locus encoding mouse RPTPγ, a probe that contains the first catalytic domain of mouse RPTPγ was used to search for a restriction fragment length variants among inbred stains of mice. Southern blotting analysis of TaqI-digested DNA revealed two DNA fragments, of 2.9 and 1.8 kb, shared by all strains examined plus a fragment of either 2.7 kb (C3H/HeJ, DBA/2J) or 2.0 kb (all other strains examined). The inheritance of this DNA variant in the AKXD, BXD and BXH recombinant inbred strains of mice defined a genetic locus linked to Odc-9 (eight recombinants among 61 strains) and Plau (eleven recombinants among 49 strains) near the centromeric end of the linkage map of chromosome 14 (Table I). The present inventors proposed the designation Ptpg (phosphotyrosine phosphatase gamma) as the symbol for the locus, consistent with the symbol Ptpa previously assigned for mouse RPTPα (Sapp et al., *Proc. Natl. Acad. Sci.* 87:6112–6116 (1990)).

TABLE I

DNA Fragment Length Variant Associated with the Murine RPTPγ I Gene a Allele (TaqI fragment of 2.7 Kb):

Mouse Strains

Inbred: DBA/2J, C3H/HeJ
Recombinant Inbred:

AKXD-2, 3, 6, 8, 11, 12, 15, 20, 22, 23, 26, 27
BXD-5, 8, 9, 14, 15, 16, 18, 21, 22, 24, 29, 31, 32
BXH-2, 3, 4, 9, 12, 14, 19 b Allele (TaqI fragment of 2.0 Kb):

Mouse Strains

Inbred: C57BL/6J. 020/A, AKR/J, C57L/J, SWR/J, SJL/J, BALB/cJ, STS/A
Recombinant Inbred:

AKXD-1, 7, 9, 10, 13, 14, 16, 18, 21, 24, 28
BXD-1, 2, 6, 11, 12, 13, 19, 20, 23, 25, 27, 28, 30
BXH-6, 7, 8, 10, 11

10 μg quantities of liver or spleen genomic DNA were digested with TaqI enzyme and analyzed by Southern blotting with a probe from the first catalytic domain of murine RPTPγ.

9. EXAMPLE: ANALYSIS OF RPTPγ STRUCTURE AND MODELING OF CARBONIC ANHYDRASE DOMAIN

9.1. Modeling of the Carbonic Anhydrase Domain and Energy Minimization

After alignment of the carbonic anhydrase (CAH) domain of RPTPγ with the sequences of the soluble CAHs, the corresponding substitutions, deletions and insertions were performed on an Evans & Sutherland and Silicon Graphic interactive displays, using the 'mutate' options provided in the program 'O' (Jones et al., *Acta. Crystallogr.* A47:110–119 (1991)). Inserted peptides and peptides flanking deleted segments were given an initial conformation which best fitted similar peptides taken from proteins with known 3-D structures and which are stored in the program as a data bank of conformational information. The initial side chain conformations of inserted and substituted residues were selected according to the rotamers library of Ponder & Richards (Ponder et al., *J. Mol. Biol.* 193:775–791 (1987)). This rebuilt model was subjected to several cycles of energy-minimization using the program "X-Plor" (Brunger, A. T., "X-Plor (Version 3.0), Manual," Yale University, New Haven, Conn. (1992)) and the energy parameter sets param19.pro and toph19.pro of the program CHARM (Brooks et al., *J. Comput. Chem.* 4:187–217 (1983)). Cα atoms were constrained to remain close to their original positions in the CAH structure. The rms deviation between the main-chain atoms in the model thus derived and the original carbonic anhydrase structure is 0.7 Å. All the Phi/Psi angles of the resulting model fall within the allowed regions of the Ramachandran plot.

9.2. Results and Discussion

As described above, the amino terminal region of the extracellular domain of RPTPγ contains a region of 266 amino acids with a striking sequence similarity to the enzyme (CAH). CAH enzymes catalyze the hydration of metabolic $CO_2$ or the dehydration of $HCO_3^-$ in the following reaction:

$CO_2 + H_2O \rightleftharpoons H^+ + HCO_3^-$

CAHs are ubiquitously expressed enzymes with extremely efficient turnover rates of $10^6\ S^{-1}$ for $CO_2$ hydration. They hydrolyze certain esters and hydrate specific aldehydes. All CAHs are zinc metalloenzymes in which the zinc atom is required for the catalytic activity. Seven types of CAH have been identified so far (reviewed in Tashian, R. E., *BioEssays* 10:186–192 (1989)). These include:

(a) the cytoplasmic enzymes CAH-1,2 and 3,
(b) an extracellular glycoprotein CAH-4,
(c) a mitochondrial enzyme CAH-5,
(d) a secreted enzyme CAH-6, and
(e) a membrane-bound enzyme CAH-7.
(f) In addition, vaccina virus also contains a transmembrane protein with a CAH-like domain in its extracellular portion.

Figure 6A:
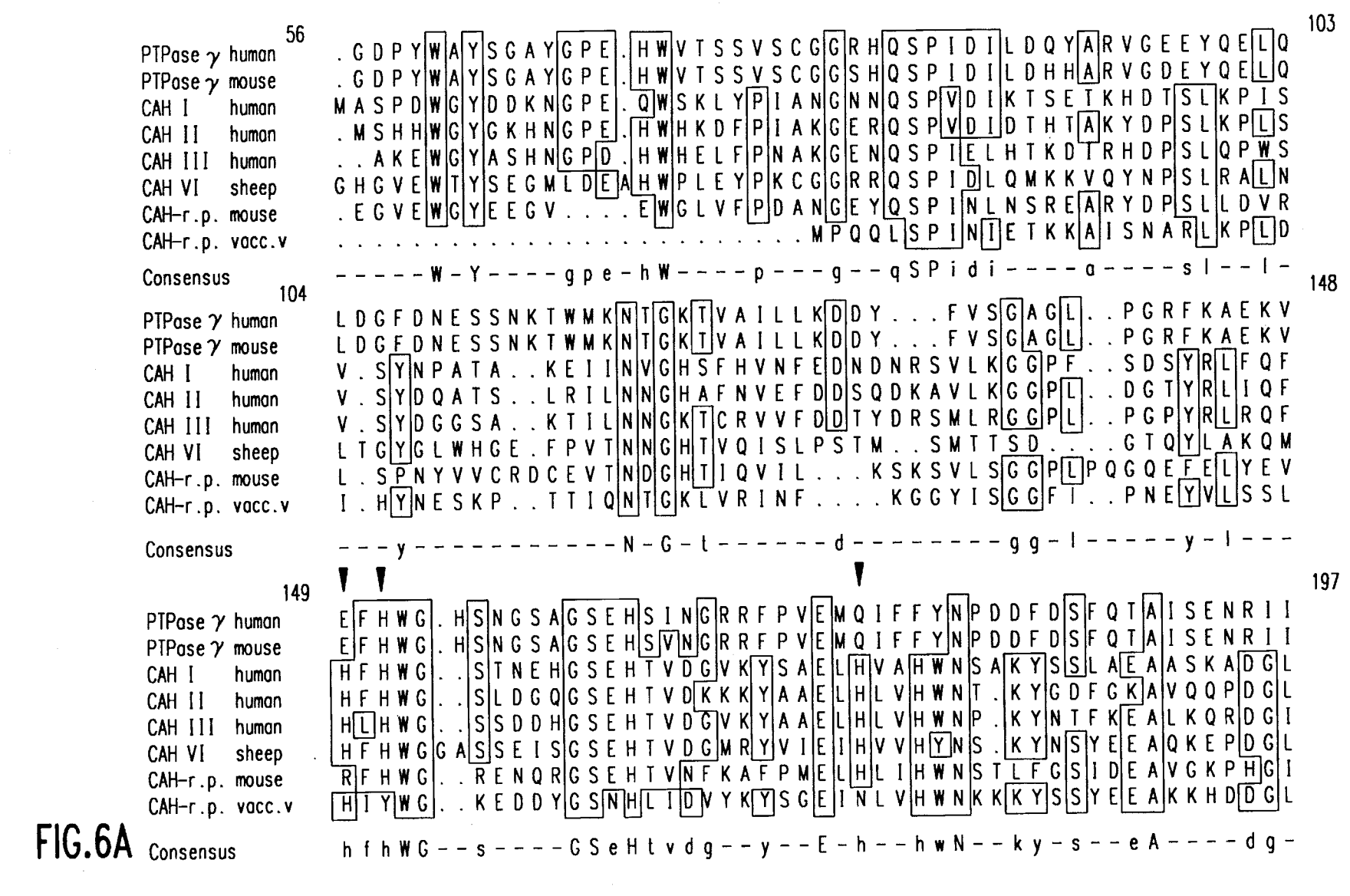
Figure 6B:
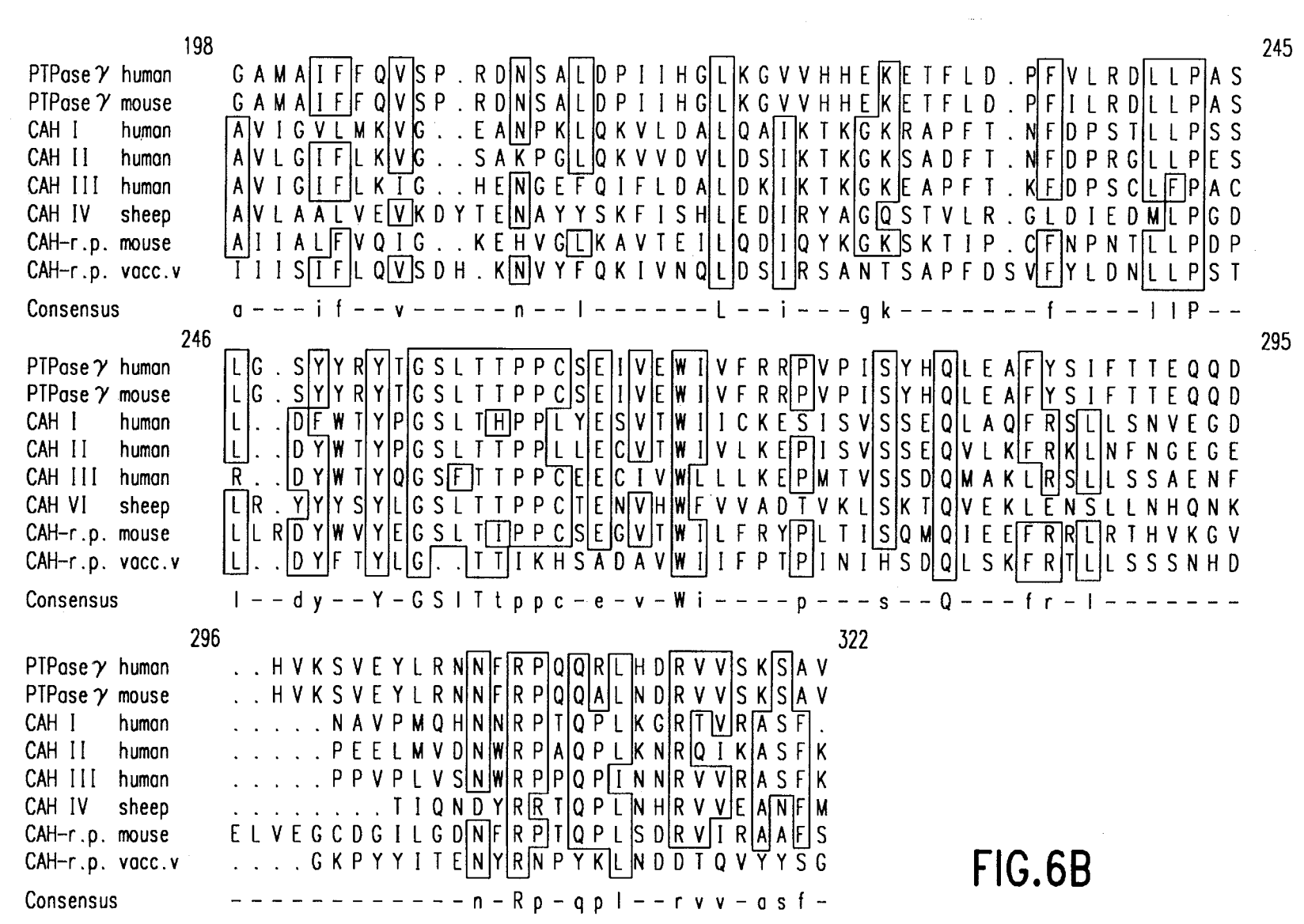

The CAH-like domains in human and murine RPTPγ were aligned with the amino acid sequences of the different forms of CAH (FIG. 6A). Comparison of the sequences revealed clusters of identical amino acids that usually match regions of high conservation of sequences between the different forms of CAH. Very few insertions and deletions were required to align the CAH domain of RPTPγ to that of the different CAHs. It is noteworthy that 11 of the 19 residues that form the active site of CAH (Ericksson et al., *Proteins.* 4:274–282 (1988)) are also found in RPTPγ. Of the three His residues that ligate the zinc atom in CAH (indicated with arrowheads in FIG. 6A) only one His in position 151 is conserved in RPTPγ, whereas the other two are replaced by Glu and Gln residues (positions 149 and 175, respectively). The CAH domain of RPTPγ shares 35–40% sequence identity with all known CAHs (FIG. 6B).

On the basis of the striking sequence similarity of this region with CAHs, the present inventors constructed a model for the structure of this region in RPTPγ by substitution of amino acids from the RPTPγ sequence into equivalent positions in the known three dimensional crystal structure of CAH (Ericksson et al., *Proteins.* 4:274–282 (1988); entry 1ca2 in the Brookhaven Protein Data Bank). This was followed by energy minimization in which the Cα atoms were restrained to their positions in the original CAH structure. In the absence of direct structural evidence, it is difficult to assess the precision of the resulting model, but three features point strongly to its relevance to the actual folding of the RPTPγ domain.

First, all the deletions and insertions in RPTPγ relative to the CAH sequence map to surface regions. All but one fall in stretches of the polypeptide chain lacking any well defined secondary structure. Thus, all these differences can be accommodated without distorting the original model.

Second, substitutions of internal residues in the RPTPγ domain follow a pattern that preserves the tight packing of the two hydrophobic cores in CAH (Ericksson et al., *Proteins.* 4:274–282 (1988)), as is often encountered in families of homologous proteins (Bordo et al., *J. Mol. Biol.* 211:975–988 (1990)). Replacements of some aromatic residues in CAH by aliphatic ones in the RPTPγ domain (Phe 66 to Val 124, Phe 70 to Leu 128, Phe 93 to Val 148 and Phe 176 to Leu 233) reduce somewhat the aromatic character of the hydrophobic core proximal to the zinc binding site (Ericksson et al., *Proteins.* 4:274–282 (1988)). Despite these differences, the tight packing is maintained through the substitutions (CAH to RPTPγ): Ile 59 to Trp 116, Val 160 to Ile 217 and Ser 56 Asn.

Third, inspection of the sequence of the CAH domain of murine RPTPγ revealed that substitutions relative to the human gene also followed the pattern of conservation of a tightly packed hydrophobic core, for example, Ile 165 in human RPTPγ to Val in murine RPTPγ and Val 237 in human RPTPγ to Ile in murine RPTPγ).

Particularly intriguing is the fate of the zinc binding site and the active site of CAH in the RPTPγ domain. Sequence alignment shows that two of the conserved His residues ligating the zinc in all known CAHs have been replaced in RPTPγ (His 94 to Glu 149, His 119 to Gln 175). Inspection of zinc binding sites in proteins with known three-dimensional structure (Vallee et al., *Biochemistry* 29:5647–5659 (1990)) reveals that none of them contains Gln. Furthermore, loss of zinc binding capability as a result of a His to Gln mutation was reported in the growth hormone family (Cunningham et al., *Science.* 250:1709–1712 (1990)). Moreover, inspection of the energy minimized model of the CAH domain of RPTPγ suggests that the residues Glu 149, His 151, Glu 162 and Gln 175 can form a planar constellation of atoms (FIG. 7) that is often found in the binding sites of octahedrally coordinated transition metals such as manganese (Hardman, K. D. et al., *J. Molec. Biol.* 157:69–86 (1982).

A CAH-like domain was also found in the amino terminal region of RPTPβ/HPTPζ (co-pending commonly assigned U.S. patent application Ser. No. 07/654,188, filed Feb. 26, 1991, from which the present application claims priority; co-pending commonly assigned U.S. Ser. No. 08/015,973, filed Feb. 10, 1993, titled "Novel Receptor-Type Phosphotyrosine Phosphatase-Beta) Krueger et al., *Proc. Natl. Acad. Sci. USA* 89:7417–7421 (1992). It appears that the salient features of the CAH-like domain in RPTPγ, such as the tightly packed hydrophobic core and the replacement of two of the three conserved His residues, are also observed in the CAH domain of RPTPβ. This similarity may reflect functional parallels between these two domains. The biological role of the CAH domains of RPTPγ and RPTPβ is not known. In view of the fact that only 1 of 3 His residues that ligate zinc and are crucial for CAH activity is conserved, it is conceivable that the CAH domains of RPTPγ and RPTPβ may not have the ability to bind zinc. It is possible, however, that the site occupied by zinc in CAH will be capable of binding other transition metals and thus have a function other than hydration of metabolic $CO_2$.

Interestingly, the homology between RPTPγ and RPTPβ extends into the downstream FN type III repeat which is flanked in both proteins by two conserved Cys residues. An alignment of the sequences of these two domains in RPTPγ and RPTPβ (FIG. 8A) shows approximately 37% sequence identity. The FN type III repeat in RPTPγ is followed by a stretch of 293 amino acids that is characterized by a lack of Cys residues and thus may serve as a spacer that separates the CAH-like domain and the FN repeat from the transmembrane domain.

Two forms of RPTPβ have been identified both of which contain intact CAH-like domains and fibronectin type III repeats followed by a Cys free region. The two forms of RPTPβ differ in the length of the Cys free spacer, which contains 1048 amino acids in the long form and 384 amino acids in the deletion variant (dvRPTPβ). As mentioned earlier, the similarity between RPTPγ and RPTPβ extends to the cytoplasmic domains of RPTPγ and RPTPβ (see co-pending commonly assigned U.S. patent application Ser. No. 08/015,973, filed Feb. 10, 1993, titled "Novel Receptor-Type Phosphotyrosine Phosphatase-Beta").

Figure 8B:
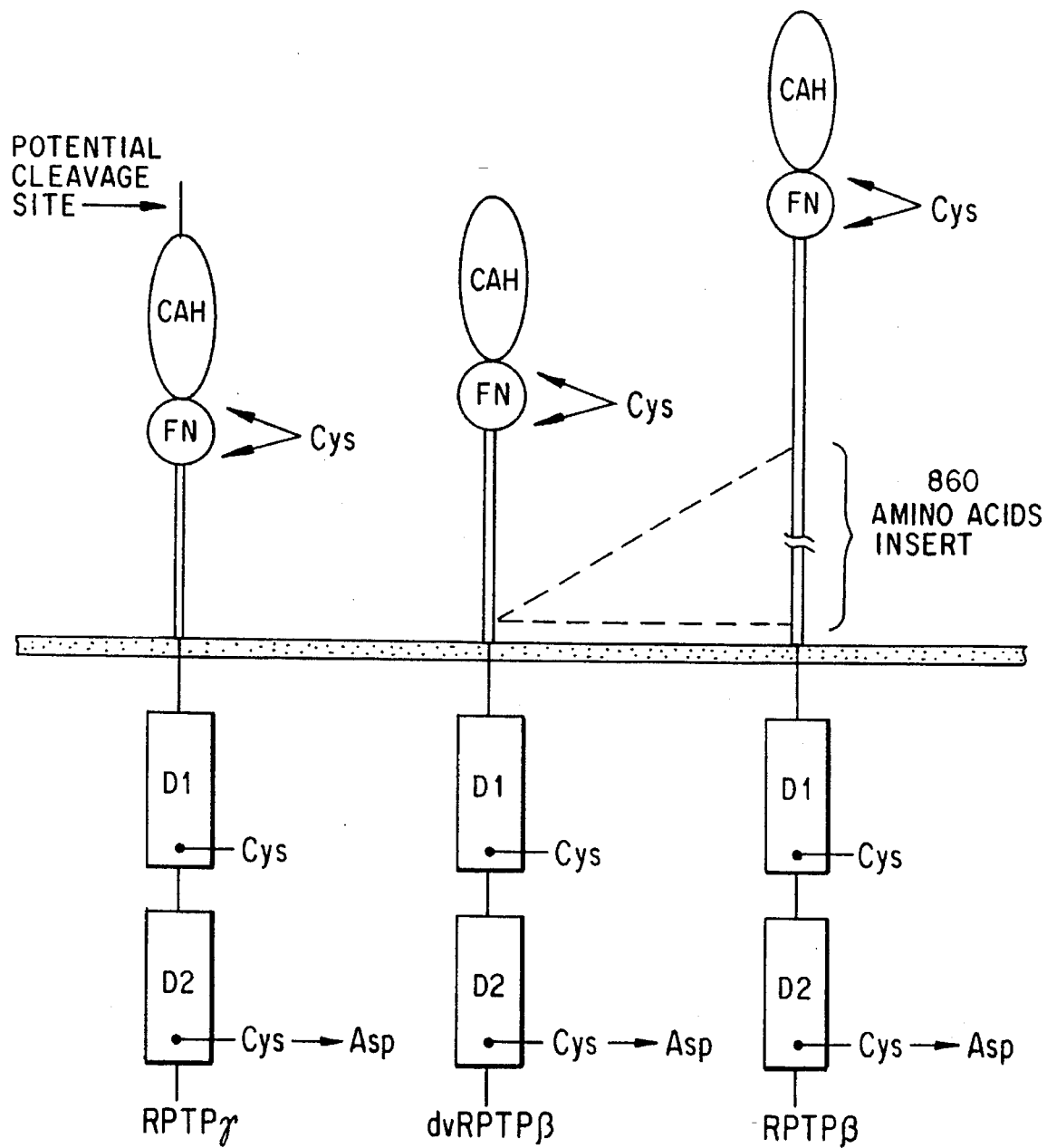

On the basis of these similarities, it is suggested that these two phosphatases define a new subfamily of RPTPs (FIG. 8B). The elucidation of the biological function of RPTPγ and RPTPβ and the role of the CAH-like domain in these proteins may require the identification of their putative natural ligands and the binding region of these orphan receptors.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated nucleic acid molecule having a nucleotide sequence of SEQ ID NO: 1.

2. An isolated nucleic acid molecule comprising a nucleotide sequence that (a) encodes a polypeptide having the amino acid sequence SEQ ID No: 2 or SEQ ID No: 3; or (b) is the complement of the nucleotide sequence of (a).

3. An isolated nucleic acid molecule comprising a nucleotide sequence that hybridizes under highly stringent conditions to the nucleic acid molecule of claim 2 and encodes a naturally occurring receptor-type protein tyrosine phosphatase-γ.

4. A nucleic acid molecule comprising a nucleotide sequence that encodes (a) a receptor-type protein tyrosine phosphatase-γ having the amino acid sequence of SEQ ID No: 2 and lacks one of the following segments of amino acid residues: 1–20, 21–53, 54–1445, 56–322, 347–441, 442–735, 21–763, 737–1445, 737–762, 21–873, 874–1118, 1175–1409, 874–1409 or 1410–1445; or (b) the complement of the nucleotide sequence of (a).

5. A nucleic acid molecule comprising a nucleotide sequence that encodes (a) a polypeptide having an amino acid sequence of SEQ ID No: 2 from amino acid residues 54–1445, 56–322, 347–441, 442–735, 1–736, 20–736, 763–1445, 874–1118, 1175–1409, or 874–1409; or (b) the complement of the nucleotide sequence of (a).

6. The nucleic acid molecule of claim 2 or 3 which is a cDNA.

7. The nucleic acid molecule of claim 2 or 3 which is a genomic DNA.

8. A recombinant vector containing the nucleotide sequence of claim 2, 3, 4 or 5.

9. An expression vector containing the nucleotide sequence of claim 2, 3, 4, or 5 operatively associated with a regulatory nucleotide sequence that controls expression of the nucleotide sequence in a host cell.

10. A genetically engineered host cell containing the nucleotide sequence of claim 2, 3, 4 or 5.

11. A genetically engineered host cell containing the nucleotide sequence of claim 2, 3, 4 or 5 operatively associated with a regulatory nucleotide sequence that controls expression of the nucleotide sequence in a host cell.

12. The genetically engineered host cell of claim 11 in which the host cell is prokaryotic.

13. The genetically engineered host cell of claim 11 in which the host cell is eukaryotic.

14. A method for detecting the presence of a nucleic acid molecule according to claim 2 or 3, in a subject, comprising:

(a) contacting a cell or an extract thereof from said subject with a nucleic acid probe encoding at least a portion of SEQ ID NO:2 or 3 under high stringency conditions; and (b) measuring the hybridization of said probe to the nucleic acid molecules of said cell or an extract thereof, thereby detecting the presence of said nucleic acid molecule.

15. The method of claim 14, additionally comprising before step (a): selectively amplifying said nucleic acid molecule according to claim 2 or 3.

* * * * *